US007851073B2

(12) United States Patent
Inoue et al.

(10) Patent No.: US 7,851,073 B2
(45) Date of Patent: Dec. 14, 2010

(54) ORGANIC ELECTROLUMINESCENCE DEVICE AND MATERIAL FOR ORGANIC ELECTROLUMINESCENCE DEVICE

(75) Inventors: Tetsuya Inoue, Sodegaura (JP); Masakazu Funahashi, Sodegaura (JP); Yoriyuki Takashima, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 586 days.

(21) Appl. No.: 11/855,645

(22) Filed: Sep. 14, 2007

(65) Prior Publication Data

US 2008/0071122 A1 Mar. 20, 2008

(30) Foreign Application Priority Data

Sep. 15, 2006 (JP) ............................ 2006-250958

(51) Int. Cl.
*H01J 1/62* (2006.01)
*C09K 11/06* (2006.01)

(52) U.S. Cl. ...................................... 428/690; 428/917

(58) Field of Classification Search ...................... None
See application file for complete search history.

(56) References Cited

FOREIGN PATENT DOCUMENTS

JP 2005240008 * 9/2005

OTHER PUBLICATIONS

U.S. Appl. No. 11/932,100, filed Oct. 31, 2007, Takashima et al.

* cited by examiner

*Primary Examiner*—Karl J Puttlitz
(74) *Attorney, Agent, or Firm*—Oblon, Spivak, McClelland, Maier & Neustadt, L.L.P.

(57) ABSTRACT

It is an object of the present invention to provide a novel compound useful as a constituent of an organic EL element and the use of the compound permits the realization of a highly practical organic EL element whose driving voltage is substantially low and which has a low leakage current. Accordingly, the present invention herein provides a fluoranthene compound represented by the following general formula (1):

A-L-B (1)

wherein A and B each represent a monovalent group having a fluoranthene structure represented by the following general formula (2), provided that A is linked to the group L present in the general formula (1), at the carbon atom selected from those specified by the numerical values of 7 to 10 appearing in Formula (2) and that B is linked to the group L present in Formula (1), at the carbon atom selected from those specified by the numerical values of 1 to 6 appearing in Formula (2):

(2)

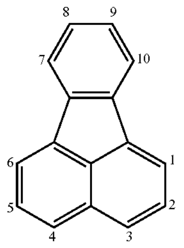

wherein L is a member selected from the group consisting of a single bond, substituted or unsubstituted arylene groups each having 6 to 40 carbon atoms, divalent groups derived from substituted or unsubstituted arylamines each having 6 to 40 carbon atoms, divalent groups derived from substituted or unsubstituted heterocyclic rings each having 3 to 40 carbon atoms and substituted or unsubstituted ethenylene groups.

10 Claims, No Drawings

ORGANIC ELECTROLUMINESCENCE DEVICE AND MATERIAL FOR ORGANIC ELECTROLUMINESCENCE DEVICE

TECHNICAL FIELD

The present invention relates to an organic electroluminescent element comprising a fluoranthene compound and more specifically to an organic electroluminescent element which has a longer lifetime, and can emit blue light rays at a high efficiency, because of the use of a fluoranthene compound incorporated into the light-emitting layer thereof.

BACKGROUND ART

The organic electroluminescent element (hereunder "EL" will also be used as the abbreviation of the term "electroluminescence" or "electroluminescent") is a spontaneously light-emitting or self-light-emitting element which makes use of such a principle that a fluorescent substance undergoes light-emission by the energy generated through the recombination of holes injected through the anode with electrons injected through the cathode, when an electric field is applied to the organic EL element. Organic EL elements composed of organic materials have vigorously been studied by a variety of research institutions, since C. W. Tang et al. of Eastman Kodak Co. reported a low voltage-operable organic EL element composed of a laminated element (see, for instance, C. W. Tang, S. A. Vanslyke, Applied Physics Letters, 1987, 51:913). Tang et al. employ tris-(8-quinolinolato) aluminum in a light-emitting layer and a triphenyl-diamine derivative in a hole-transporting layer. The use of a laminated structure will be advantageous in, for instance, that it can increase the efficiency of injecting holes into the light-emitting layer, that it can block the electrons injected through the cathode to thus improve the generation efficiency of excitons formed through the recombination holes with electrons and that it permits the restraint of the generated excitons in the light-emitting layer. Examples of the structures of such organic EL elements well known in the art like the example discussed above include a two-layer structure comprising a hole-transporting (or hole-injecting) layer and an electron-transporting and light-emitting layer; and a three-layer structure comprising a hole-transporting (or hole-injecting) layer, a light-emitting layer and an electron-transporting (or electron-injecting) layer. In respect of the element having such a laminated structure, there have variously been investigated and devised, the structures of such an element and the production methods thereof.

In addition, light-emitting materials known in this art include, for instance, chelate complexes such as tris-(8-quinolinolato) aluminum complex; and light-emitting materials such as coumarin derivatives, tetraphenyl butadiene derivatives, bis-styryl-arylene derivatives, and oxadiazole derivatives. In this respect, it has been reported that these substances permit the emission of light rays whose wavelengths fall within the visible light region extending from blue to red light rays and there has accordingly been desired for the development of a color-display element using, for instance, these substances (see, for instance, Patent Document 1, Patent Document 2 and Patent Document 3 specified below).

Moreover, Patent Document 4 and Patent Document 5 disclose elements which make use of bis-anthracene derivatives as light-emitting substances. In this connection, the bis-anthracene derivatives are used as materials capable of emitting blue light rays, but they have still been insufficient since they can never provide the efficiency and lifetime of practically acceptable levels.

Furthermore, there have been disclosed elements which make use of symmetrical pyrene derivatives as light-emitting substances in Patent Document 6, Patent Document 7, Patent Document 8 and Patent Document 9. Such symmetrical pyrene derivatives can be used as materials capable of emitting blue light rays, but it has been found that these elements are insufficient in their lifetime and accordingly, there has been desired for the further improvement of the lifetime thereof.

Further, Patent Document 10, Patent Document 11 and Patent Document 12 disclose elements which make use of fluoranthene compounds as light-emitting substances. Such fluoranthene compounds can be used as materials capable of emitting blue light rays, but the resulting elements have likewise been required for the further improvement of the lifetime thereof.

Patent Document 1: Japanese Un-Examined Patent Publication Hei 8-239655;

Patent Document 2: Japanese Un-Examined Patent Publication Hei 7-138561;

Patent Document 3: Japanese Un-Examined Patent Publication Hei 3-200889;

Patent Document 4: Japanese Patent No. 3,008,897;

Patent Document 5: Japanese Un-Examined Patent Publication Hei 8-12600;

Patent Document 6: Japanese Un-Examined Patent Publication 2001-118682;

Patent Document 7: Japanese Un-Examined Patent Publication 2002-63988;

Patent Document 8: Japanese Un-Examined Patent Publication 2004-75567;

Patent Document 9: Japanese Un-Examined Patent Publication 2004-83481;

Patent Document 10: Japanese Un-Examined Patent Publication 2002-69044;

Patent Document 11: International Publication No. 02/085822 pamphlet;

Patent Document 12: International Patent Publication No. 2005/033051 pamphlet

DISCLOSURE OF THE INVENTION

The present invention has been developed for the solution of the foregoing problems associated with the conventional techniques concerning the organic EL elements and accordingly, it is an object of the present invention to provide a novel compound useful as a constituent of such organic EL elements. It is another object of the present invention to provide a highly practically applicable organic EL element whose driving voltage is substantially low and which has a longer lifetime.

The inventors of this invention have conducted various studies to achieve the foregoing objects, have found that the use of a fluoranthene compound represented by the following general formula (1) in an organic electroluminescent element would permit the emission of blue light rays at a high light-emitting efficiency over a long period of time and have thus completed the present invention. More specifically, the present invention herein provides a fluoranthene compound represented by the following general formula (1):

$$A\text{-}L\text{-}B \quad (1)$$

wherein A and B each represent a monovalent group having a fluoranthene structure represented by the following general formula (2), provided that A is linked to the group L present in the general formula (1), at the carbon atom selected from those specified by the numerical values of 7 to 10 appearing in Formula (2) and that B is linked to the group L present in Formula (1), at the carbon atom selected from those specified by the numerical values of 1 to 6 appearing in Formula (2):

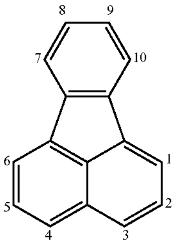

(2)

L is a member selected from the group consisting of a single bond, substituted or unsubstituted arylene groups each having 6 to 40 carbon atoms, divalent groups derived from arylamines each having 6 to 40 carbon atoms (wherein the aryl group may have a substituent), divalent groups derived from substituted or unsubstituted heterocyclic rings each having 3 to 40 carbon atoms and substituted or unsubstituted ethenylene groups.

According to another aspect of the present invention, there is also provided a material used for preparing an organic electroluminescent element and a light-emitting material, which comprises the foregoing fluoranthene compound.

According to a further aspect of the present invention, there is provided an organic electroluminescent element in which an organic compound layer having a single layer or multiple-layer structure comprising at least a light-emitting layer is sandwiched between a pair of electrodes, the electroluminescent element being characterized in that it comprises at least one fluoranthene compound defined above.

According to a still further aspect of the present invention, there is provided a device provided with the foregoing organic EL element.

BEST MODE FOR CARRYING OUT THE INVENTION (Fluoranthene Compounds)

The fluoranthene compound of the present invention is one represented by the following general formula (1):

A-L-B (1)

wherein A and B each represent a monovalent group having a fluoranthene structure represented by the following general formula (2), provided that A is linked to the group L present in the general formula (1), at the carbon atom selected from those specified by the numerical values of 7 to 10 appearing in Formula (2) and that B is linked to the group L present in Formula (1), at the carbon atom selected from those specified by the numerical values of 1 to 6 appearing in Formula (2):

(2)

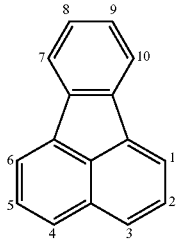

L is a member selected from the group consisting of a single bond, substituted or unsubstituted arylene groups each having 6 to 40 carbon atoms, divalent groups derived from arylamines each having 6 to 40 carbon atoms (wherein the aryl group may have a substituent), divalent groups derived from substituted or unsubstituted heterocyclic rings each having 3 to 40 carbon atoms and substituted or unsubstituted ethenylene groups.

In Formula (1), L is a member selected from the group consisting of a single bond, substituted or unsubstituted arylene groups each having 6 to 40 carbon atoms, divalent groups derived from arylamines each having 6 to 40 carbon atoms (wherein the aryl group may have a substituent), divalent groups derived from substituted or unsubstituted heterocyclic rings each having 3 to 40 carbon atoms and substituted or unsubstituted ethenylene groups. Preferably, the group L is a member selected from the group consisting of divalent groups derived from phenylene, biphenylene, naphthacene, anthrecene, ethenylene and divalent groups derived from fluorenes, thiophenes, thiadiazoles, pyrazines, amines, arylamines, triarylamines, carbazoles, pyrroles, thiazoles, benzothiazoles, benzothiadiazoles, phenanthrolines, quinones and quinoxalines. These divalent groups may have a substituent. Examples of such substituents include halogen atoms, a hydroxyl group, a nitro group, a cyano group, alkyl groups, aryl groups, cycloalkyl groups, alkoxy groups, aromatic heterocyclic rings, aralkyl groups, aryloxy groups, arylthio groups, alkoxycarbonyl groups and a carboxyl group.

More preferably, the group L is a member selected from the group consisting of the following divalent groups:

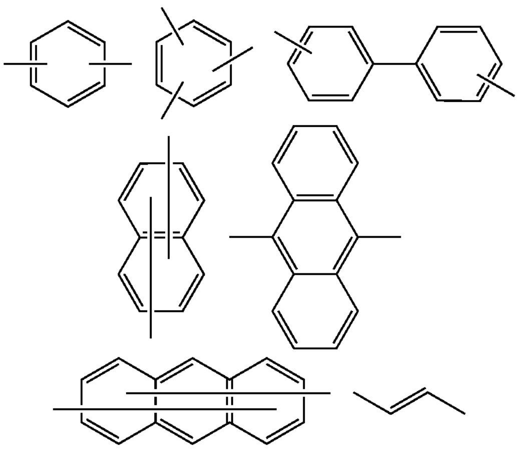

-continued

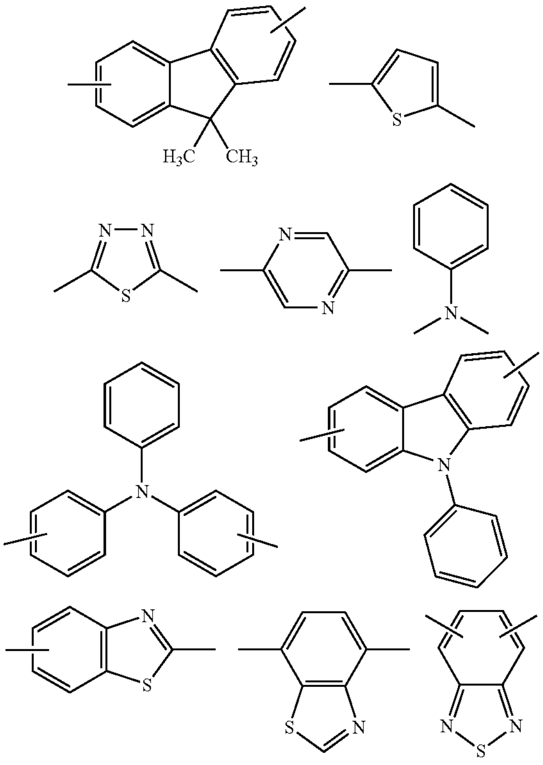

Preferably, the group A appearing in the foregoing general formula (1) is a monovalent group represented by the following general formula (3) and the group B is a monovalent group represented by the following general formula (4) or (5):

(3)

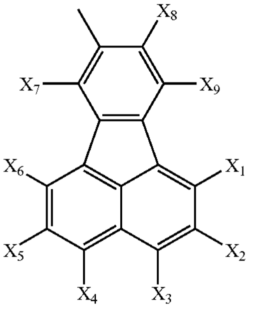

(4)

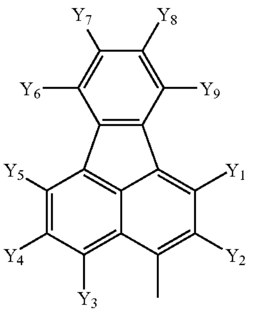

-continued (5)

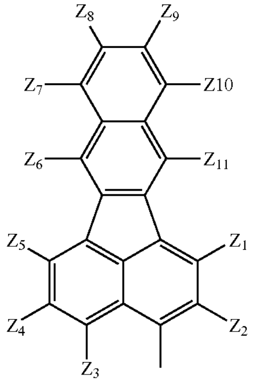

In the foregoing general formulas (3) to (5), $X_1$ to $X_9$, $Y_1$ to $Y_9$, and $Z_1$ to $Z_{11}$ each represent a member selected from the group consisting of a hydrogen atom, substituted or unsubstituted aryl or heteroaryl groups whose nucleic atom number ranges from 5 to 50, substituted or unsubstituted alkyl groups each having 1 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxycarbonyl groups each having 2 to 50 carbon atoms, amino groups each having a substituted or unsubstituted aryl group whose nucleic atom number ranges from 5 to 50, halogen atoms, a cyano group, a nitro group, a hydroxyl group, and a carboxyl group. In respect of these groups $X_1$ to $X_9$, $Y_1$ to $Y_9$, and $Z_1$ to $Z_{11}$, any possible combination of neighboring groups may be bonded together to thus form a saturated or unsaturated ring structure and the resulting ring structure may have a substituent.

The substituted or unsubstituted aryl groups whose nucleic atom number ranges from 5 to 50 of $X_1$-$X_9$, $Y_1$-$Y_9$ and $Z_1$-$Z_{11}$ in the foregoing general formulas (3) to (5) include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl groups. Substituted or unsubstituted aryl groups whose nucleic atom number ranges from 6 to 20 are preferred.

The substituted or unsubstituted heteroaryl groups whose nucleic atom number ranges from 5 to 50 of $X_1$-$X_9$, $Y_1$-$Y_9$ and $Z_1$-$Z_{11}$ in the foregoing general formulas (3) to (5) include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl 1-indolyl, 4-t-butyl 1-indolyl, 2-t-butyl 3-indolyl and 4-t-butyl 3-indolyl groups. Substituted or unsubstituted heteroaryl groups whose nucleic atom number ranges from 5 to 20 are preferred.

The substituted or unsubstituted alkyl groups each having 1 to 50 carbon atoms of $X_1$-$X_9$, $Y_1$-$Y_9$ and $Z_1$-$Z_{11}$ in foregoing general formulas (3) to (5) include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl groups. Substituted or unsubstituted alkyl groups each having 1 to 20 carbon atoms are preferred.

The substituted or unsubstituted alkoxy groups having 1 to 50 carbon atoms represented by the groups $X_1$ to $X_9$, $Y_1$ to $Y_9$, and $Z_1$ to $Z_{11}$ appearing in the foregoing general formulas (3) to (5) is one represented by the formula: —OY in which Y may be, for instance, those identical to the substituted or unsubstituted alkyl groups each having 1 to 50 carbon atoms, represented by the foregoing groups $X_1$ to $X_9$, $Y_1$ to $Y_9$, and $Z_1$ to $Z_{11}$. Preferably used herein include, for instance, substituted or unsubstituted alkoxy groups each having 1 to 20 carbon atoms.

The substituted or unsubstituted aralkyl groups each having 6 to 50 carbon atoms of $X_1$-$X_9$, $Y_1$-$Y_9$ and $Z_1$-$Z_{11}$ in foregoing general formulas (3) to (5) include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl groups. Substituted or unsubstituted aralkyl groups each having 7 to 20 carbon atoms are preferred.

The substituted or unsubstituted aryloxy groups whose nucleic atom number ranges from 5 to 50 and the substituted or unsubstituted arylthio groups whose nucleic atom number ranges from 5 to 50 represented by the groups $X_1$ to $X_9$, $Y_1$ to $Y_9$, and $Z_1$ to $Z_{11}$ appearing in the foregoing general formulas (3) to (5) are those represented by the following general formulas: —OY' and —SY", respectively. In these formulas, Y' and Y" may be, for instance, those identical to the foregoing substituted or unsubstituted aryl groups whose nucleic atom number ranges from 5 to 50, represented by the foregoing groups $X_1$ to $X_9$, $Y_1$ to $Y_9$, and $Z_1$ to $Z_{11}$. Preferably used herein include, for instance, substituted or unsubstituted aryloxy groups whose nucleic atom number ranges from 5 to 20 and substituted or unsubstituted arylthio groups whose nucleic atom number ranges from 5 to 20.

The substituted or unsubstituted alkoxy-carbonyl groups having 2 to 50 carbon atoms represented by the groups $X_1$ to $X_9$, $Y_1$ to $Y_9$, and $Z_1$ to $Z_{11}$ appearing in the foregoing general formulas (3) to (5) is one represented by the following general formula: —COOZ in which Z may be, for instance, those identical to the substituted or unsubstituted alkyl groups each having 1 to 50 carbon atoms, represented by the foregoing groups $X_1$ to $X_9$, $Y_1$ to $Y_9$, and $Z_1$ to $Z_{11}$. Preferably used herein include, for instance, substituted or unsubstituted alkoxy groups whose alkyl group has 1 to 20 carbon atoms.

The substituted or unsubstituted aryl group, whose nucleic atom number ranges from 5 to 50, of the amino group having the substituted or unsubstituted aryl group whose nucleic atom number ranges from 5 to 50, represented by the groups $X_1$ to $X_9$, $Y_1$ to $Y_9$, and $Z_1$ to $Z_{11}$ appearing in the foregoing general formulas (3) to (5) may be, for instance, those identical to the foregoing substituted or unsubstituted aryl groups whose nucleic atom number ranges from 5 to 50, represented by the foregoing groups $X_1$ to $X_9$, $Y_1$ to $Y_9$, and $Z_1$ to $Z_{11}$. Preferred are, for instance, amino groups each having a substituted or unsubstituted aryl group whose nucleic atom number ranges from 5 to 20.

The halogen atoms represented by the groups $X_1$ to $X_9$, $Y_1$ to $Y_9$, and $Z_1$ to $Z_{11}$ appearing in the foregoing general formulas (3) to (5) may be, for instance, fluorine, chlorine, bromine and iodine atoms.

Examples of the substituents for the groups represented by the foregoing groups $X_1$ to $X_9$, $Y_1$ to $Y_9$, and $Z_1$ to $Z_{11}$ include halogen atoms, a hydroxyl group, a nitro group, a cyano group, alkyl groups, aryl groups, cycloalkyl groups, alkoxy groups, aromatic heterocyclic groups, aralkyl groups, aryloxy groups, arylthio groups, alkoxycarbonyl groups and carboxyl groups.

The saturated or unsaturated ring structure formed from any possible combination of the neighboring groups selected from the foregoing groups $X_1$ to $X_9$, $Y_1$ to $Y_9$, and $Z_1$ to $Z_{11}$, is preferably 5-membered or 6-membered one and these ring structures may be substituted.

Specific examples of the fluoranthene compounds of the present invention represented by the general formula (1) will be listed below, but the fluoranthene compounds of the present invention are not limited to these specifically illustrated compounds at all.

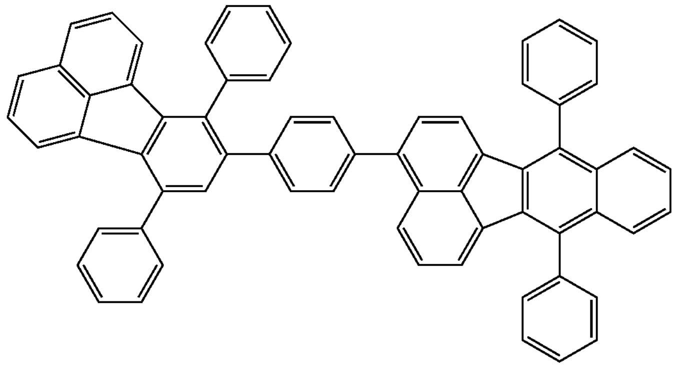

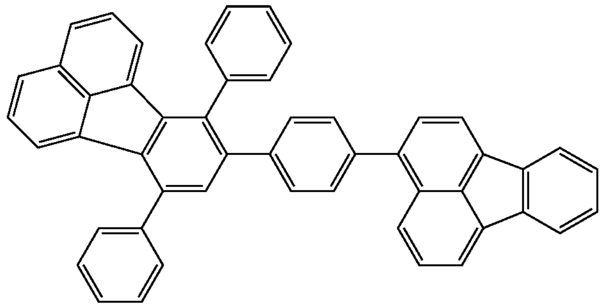

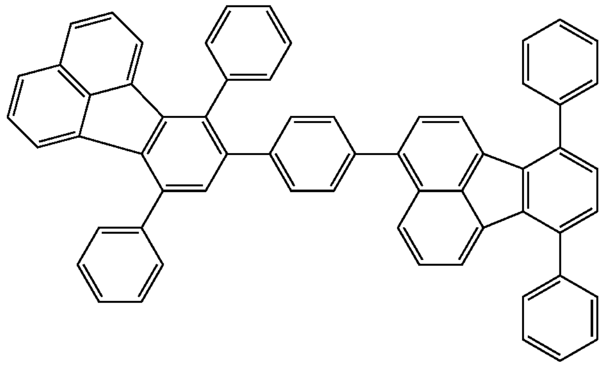

-continued
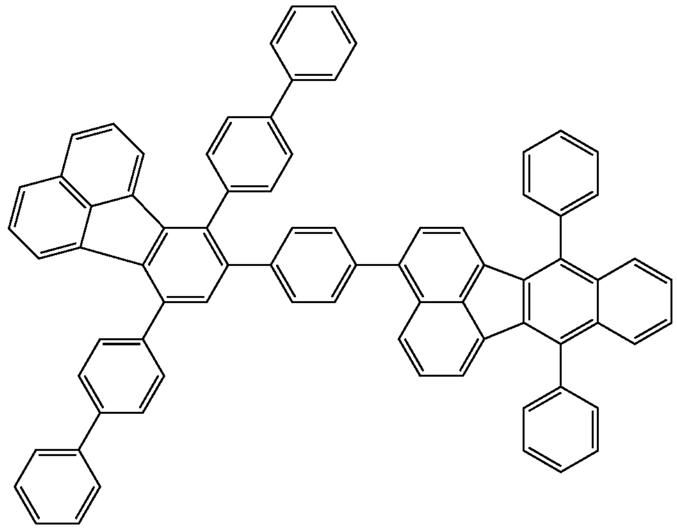
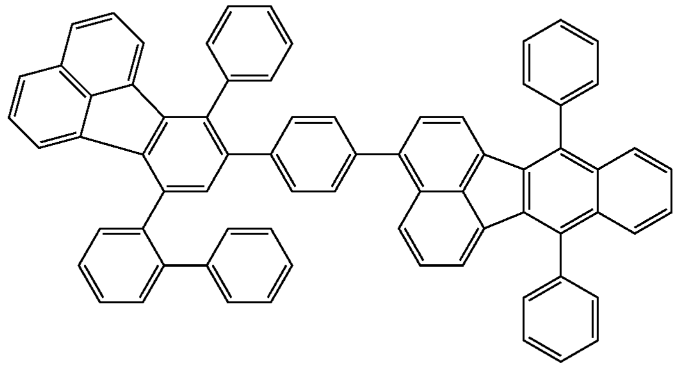
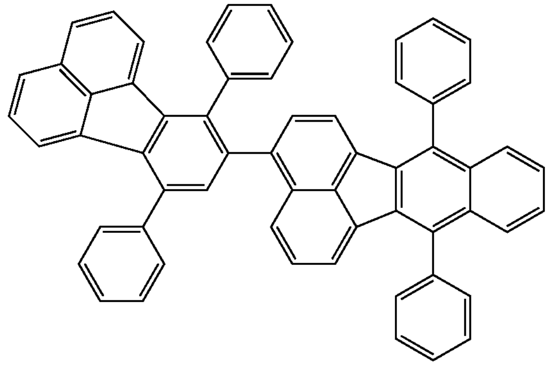
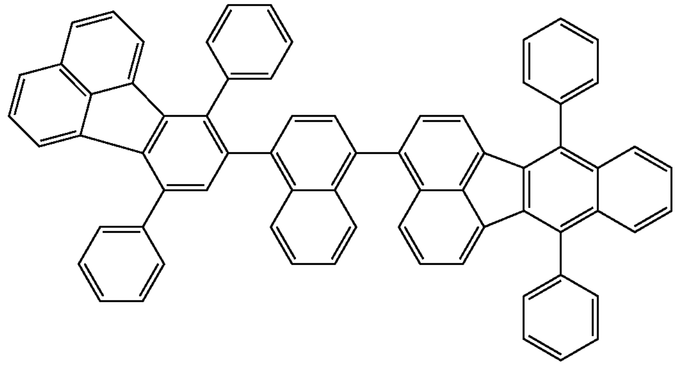

-continued
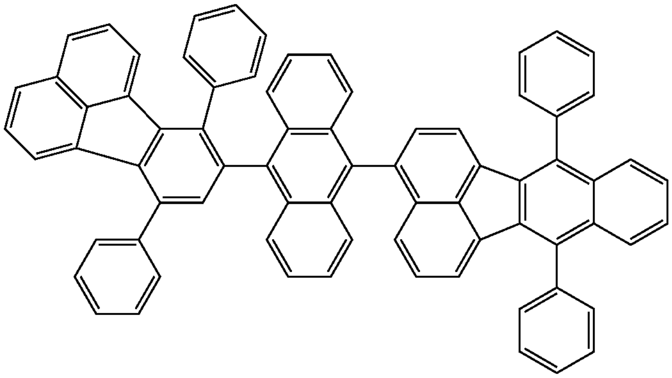
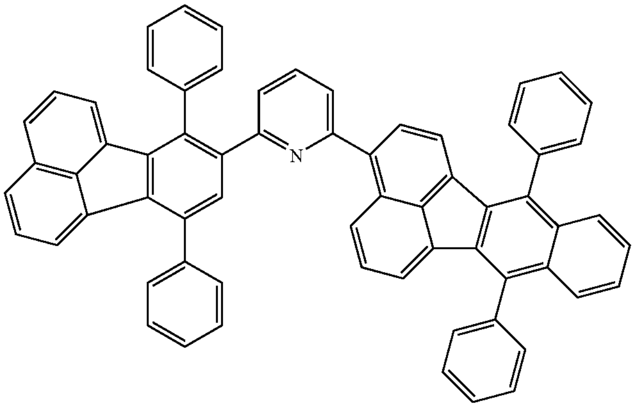
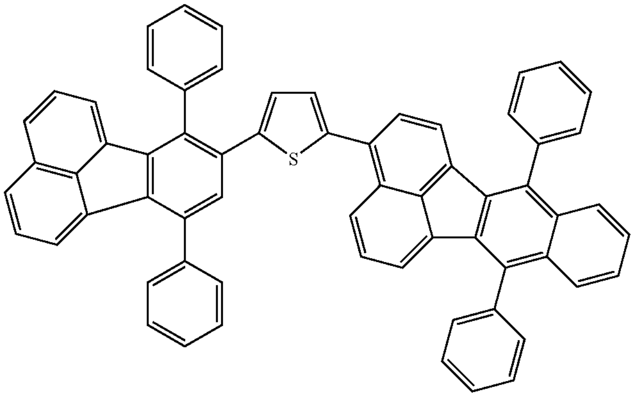
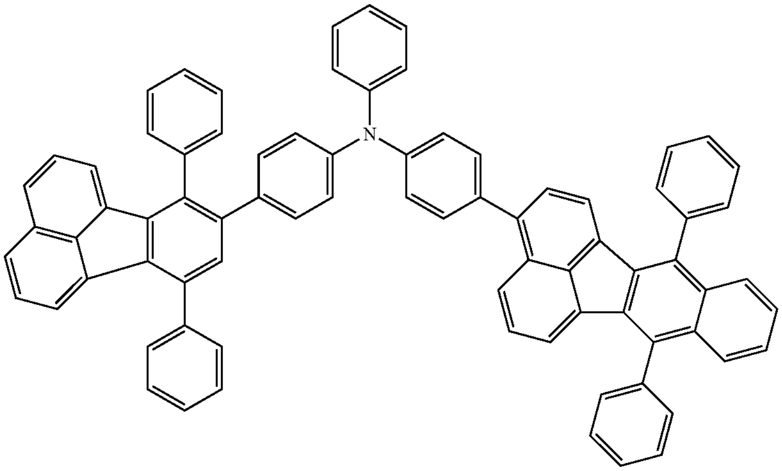

-continued

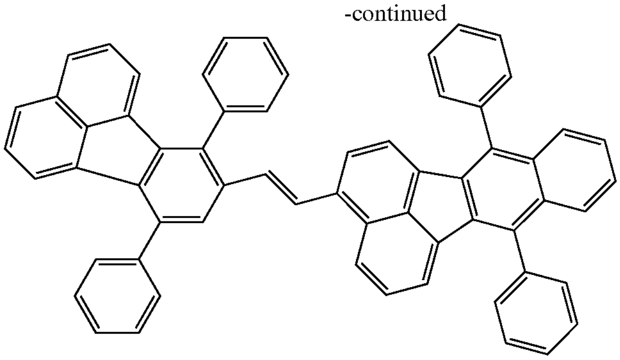

(Host Materials)

The fluoranthene compounds of the present invention represented by the general formula (1) is preferably used in combination with a compound represented by the following general formula (2a), when the former is used as a light-emitting material:

(2a)

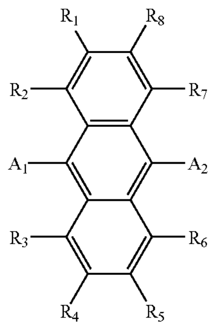

In the foregoing formula (2a), $A_1$ and $A_2$ each independently represent a group derived from a substituted or unsubstituted aromatic ring whose nucleic atom number ranges from 6 to 20. The aromatic ring may have at least one substituent. The foregoing substituent may be, for instance, a member selected from the group consisting of substituted or unsubstituted aryl groups whose nucleic carbon atom number ranges from 6 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group. In this respect, when the foregoing aromatic ring has at least 2 substituents, these substituents may be the same or different and any possible neighboring substituents may be bonded together to form a saturated or unsaturated ring structure.

$R_1$ to $R_8$ each independently represent a member selected from the group consisting of a hydrogen atom, substituted or unsubstituted aryl groups whose nucleic atom number ranges from 6 to 50, substituted or unsubstituted heteroaryl groups whose nucleic atom number ranges from 5 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group.

The group derived from the substituted or unsubstituted aromatic ring whose nucleic atom number ranges from 6 to 20 of $A_1$ and $A_2$ in the general formula (2a) includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl groups. A group derived from a substituted or unsubstituted aromatic ring whose nucleic atom number ranges from 10 to 14 is preferred and specifically, 1-naphthyl, 2-naphthyl and 9-phenanthryl groups are preferred.

The substituted or unsubstituted aryl groups whose nucleic carbon atom number ranges from 6 to 50 of the substituent of the foregoing aromatic ring include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl groups. Substituted or unsubstituted aryl groups whose nucleic carbon atom number ranges from 6 to 18 are preferred and specifically, phenyl, 1-naphthyl, 2-naphthyl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, o-tolyl, m-tolyl, p-tolyl and p-t-butylphenyl groups are preferred.

The substituted or unsubstituted aryl groups whose nucleic atom number ranges from 6 to 50 of $R_1$ to $R_8$ in the general formula (2a) include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl group.

The substituted or unsubstituted heteroaryl groups whose nucleic atom number ranges from 5 to 50 of $R_1$ to $R_8$ in the general formula (2a) include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl 1-indolyl, 4-t-butyl 1-indolyl, 2-t-butyl 3-indolyl and 4-t-butyl 3-indolyl group.

The substituted or unsubstituted alkyl groups each having 1 to 50 carbon atoms of $R_1$ to $R_8$ in the general formula (2a) and the substituent of the foregoing aromatic ring include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl group.

The substituted or unsubstituted cycloalkyl groups each having 3 to 50 carbon atoms of $R_1$ to $R_8$ in the general formula (2a) and the substituent of the foregoing aromatic ring include cyclopropyl, cyclobutyl, cyclopentyl, cyclohexyl, 4-methylcyclohexyl, 1-adamantyl, 2-adamantyl, 1-norbornyl and 2-norbornyl group.

The substituted or unsubstituted alkoxy groups each having 1 to 50 carbon atoms of $R_1$ to $R_8$ in the general formula (2a) and the substituent of the foregoing aromatic ring are those represented by the general formula: —OY in which Y may be, for instance, those identical to the substituted or unsubstituted alkyl groups each having 1 to 50 carbon atoms, discussed above in connection with the foregoing groups $R_1$ to $R_8$ and the substituents for the foregoing aromatic rings.

The substituted or unsubstituted aralkyl groups each having 6 to 50 carbon atoms of $R_1$ to $R_8$ in the general formula (2a) and the substituent of the foregoing aromatic ring includes benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl group.

The substituted or unsubstituted aryloxy groups and arylthio groups whose nucleic atom number ranges from 5 to 50 of $R_1$ to $R_8$ in the general formula (2a) and the substituent of the foregoing aromatic rings may be, for instance, those represented by the following general formulas: —OY' and —SY", respectively. In these formulas, Y' and Y" may be, for instance, those identical to the foregoing substituted or unsubstituted aryl groups whose nucleic atom number ranges from 6 to 50, discussed above in connection with the foregoing groups $R_1$ to $R_8$ and the substituents for the foregoing aromatic rings.

The substituted or unsubstituted alkoxy-carbonyl group having 1 to 50 carbon atoms of $R_1$ to $R_8$ in the general formula (2a) and the substituents of the foregoing aromatic rings is one represented by the following general formula: —COOZ in which Z may be, for instance, those identical to the substituted or unsubstituted alkyl groups each having 1 to 50 carbon atoms, discussed above in connection with the foregoing groups $R_1$ to $R_8$ and the foregoing aromatic rings.

The halogen atoms of $R_1$ to $R_8$ in the foregoing general formula (2a) and the substituents of the foregoing aromatic rings may be, for instance, fluorine, chlorine, bromine and iodine atoms.

Examples of the substituents for the groups represented by the foregoing groups $R_1$ to $R_8$ and for the foregoing aromatic rings include halogen atoms, a hydroxyl group, a nitro group, a cyano group, alkyl groups, aryl groups, cycloalkyl groups, alkoxy groups, aromatic heterocyclic groups, aralkyl groups, aryloxy groups, arylthio groups, alkoxycarbonyl groups and a carboxyl group.

Preferably, the anthracene derivatives represented by the foregoing general formula (2a) are, for instance, compounds each having a structure represented by the following general formula (2a'):

(2a')

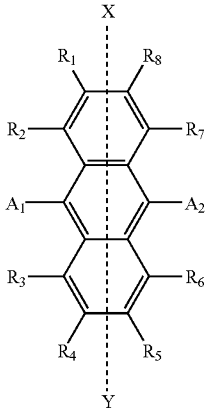

In the formula (2a'), $A_1$ and $A_2$ each independently represent a group derived from a substituted or unsubstituted aromatic ring whose ring-forming carbon atom number ranges from 6 to 20. The aromatic ring may have at least one substituent. The foregoing substituent may be, for instance, a member selected from the group consisting of substituted or unsubstituted aryl groups whose nucleic carbon atom number ranges from 6 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group. In this respect, when the foregoing aromatic ring has at least 2 substituents, these substituents may be the same or different and any possible neighboring substituents may be bonded together to form a saturated or unsaturated ring structure.

$R_1$ to $R_8$ each independently represent a member selected from the group consisting of a hydrogen atom, substituted or unsubstituted aryl groups whose nucleic carbon atom number ranges from 6 to 50, substituted or unsubstituted heteroaryl groups whose nucleic carbon atom number ranges from 5 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group.

In this respect, however, the substituents present on the 9-th and 10-th positions on the central anthracene ring represented by the general formula (2a') should not be symmetrical with respect to the longitudinal axis X-Y of the anthracene ring.

Specific examples of these substituents $A_1$, $A_2$ and $R_1$ to $R_8$ may be the same as those listed above in connection with the general formula (2a).

Specific examples of the anthracene derivatives represented by the general formula (2a) and used for forming the organic EL element of the present invention are various kinds of known anthracene derivatives, for instance, those having two anthracene skeletons within the molecule such as those described in sections [0043] to [0063] of Japanese Un-Examined Patent Publication (hereunder referred to as "J.P. KOKAI") 2004-356033; and compounds each having one anthracene skeleton such as those disclosed in International Patent Publication No. 2005/061656, Pamphlet, pp. 27-28. Typical examples thereof will be listed below:

2a-1

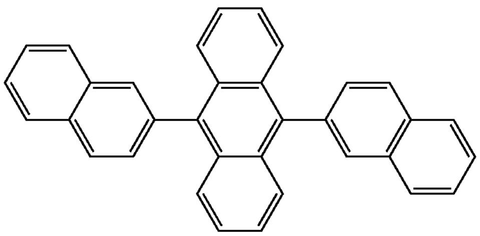

2a-2

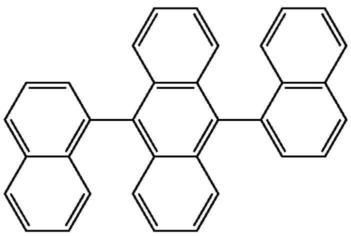

-continued
2a-3
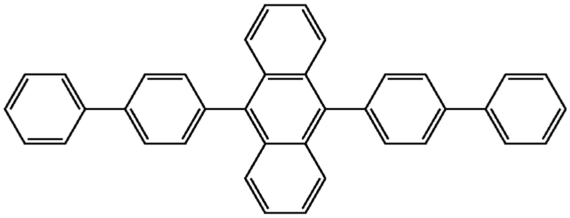
2a-4
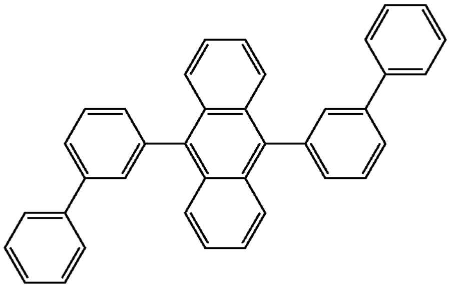
2a-5
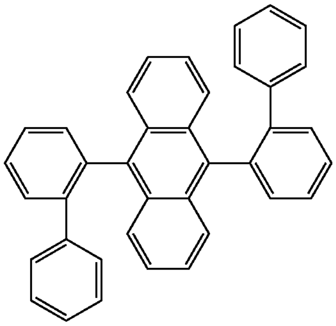
2a-6
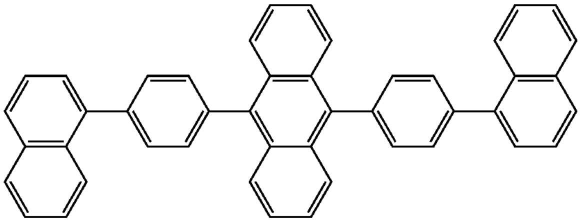
2a-7
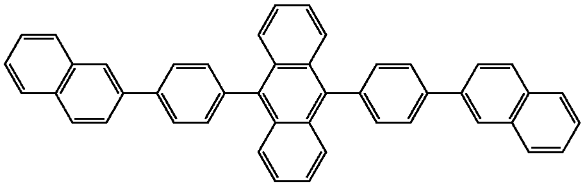
2a-8
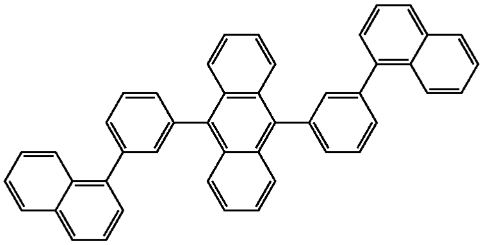
2a-9
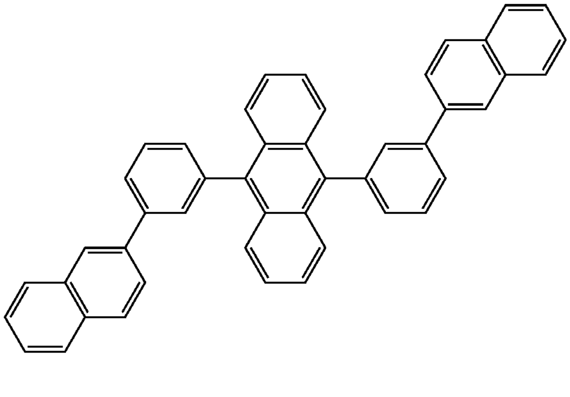
2a-10
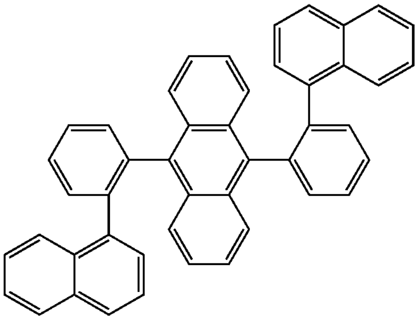

-continued
2a-11
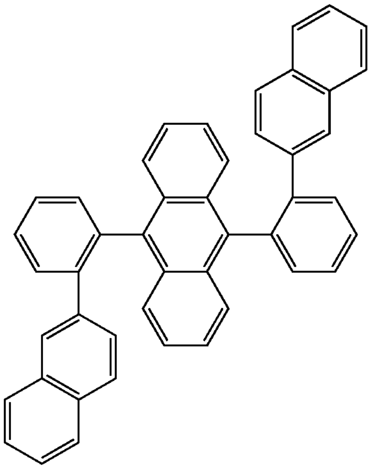
2a-12
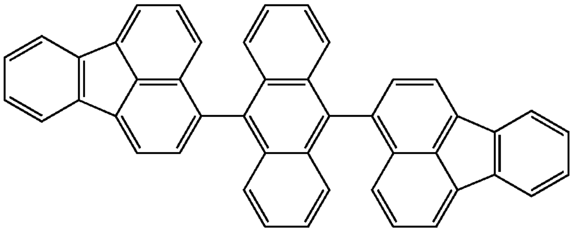
2a-13
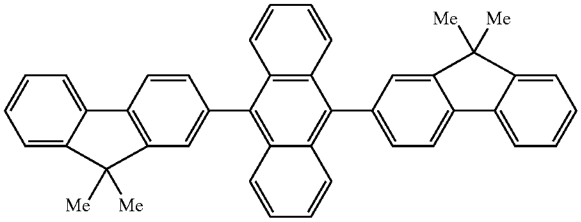
2a-14
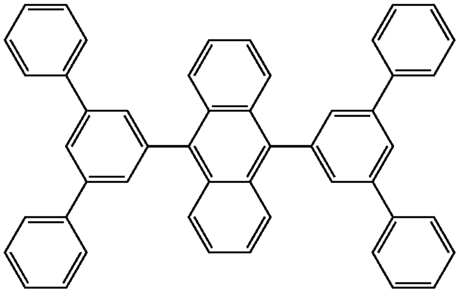
2a-15
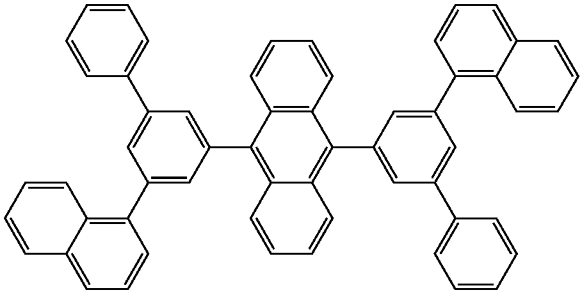
2a-16
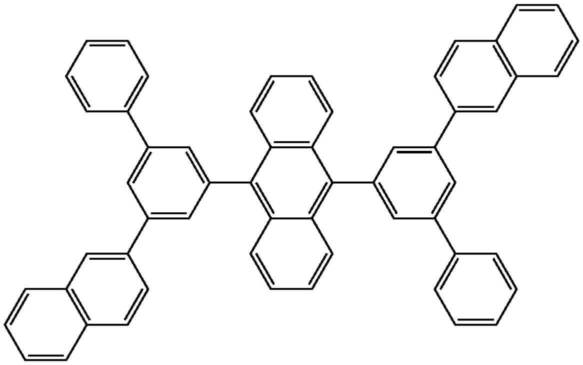
2a-17
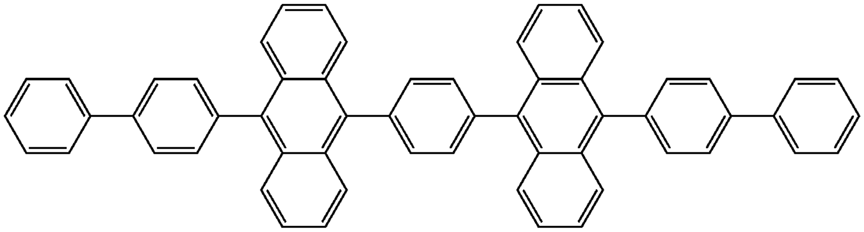

-continued
2a-18
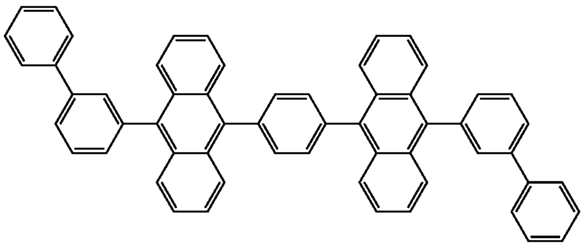
2a-19
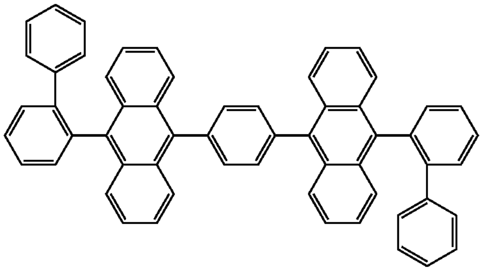
2a-20
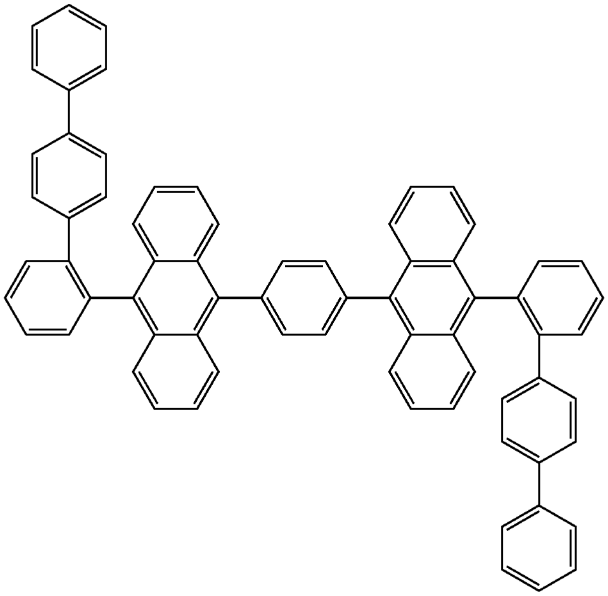
2a-21
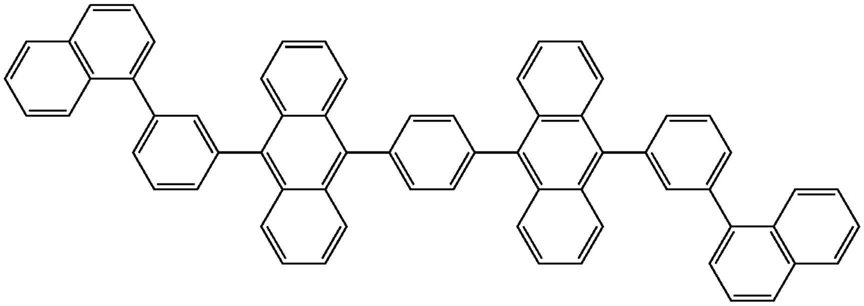
2a-22
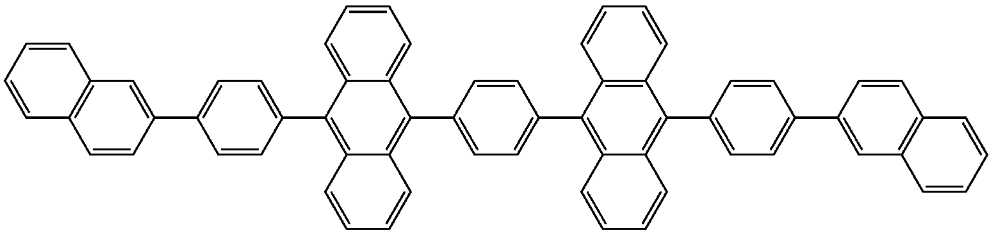

-continued
2a-23
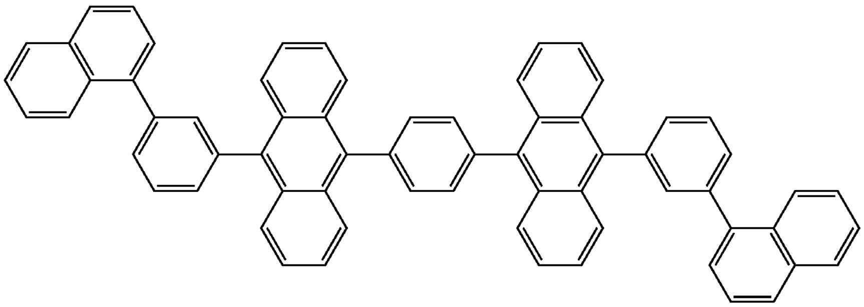
2a-24
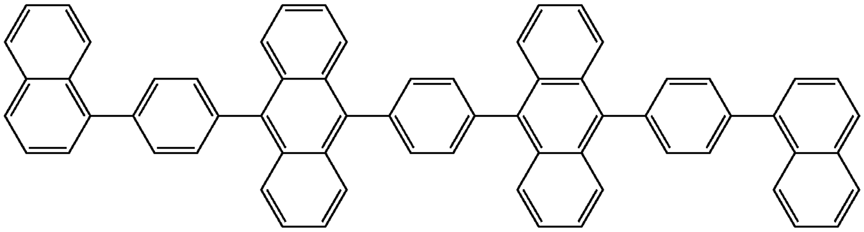
2a-25
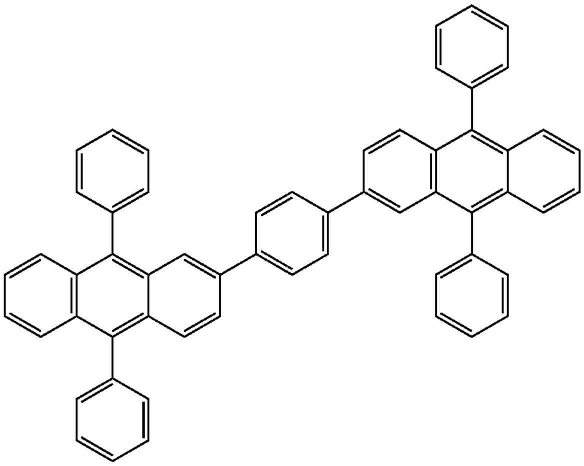
2a-26
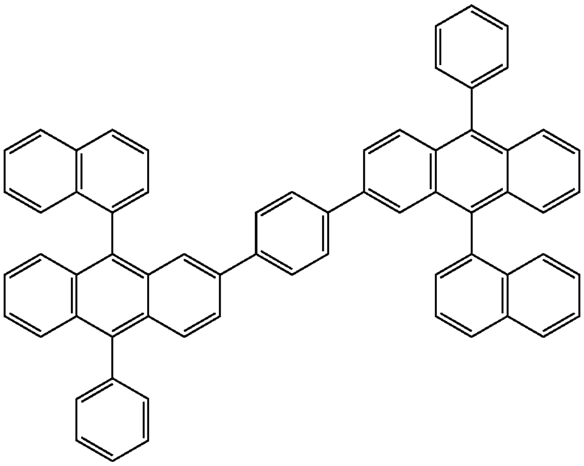
2a-27
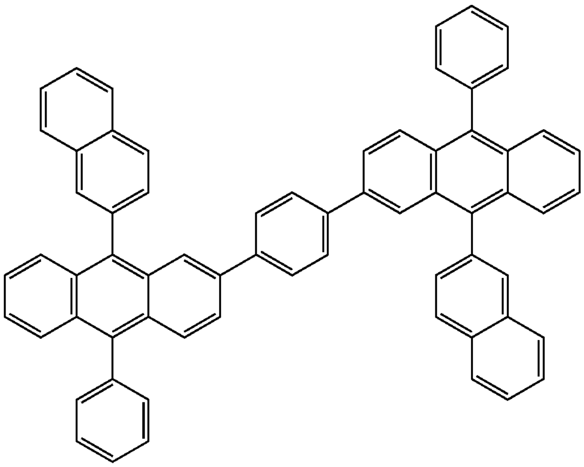
2a-28
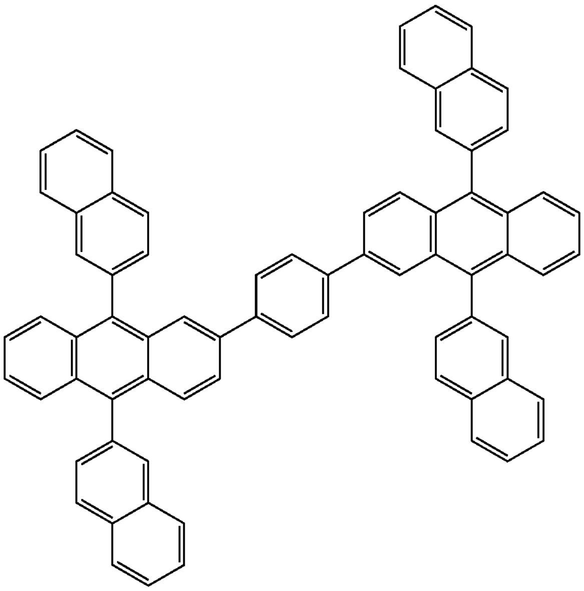

-continued
2a-29
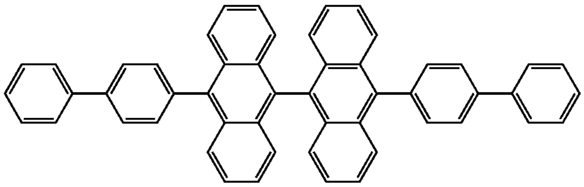
2a-30
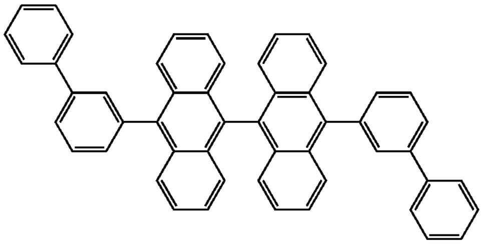
2a-31
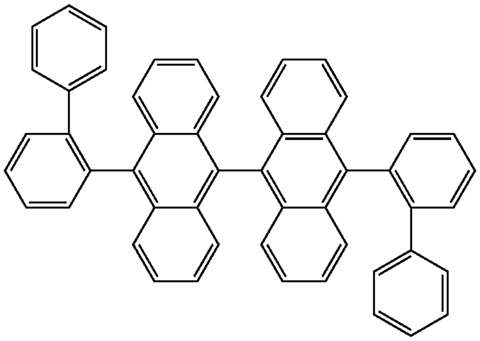
2a-32
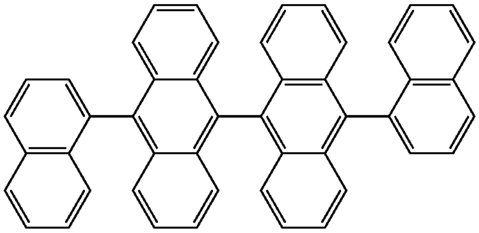
2a-33
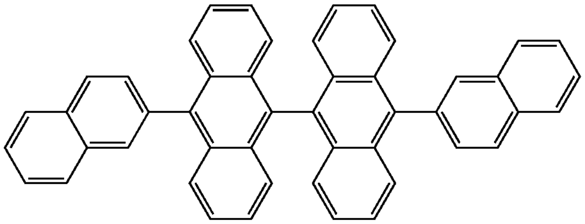
2a-34
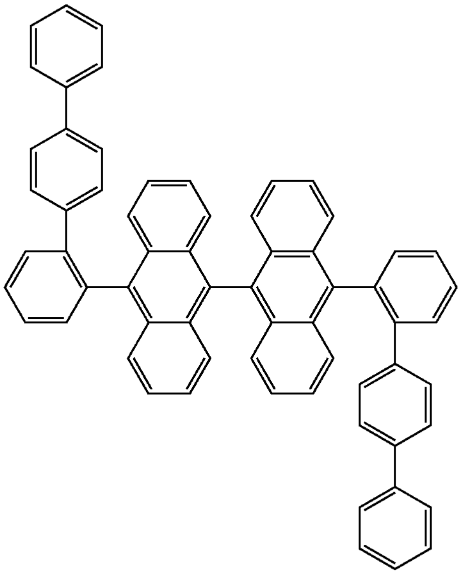
2a-35
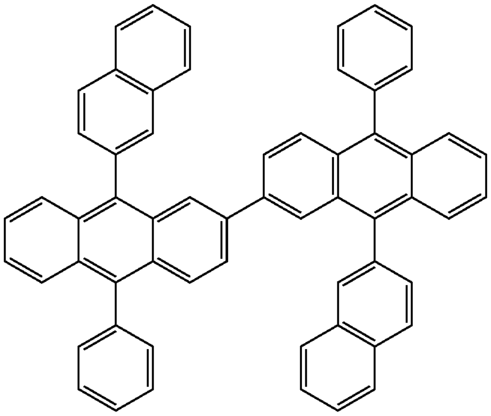
2a-36
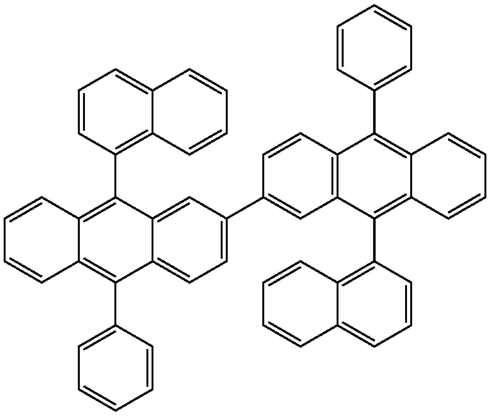

-continued
2a-37
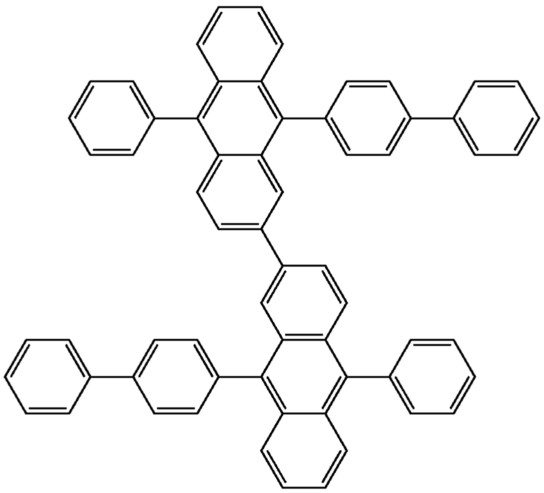
2a-38
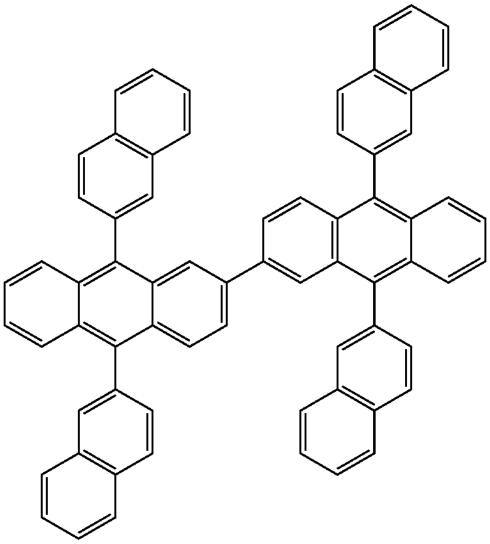
2a-39
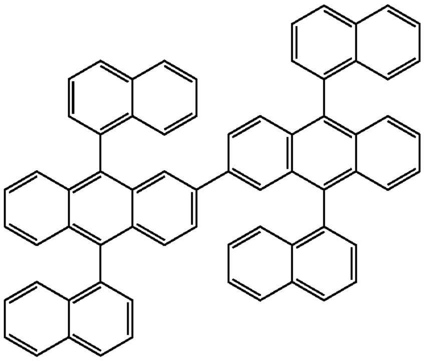
2a-40
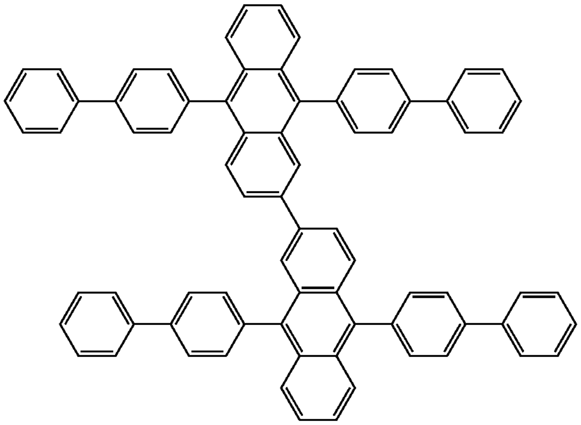
2a-41
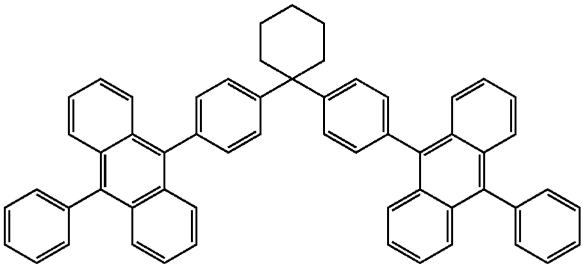
2a-42
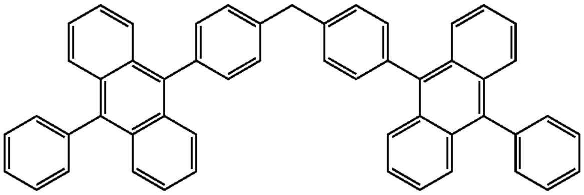
2a-43
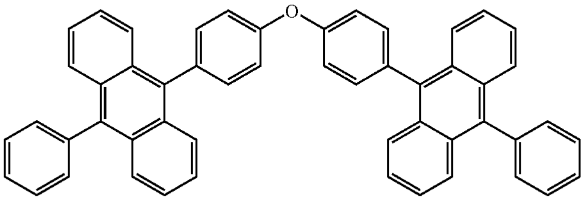
2a-44
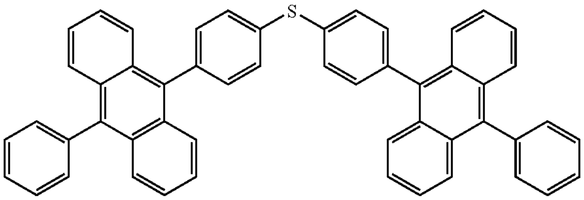

-continued
2a-45
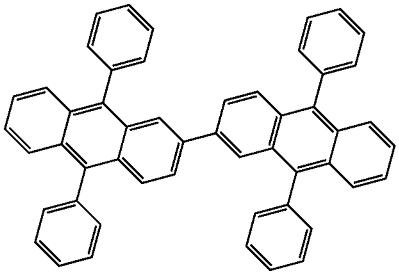
2a-46
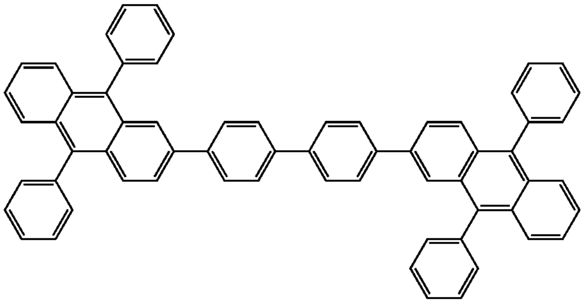
2a-47
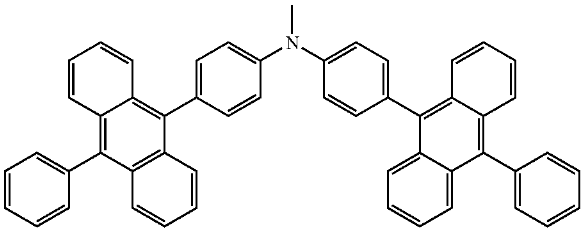
2a-48
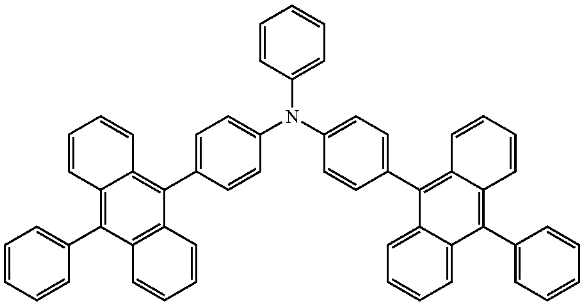
2a-49
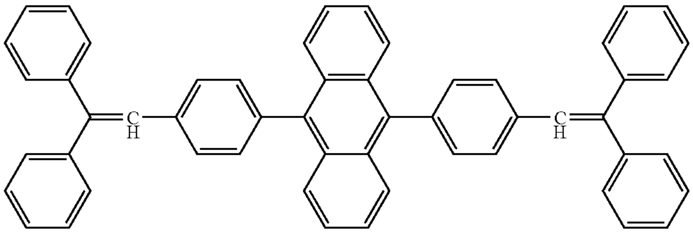
2a-50
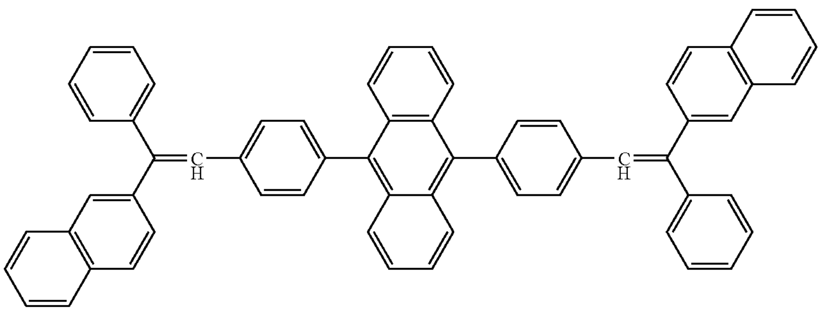

-continued
2a-51
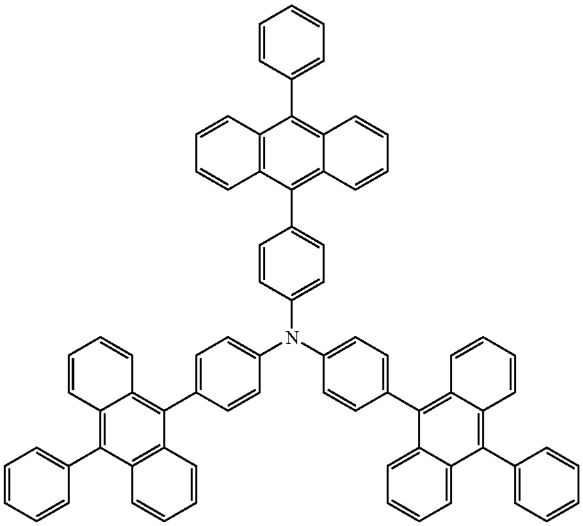
2a'-52
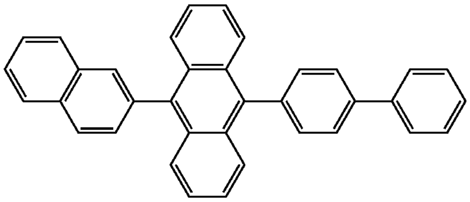
2a'-53
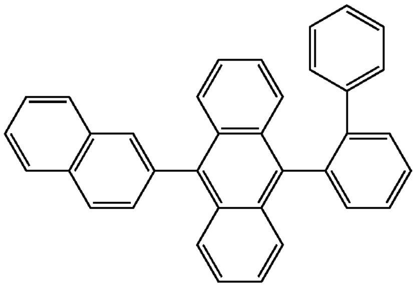
2a'-54
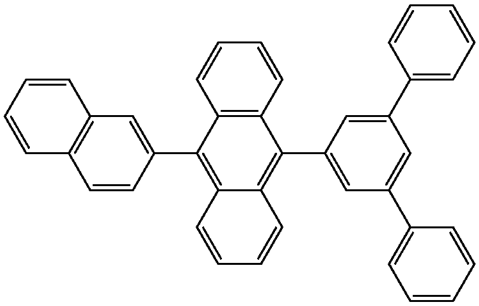
2a'-55
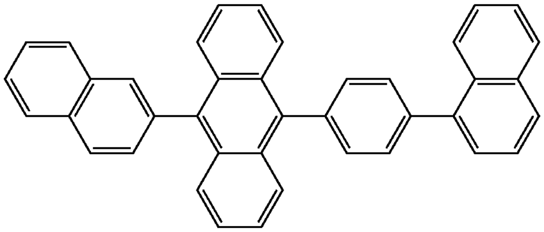
2a'-56
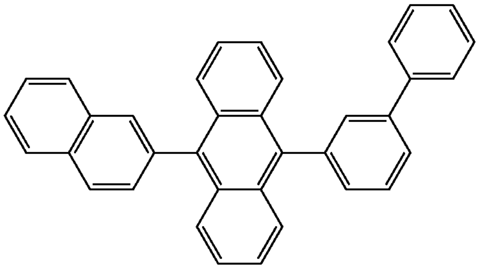
2a'-57
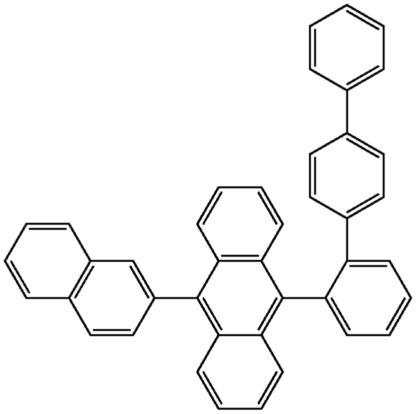
2a'-58
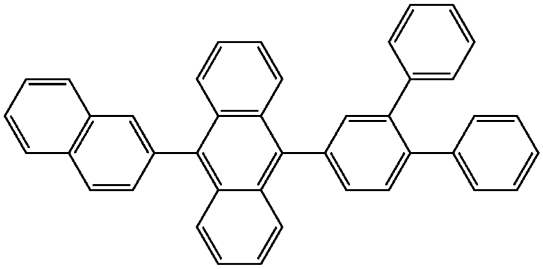

-continued
2a′-59
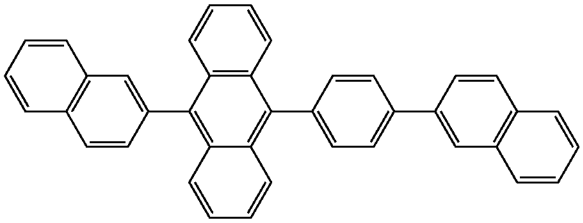
2a′-60
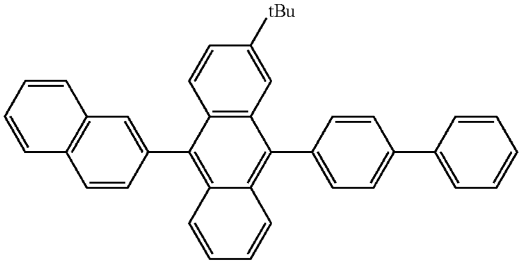
2a′-61
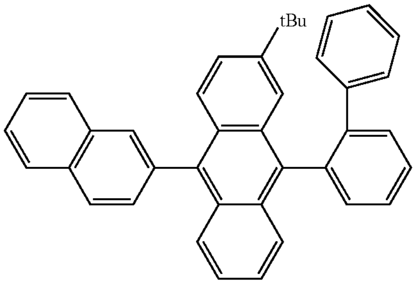
2a′-62
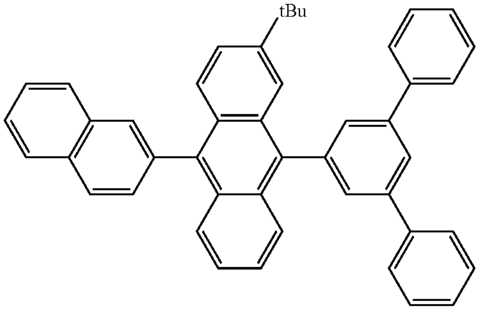
2a′-63
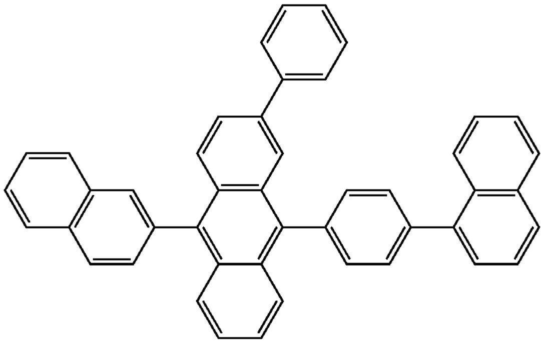
2a′-64
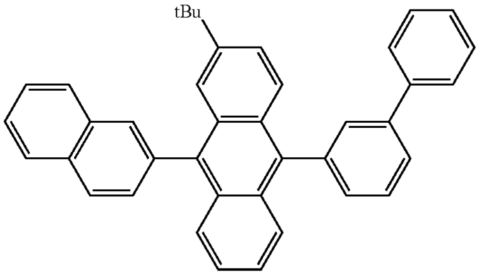
2a′-65
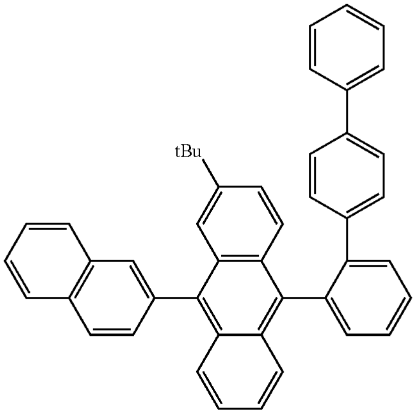
2a′-66
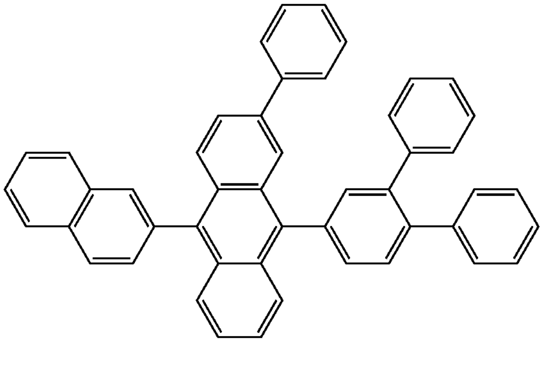

-continued
2a′-67
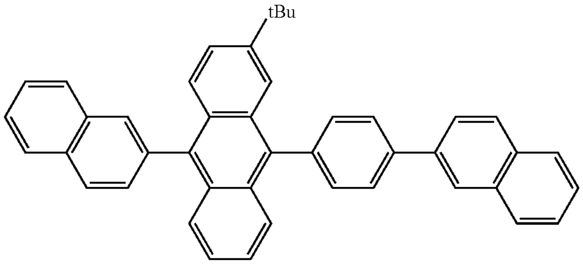
2a′-68
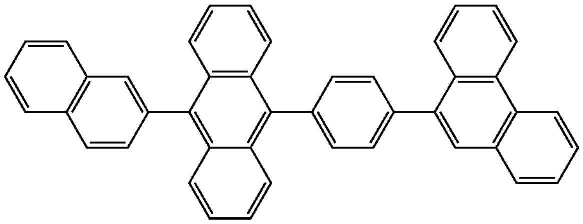
2a′-69
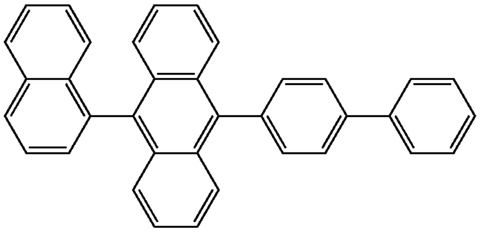
2a′-70
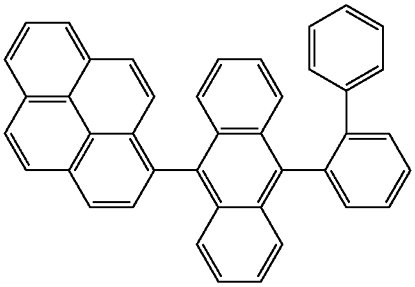
2a′-71
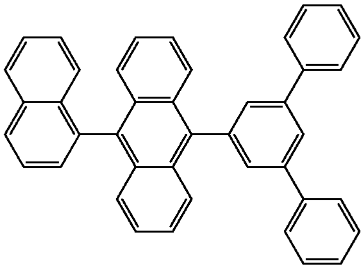
2a′-72
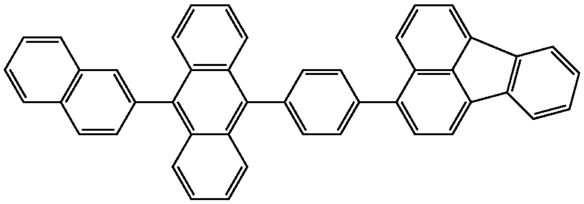
2a′-73
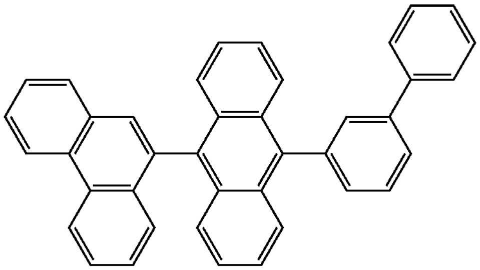
2a′-74
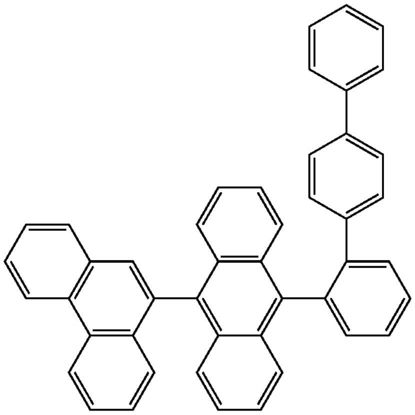

-continued
2a'-75
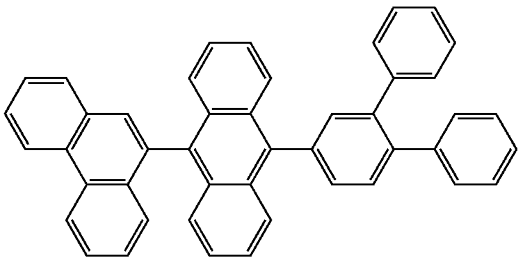
2a'-76
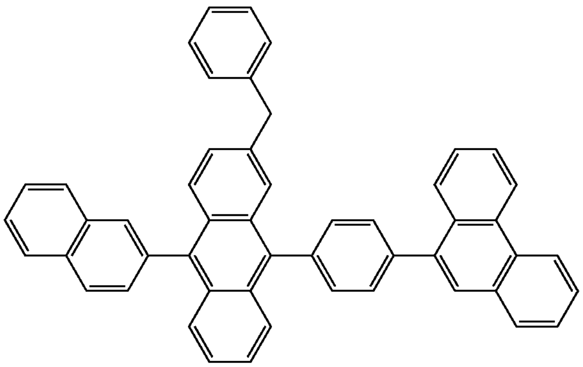
2a'-77
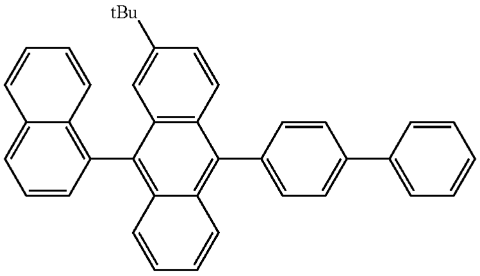
2a'-78
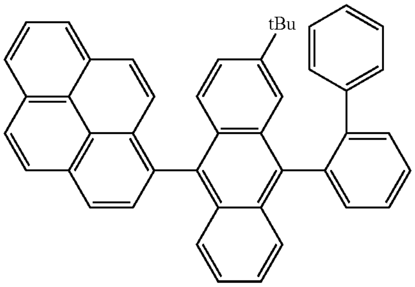
2a'-79
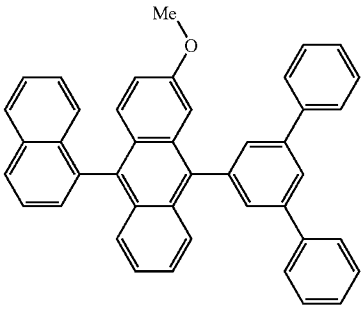
2a'-80
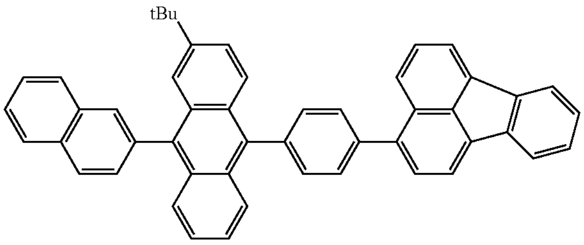
2a'-81
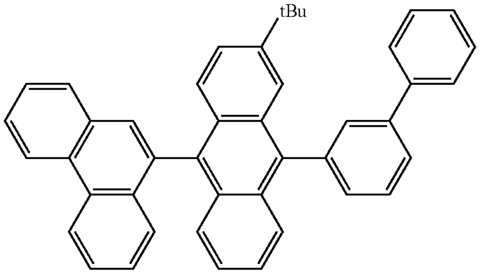
2a'-82
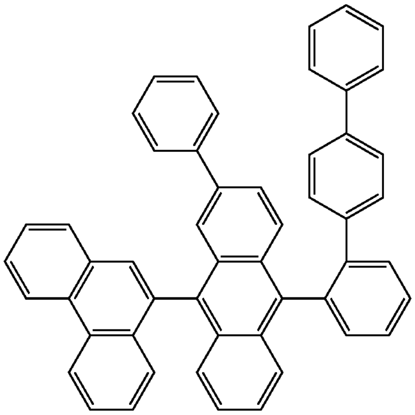

-continued
2a′-83
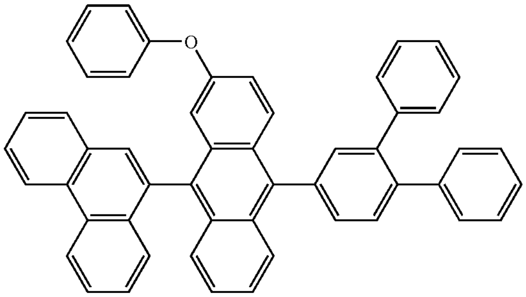
2a′-84
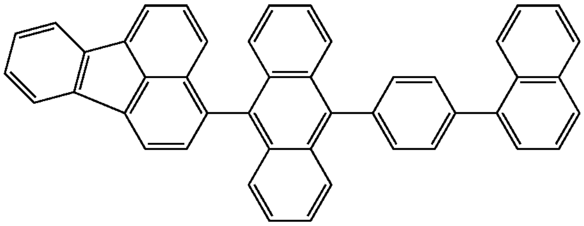
2a′-85
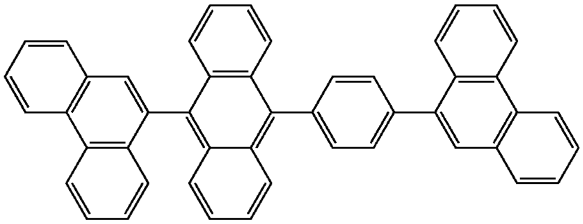
2a′-86
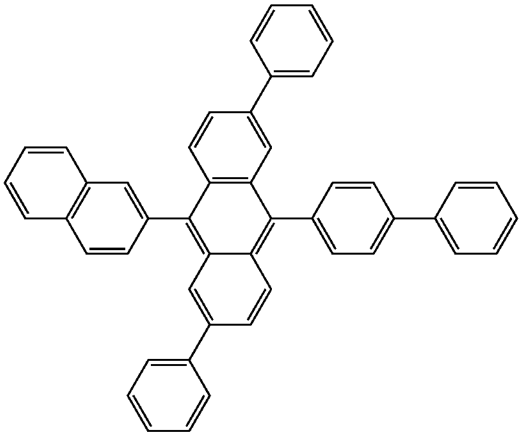
2a′-87
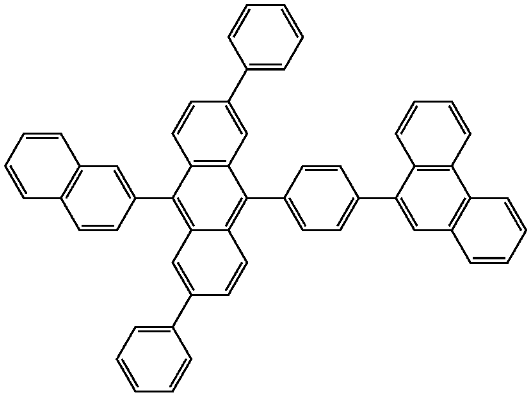
2a′-88
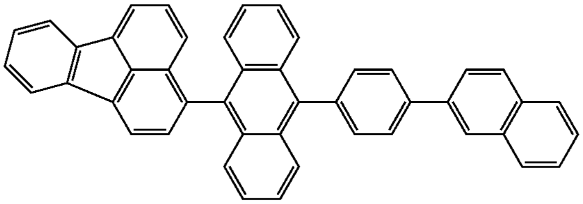
2a′-89
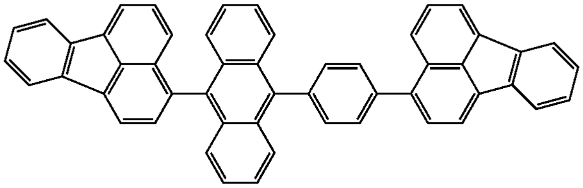
2a′-90
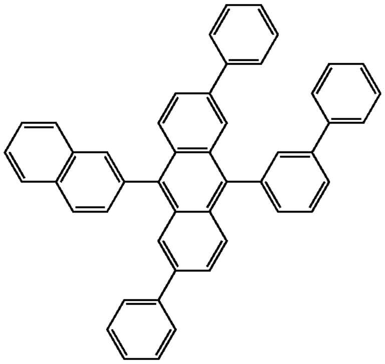

-continued
2a′-91
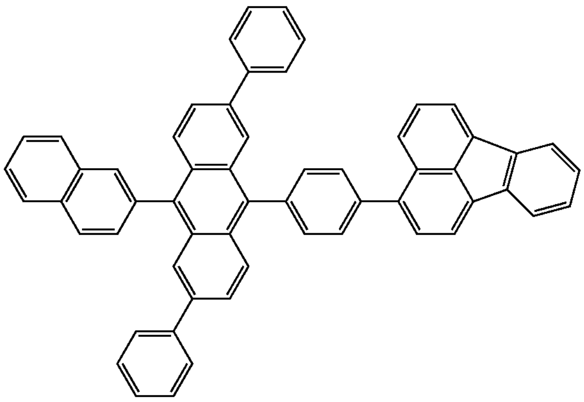
2a′-92
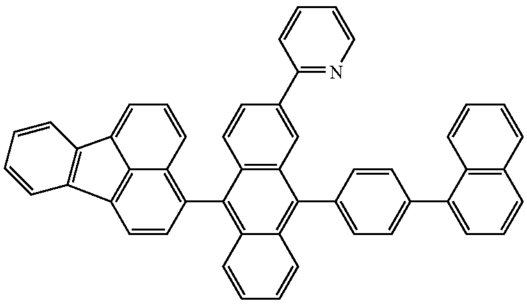
2a′-93
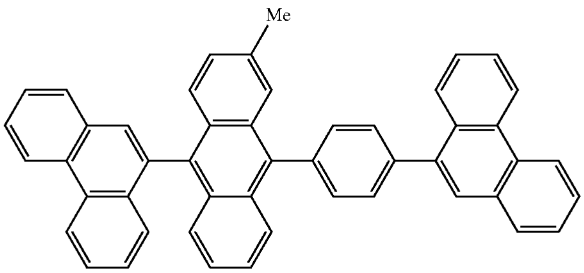
2a′-94
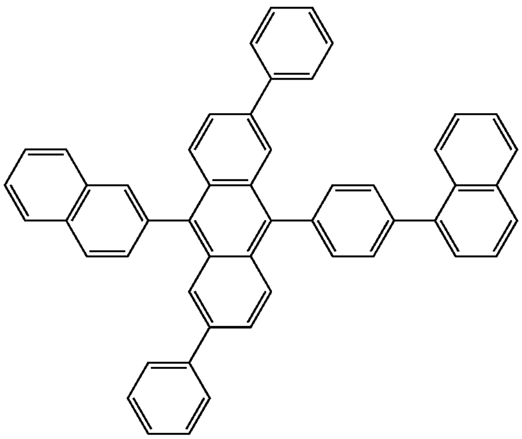
2a′-95
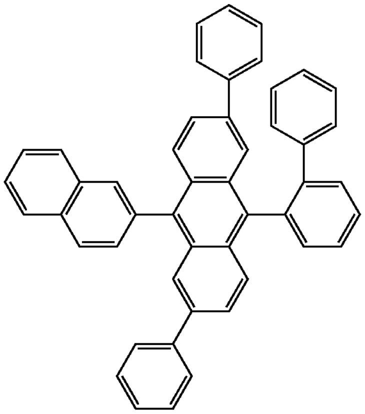
2a′-96
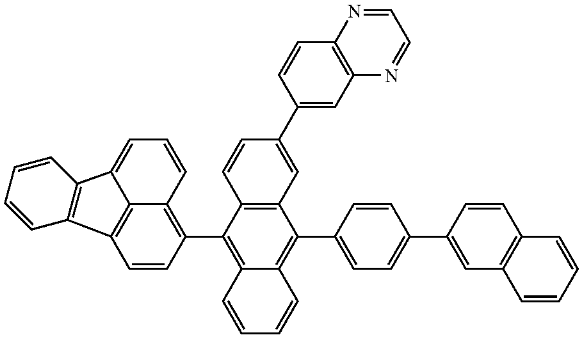

-continued
2a′-97
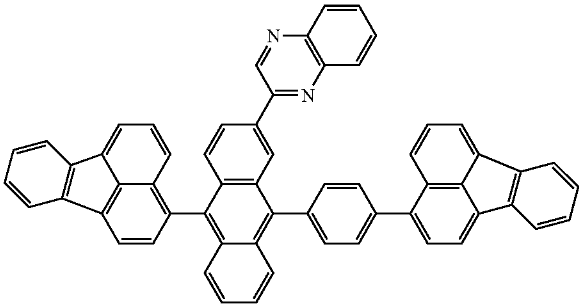
2a′-98
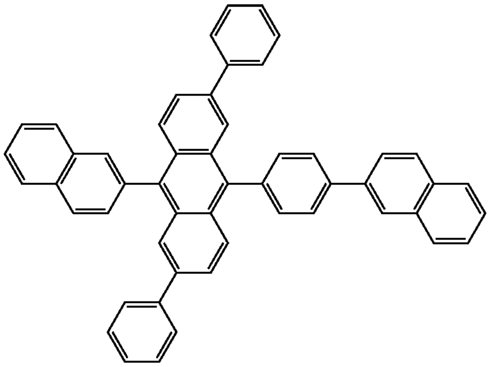
2a′-99
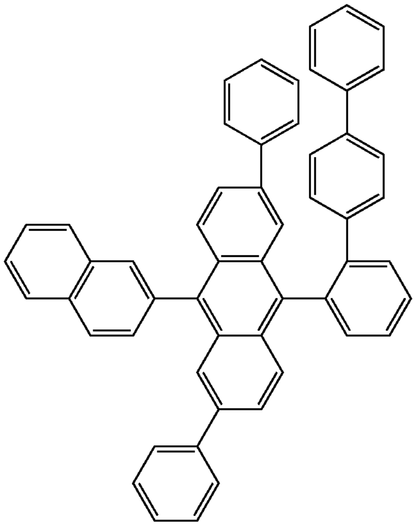
2a′-100
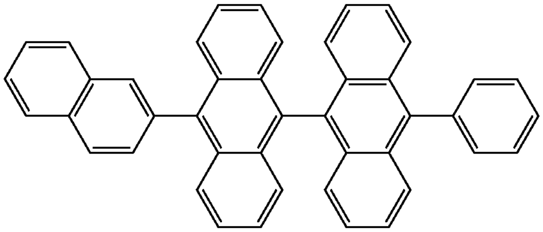
2a′-101
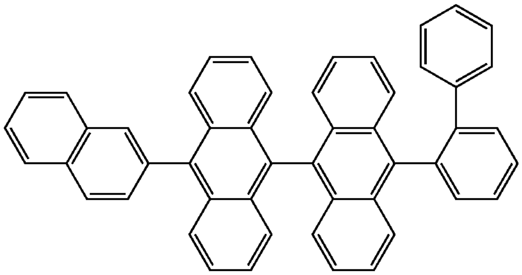
2a′-102
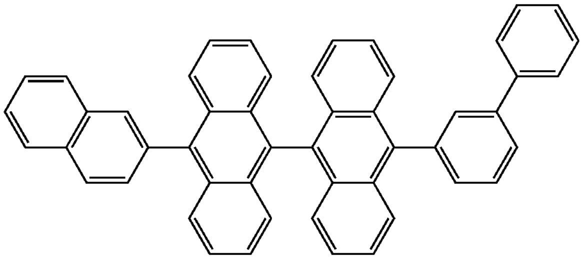
2a′-103
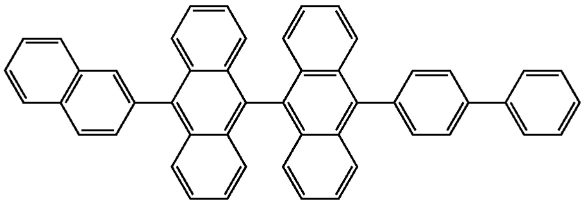
2a′-104
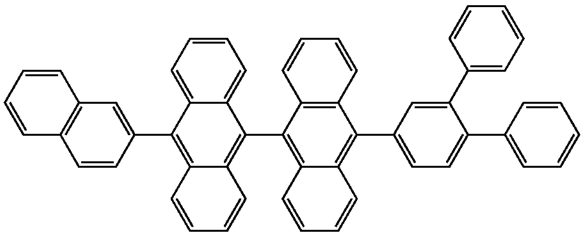

-continued
2a′-105
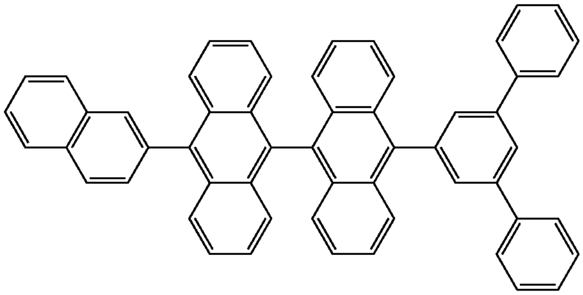
2a′-106
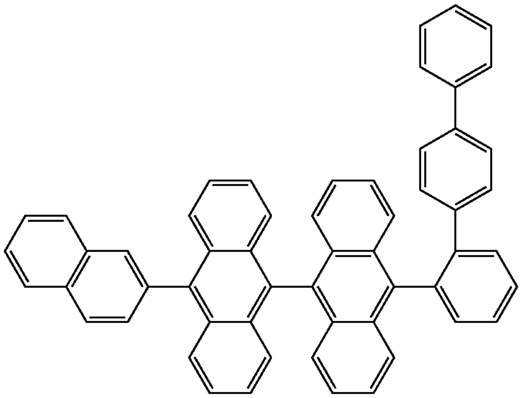
2a′-107
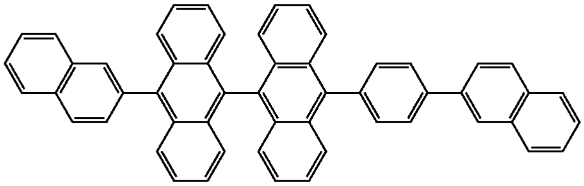
2a′-108
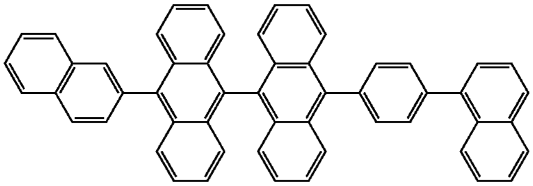
2a′-109
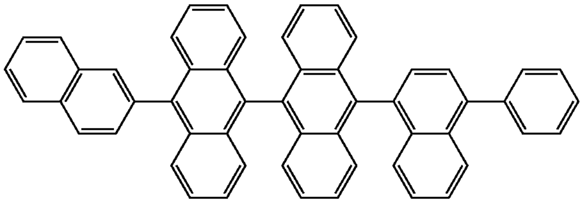
2a′-110
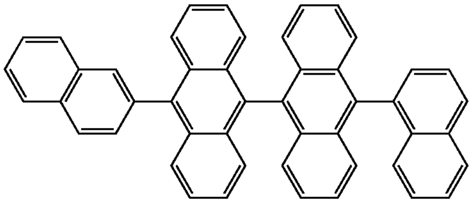
2a′-111
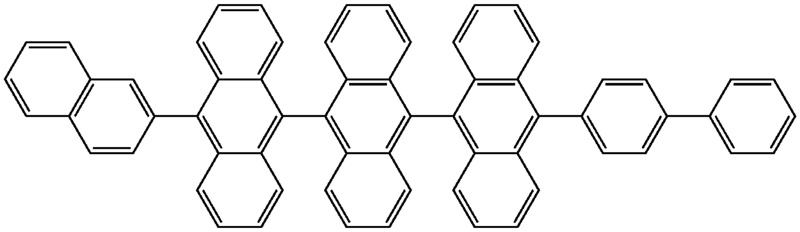
2a′-112
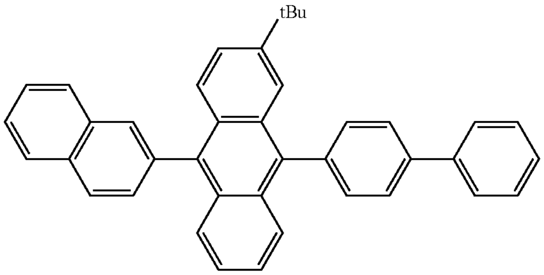
2a′-113
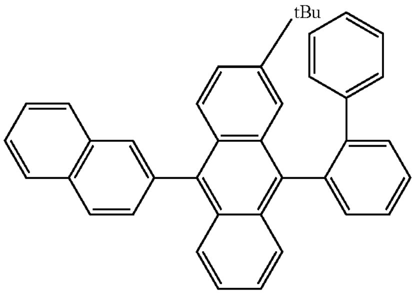

-continued
2a'-114
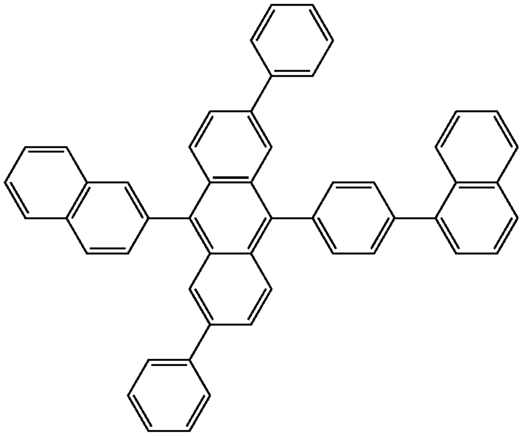
2a'-115
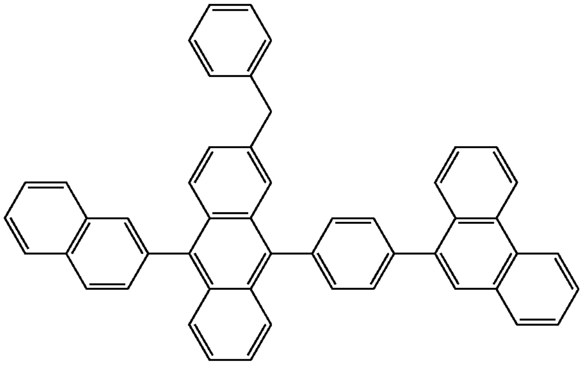
2a'-116
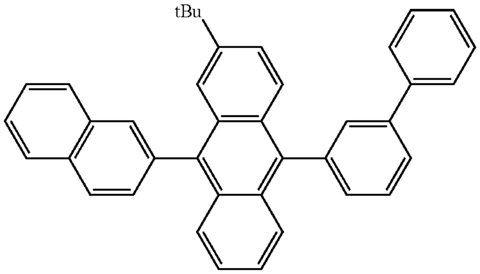
2a'-117
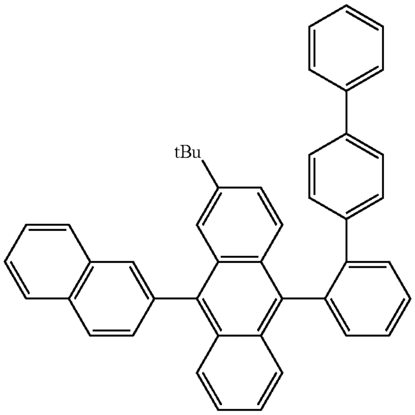
2a'-118
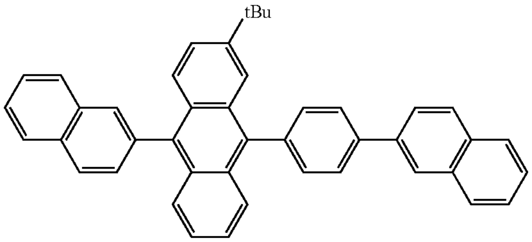
2a'-119
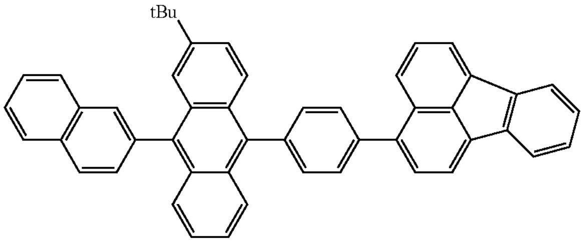
2a'-120
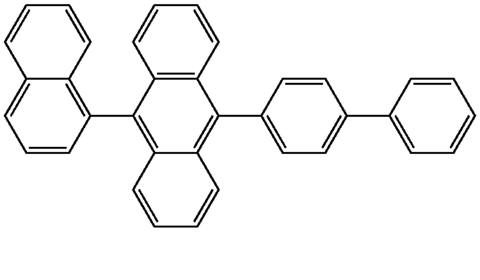
2a'-121
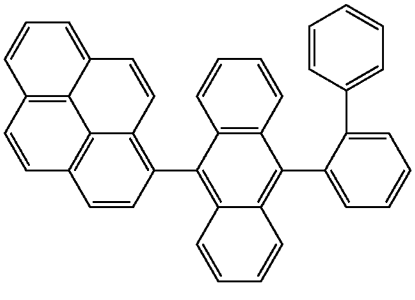

-continued
2a′-122
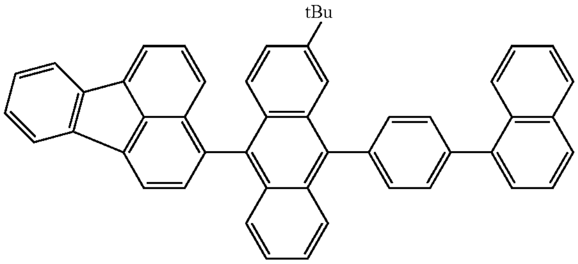
2a′-123
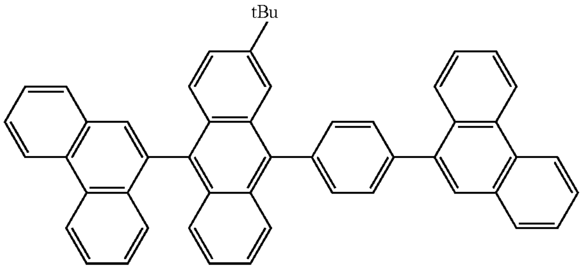
2a′-124
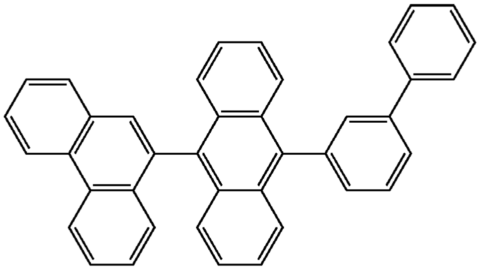
2a′-125
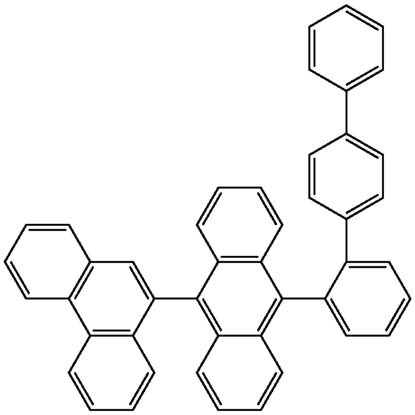
2a′-126
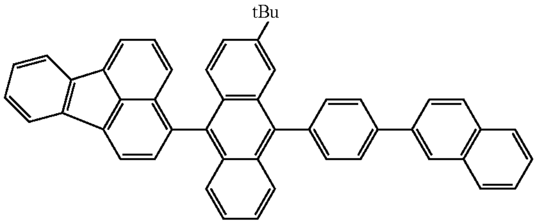
2a′-127
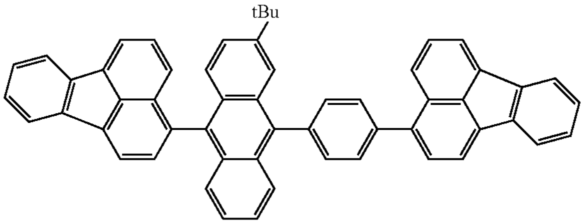
2a′-128
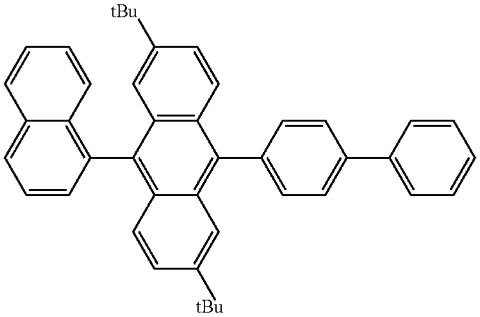
2a′-129
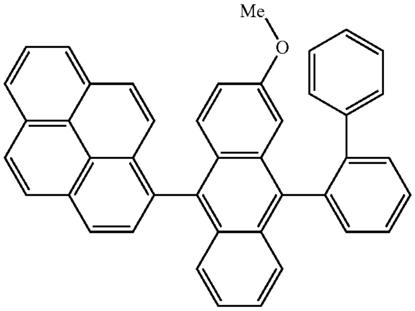
2a′-130
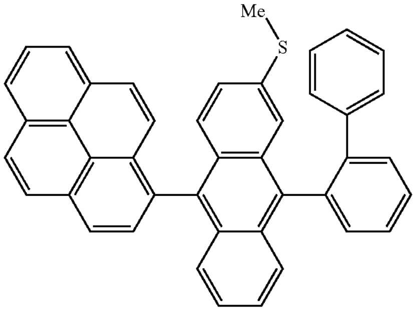
2a′-131
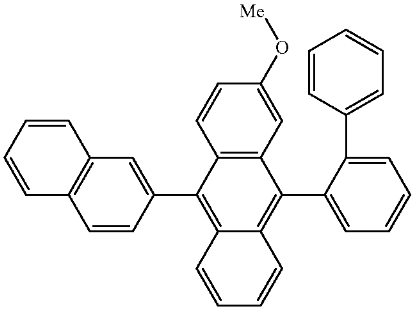

-continued
2a'-132
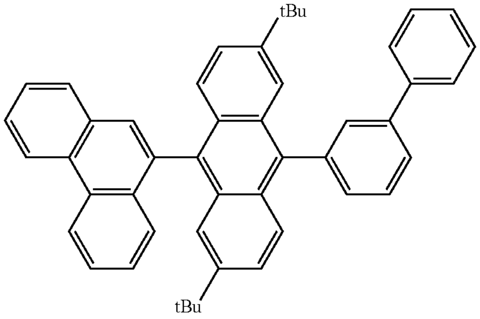
2a'-133
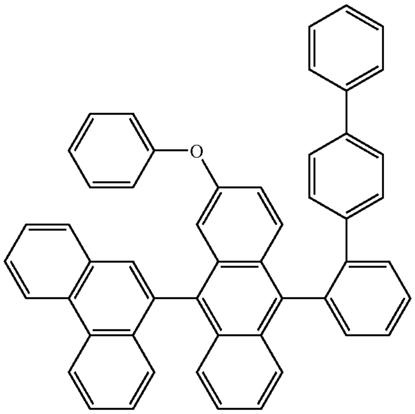
2a'-134
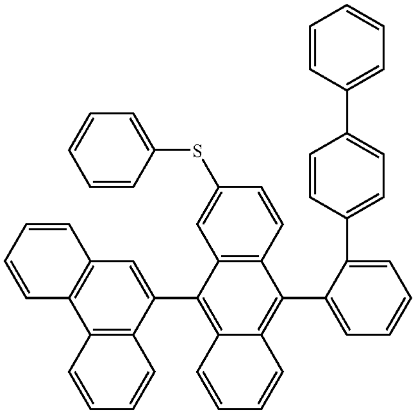
2a'-135
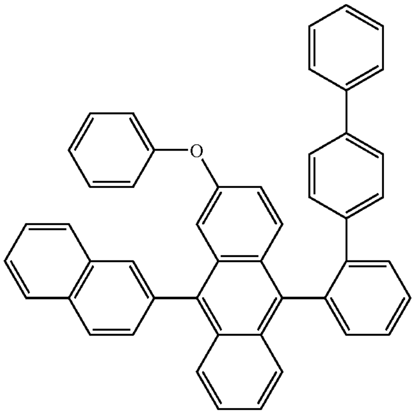
2a'-136
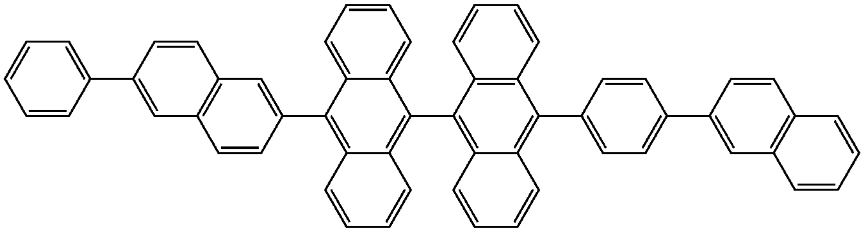
2a'-137
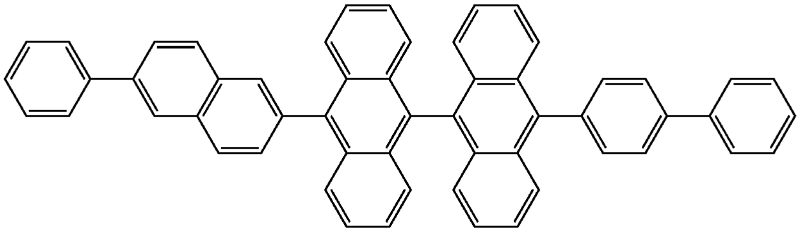
2a'-138
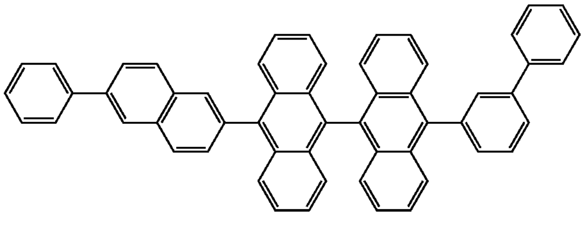
2a'-139
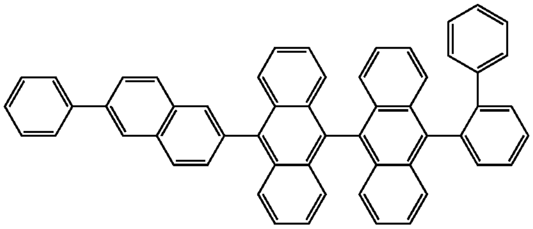

-continued
2a′-140
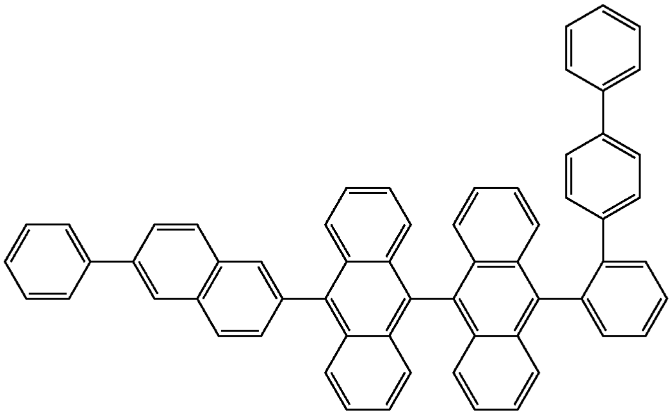
2a′-141
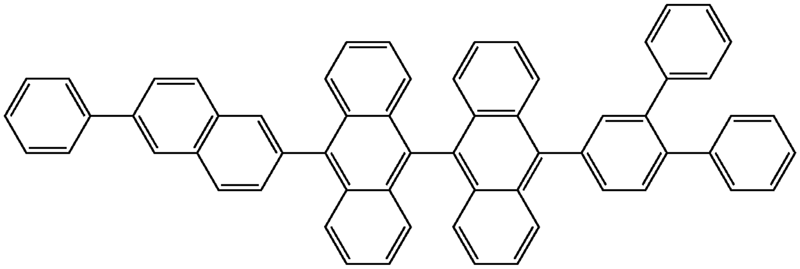
2a′-142
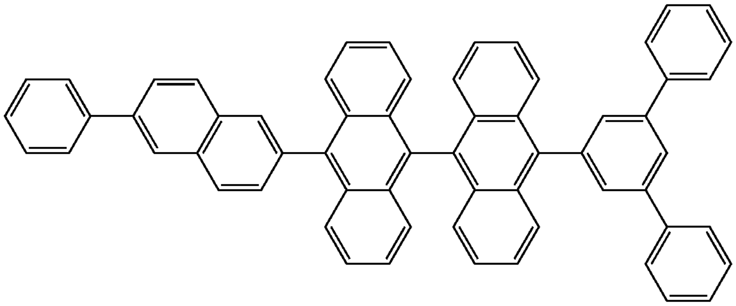
2a′-143
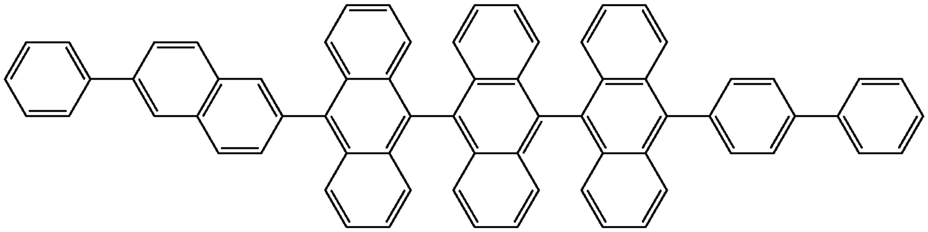

In addition, the fluoranthene compound of the present invention represented by the general formula (1) is preferably used in combination with a compound represented by the following general formula (2b), when the former is used as a light-emitting material:

(2b)

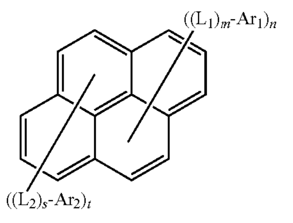

In the general formula (2b), $Ar_1$ and $Ar_2$ each independently represent a substituted or unsubstituted aryl group whose nucleic carbon atom number ranges from 6 to 50.

$L_1$ and $L_2$ each independently represent a member selected from the group consisting of substituted or unsubstituted phenylene groups, substituted or unsubstituted naphthalenylene groups, substituted or unsubstituted fluorenylene groups and substituted or unsubstituted dibenzo-silolylene groups.

In Formula (2b), m is an integer ranging from 0 to 2, n an integer ranging from 1 to 4, s an integer ranging from 0 to 2, and t an integer ranging from 0 to 4.

Moreover, the group $L_1$ or $Ar_1$ is bonded to any one of the positions 1 to 5 on the pyrene nuclei, while the group $L_2$ or $Ar_2$ is bonded to any one of the positions 6 to 10 on the pyrene nuclei.

The aryl group whose nucleic carbon atom number ranges from 6 to 50 of $Ar_1$ and $Ar_2$ in the general formula (2b) includes phenyl, 1-naphthyl, 2-naphthyl, 1-anthryl, 2-anthryl, 9-anthryl, 9-(10-phenyl) anthryl, 9-(10-naphthyl-1-yl) anthryl, 9-(10-naphthyl-2-yl) anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, 3-methyl-2-naphthyl, 4-methyl-1-naphthyl and 4-methyl-1-anthryl groups. An aryl group whose nucleic carbon atom number ranges from 6 to 16 is preferred and specifically, phenyl, 1-naphthyl, 2-naphthyl, 9-(10-phenyl) anthryl, 9-(10-naphthyl-1-yl) anthryl, 9-(10-naphthyl-2-yl) anthryl, 9-phenanthryl, 1-pyrenyl, 2-pyrenyl, 4-pyrenyl, 2-biphenylyl, 3-biphenylyl, 4-biphenylyl, o-tolyl, m-tolyl, p-tolyl and p-t-butylphenyl groups are preferred.

Said aryl group may have a substituent, which includes alkyl groups (such as methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl and 2-norbornyl groups), alkoxy groups having 1 to 6 carbon (such as ethoxy, methoxy, i-propoxy, n-propoxy, s-butoxy, t-butoxy, pentoxy, hexyloxy, cyclopentoxy and cyclohexyloxy groups), aryl groups whose nucleic carbon atom number ranges from 5 to 40, amino groups having an aryl group whose nucleic carbon atom number ranges from 5 to 40, ester groups having an aryl group whose nucleic carbon atom number ranges from 5 to 40, ester groups having an alkyl group having 1 to 6 carbon atoms, a cyano group, a nitro group and halogen atoms.

In the general formula (2b), each of the groups $L_1$ and $L_2$ preferably represents a member selected from the group consisting of substituted or unsubstituted phenylene groups, and substituted or unsubstituted fluorenylene groups.

Moreover, the substituents for the foregoing groups $L_1$ and $L_2$ may be those listed above in connection with the foregoing aromatic rings.

In Formula (2b), m is preferably an integer ranging from 0 to 1. In Formula (2b), n is preferably an integer ranging from 1 to 2. In Formula (2b), s is preferably an integer ranging from 0 to 1. In Formula (2b), t is preferably an integer ranging from 0 to 2.

Specific examples of the pyrene derivatives represented by the general formula (2b) and used for forming the organic EL element of the present invention are unsymmetrical pyrene derivatives such as those described in Sections [0020] to [0023] appearing in International Patent Publication No. 2005/115950, Pamphlet. In addition to these unsymmetrical pyrene derivatives, it is also possible to use symmetrical pyrene derivatives as materials for forming the organic EL element according to the present invention. Typical examples thereof will be listed below:

2b-1

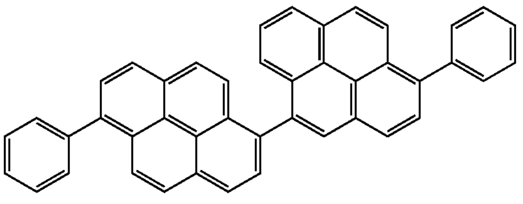

2b-2

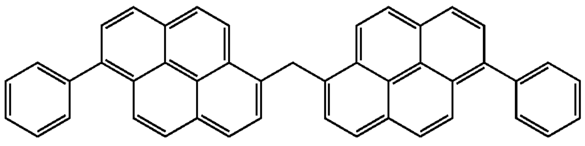

-continued
2b-3
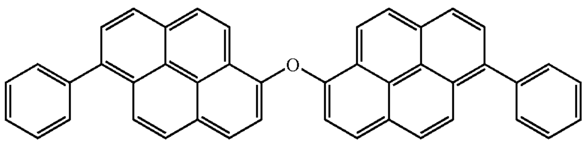
2b-4
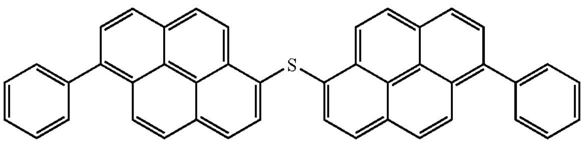
2b-5
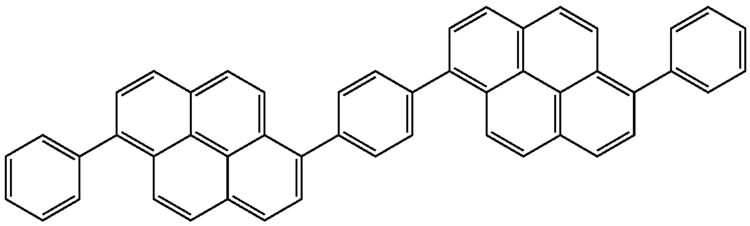
2b-6
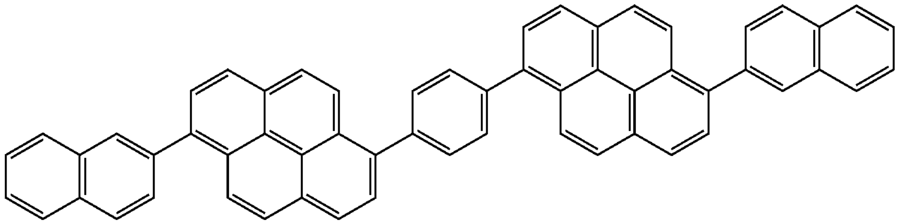
2b-7
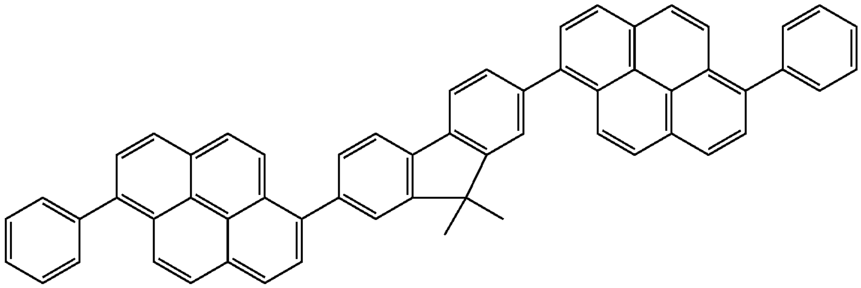
2b-8
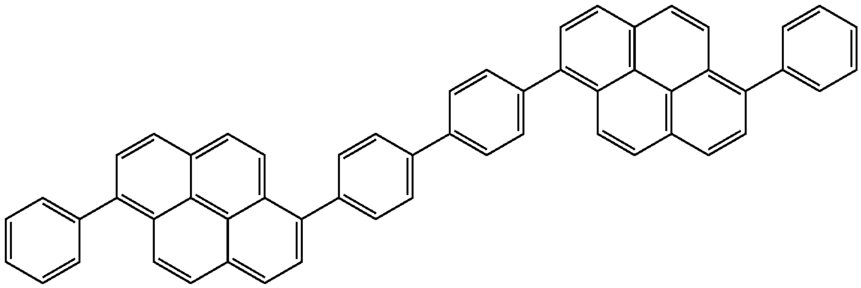
2b-9
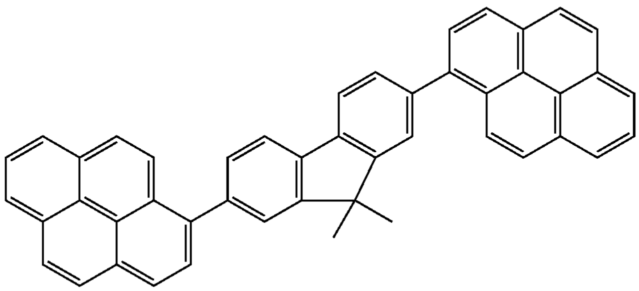

-continued
2b-10
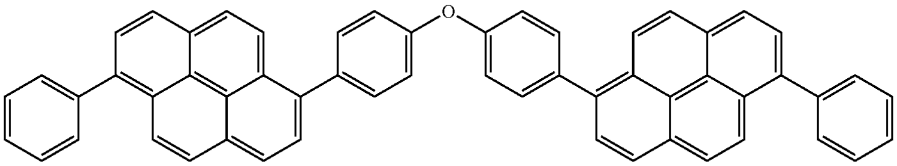
2b-11
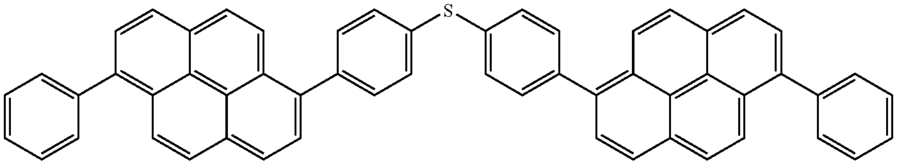
2b-12
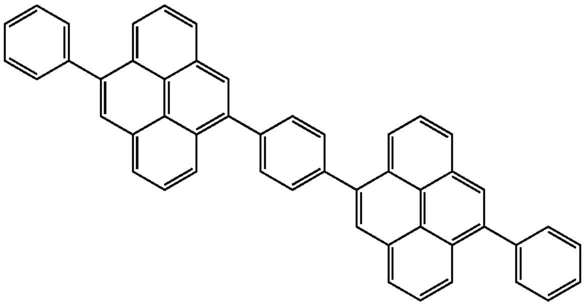
2b-13
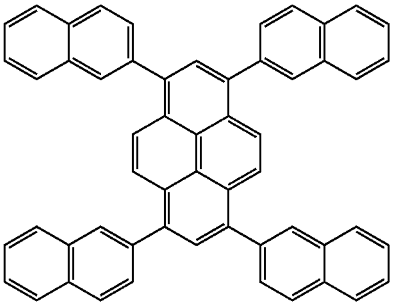
2b-14
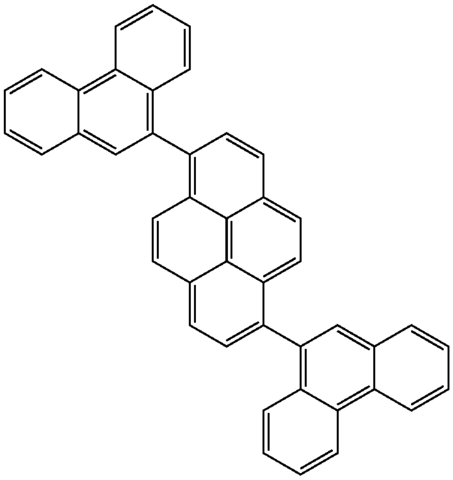
2b-15
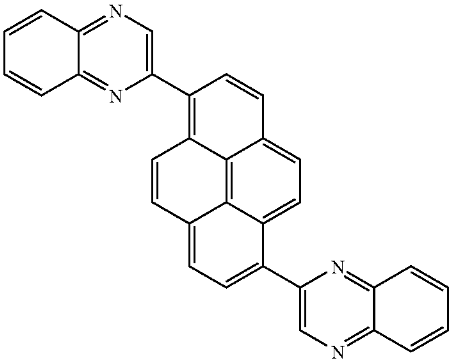
2b-16
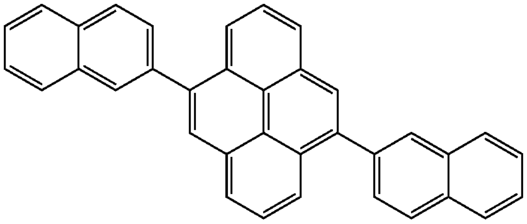
2b-17
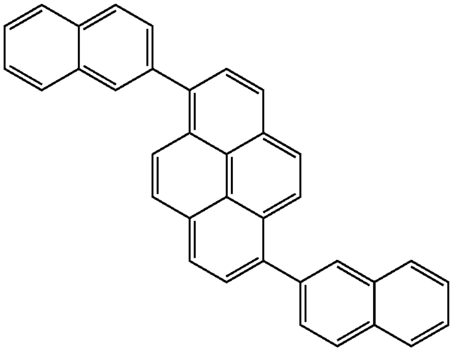

-continued
2b-18
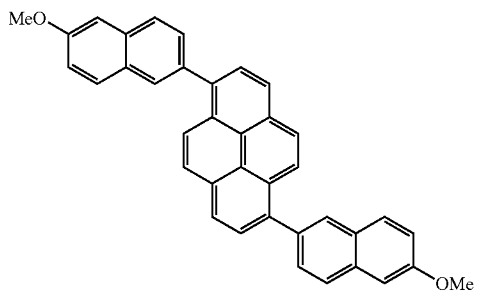
2b-19
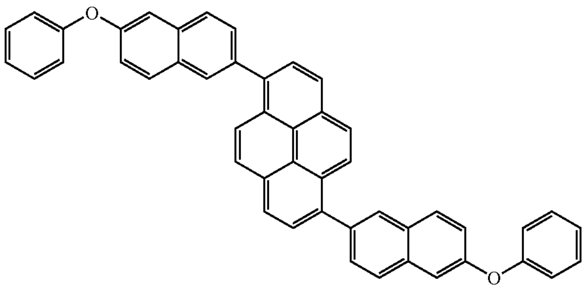
2b-20
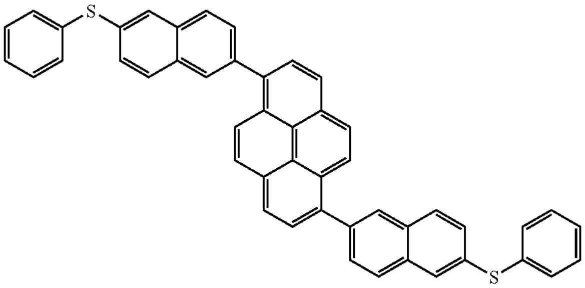
2b-21
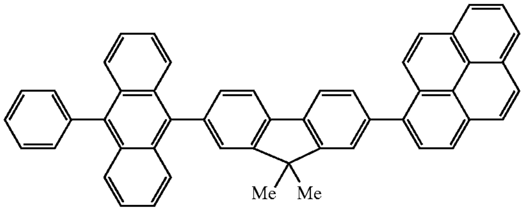
2b-22
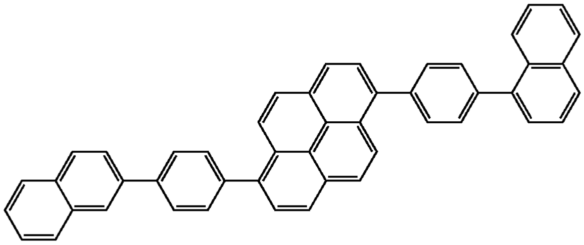
2b-23
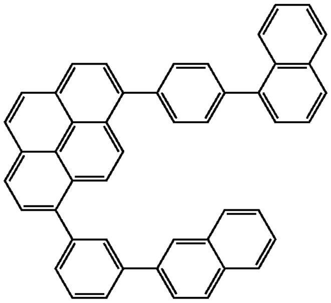
2b-24
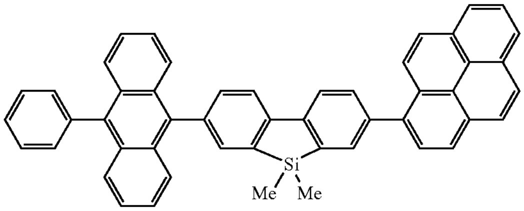
2b-25
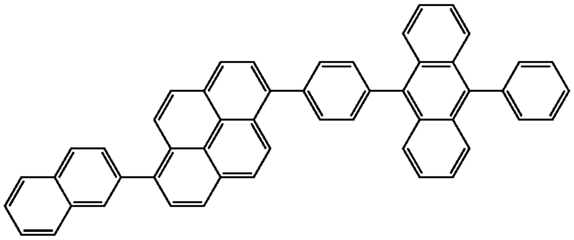

-continued
2b-26
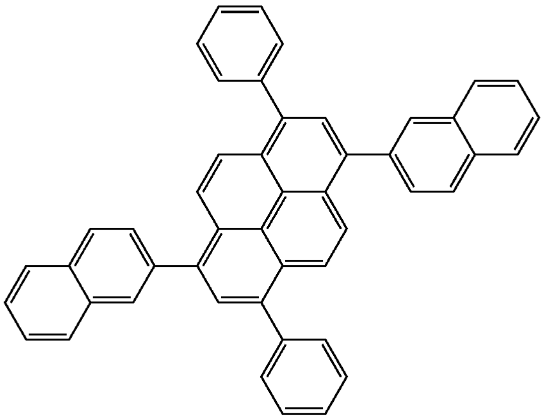
2b-27
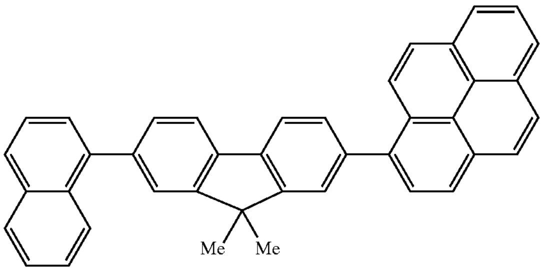
2b-28
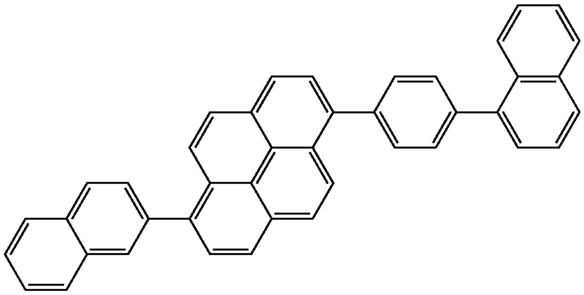
2b-29
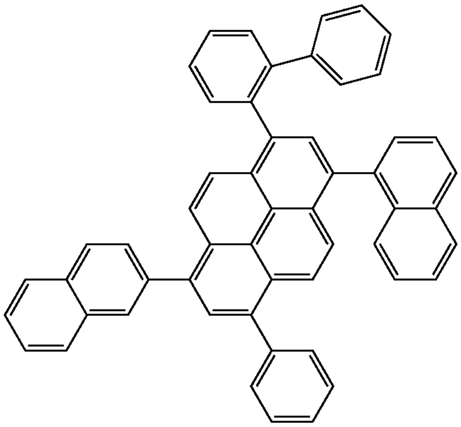
2b-30
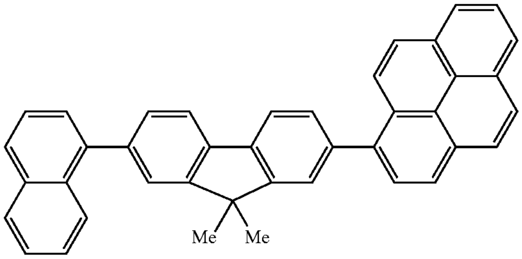
2b-31
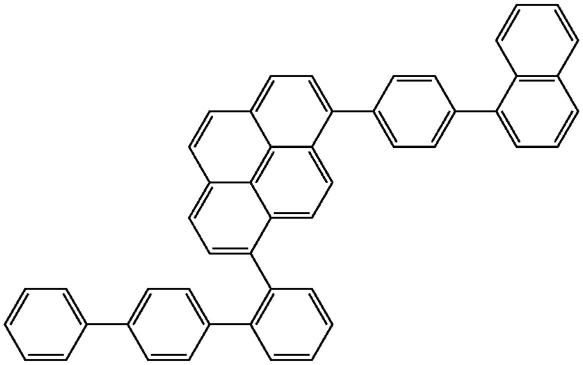

-continued
2b-32
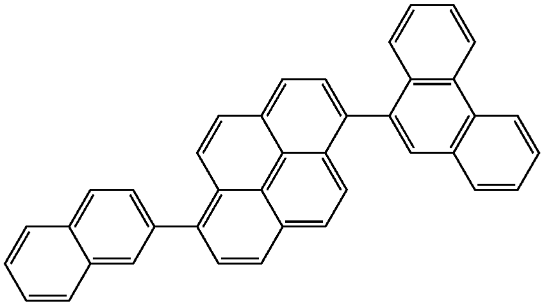
2b-33
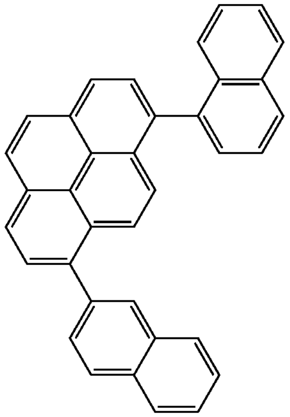
2b-34
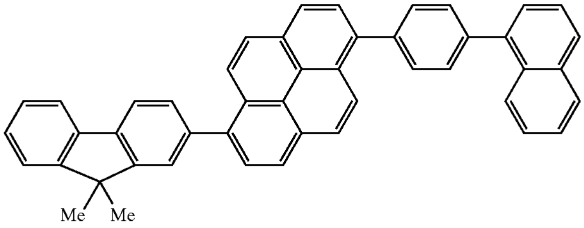
2b-35
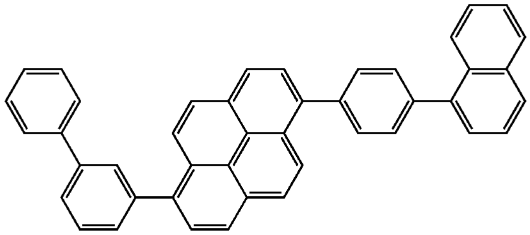
2b-36
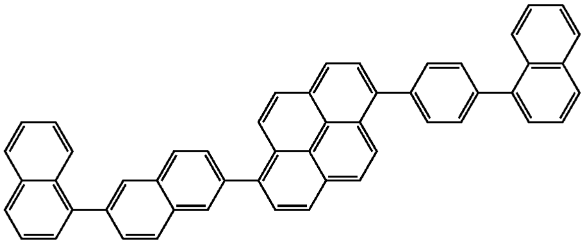
2b-37
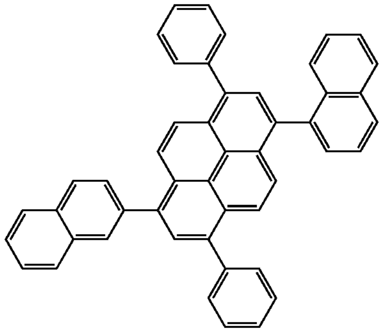
2b-38
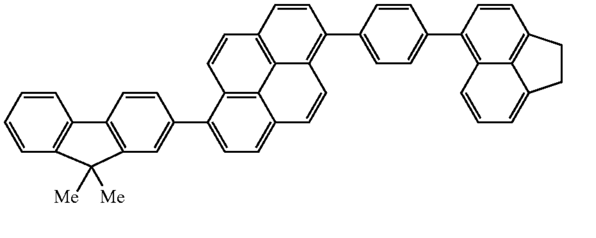
2b-39
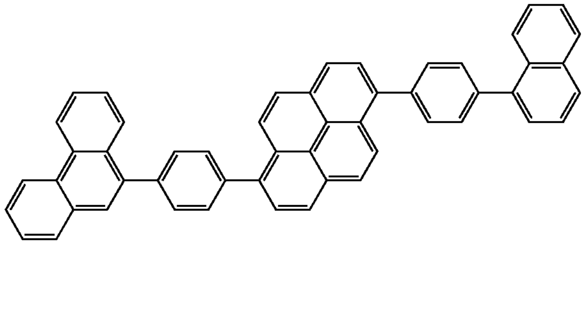

-continued 2b-40

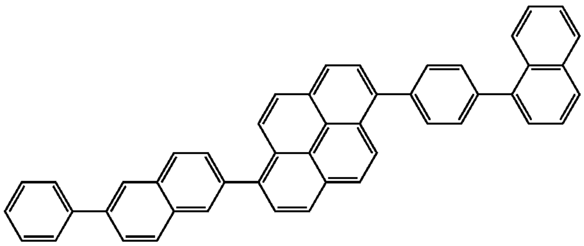

2b-41

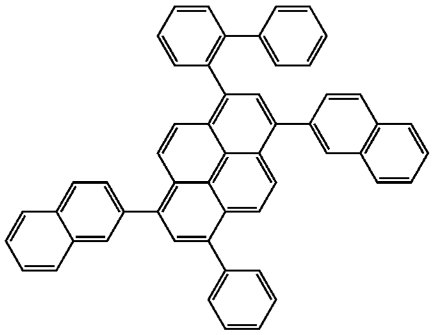

2b-42

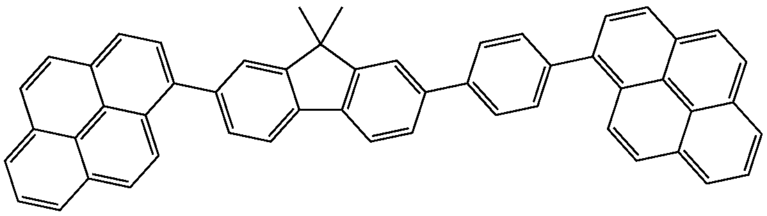

In addition, the fluoranthene compound of the present invention represented by the general formula (1) is preferably used in combination with a compound represented by the following general formula (2c), when the former is used as a light-emitting material:

(2c)

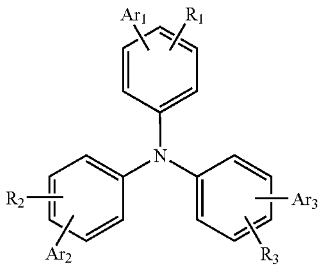

In the general formula (2c), $Ar_1$, $Ar_2$ and $Ar_3$ each independently represent a member selected from the group consisting of anthracene structure-containing groups, phenanthrene structure-containing groups, pyrene structure-containing groups and perylene structure-containing groups.

In the general formula (2c), $R_1$, $R_2$ and $R_3$ each independently represent a hydrogen atom or a substituent.

In the general formula (2c), $Ar_1$, $Ar_2$ and $Ar_3$ each independently represent a member preferably selected from the group consisting of substituted or unsubstituted anthryl-phenyl groups, anthryl groups, phenanthrenyl groups, perylenyl groups, and pyrenyl groups, more preferably selected from the group consisting of alkyl-substituted or unsubstituted anthryl-phenyl groups, phenanthryl groups and pyrenyl groups and most preferably selected from the group consisting of pyrenyl groups and phenanthryl groups.

The substituents $R_1$, $R_2$ and $R_3$ appearing in the general formula (2c) each independently represent an alkyl group (preferably one having 1 to 30, more preferably 1 to 20 and particularly preferably 1 to 10 carbon atoms, such as methyl, ethyl, isopropyl, t-butyl, n-octyl, n-decyl, n-hexadecyl, cyclopropyl, cyclopentyl or cyclohexyl group); an alkenyl group (preferably one having 2 to 30, more preferably 2 to 20 and particularly preferably 2 to 10 carbon atoms, such as vinyl, allyl, 2-butenyl or 3-pentenyl group); an alkynyl group (preferably one having 2 to 30, more preferably 2 to 20 and particularly preferably 2 to 10 carbon atoms, such as propargyl, or 3-pentynyl group); an aryl group (preferably one having 6 to 30, more preferably 6 to 20 and particularly preferably 6 to 12 carbon atoms, such as phenyl, p-methylphenyl, naphthyl or anthranyl group); an amino group (preferably one having 0 to 30, more preferably 0 to 20 and particularly preferably 0 to 10 carbon atoms, such as amino, methylamino, dimethylamino, diethylamino, dibenzylamino, diphenylamino or ditolyl-amino group); an alkoxy group (preferably one having 1 to 30, more preferably 1 to 20 and particularly preferably 1 to 10 carbon atoms, such as methoxy, ethoxy, butoxy or 2-ethylhexyloxy group); an aryloxy group (preferably one having 6 to 30, more preferably 6 to 20 and particularly preferably 6 to 12 carbon atoms, such as phenyloxy, 1-naphthyloxy, or 2-naphthyloxy group); a hetero-aryloxy group (preferably one having 1 to 30, more preferably 1 to 20 and particularly preferably 1 to 12 carbon atoms, such as pyridyloxy, pyrazyloxy, pyrimidyloxy, or quinolyloxy group); an acyl group (preferably one having 1 to 30, more preferably 1 to 20 and particularly preferably 1 to 12 carbon atoms, such as acetyl, benzoyl, formyl or pivaloyl group); an alkoxycarbonyl group (preferably one having 2 to 30, more preferably 2 to 20 and particularly preferably 2 to 12 carbon atoms, such as methoxy-carbonyl or ethoxy-carbonyl group); an aryloxycarbonyl group (preferably one having 7 to 30, more preferably 7 to 20 and particularly preferably 7 to 12 carbon atoms, such as phenyloxy-carbonyl group); an acyloxy group (preferably one having 2 to 30, more preferably 2 to 20 and particularly preferably 2 to 10 carbon atoms, such as acetoxy or benzoyloxy group); an acylamino group (preferably one having 2 to 30, more preferably 2 to 20 and particularly preferably 2 to 10 carbon atoms, such as acetylamino or benzoylamino group); an alkoxy-carbonylamino group (preferably one having 2 to 30, more preferably 2 to 20 and particularly preferably 2 to 12 carbon atoms, such as methoxy-carbonylamino group); an aryloxy-carbonylamino group (preferably one having 7 to 30, more preferably 7 to 20 and particularly preferably 7 to 12 carbon atoms, such as phenyloxy-carbonylamino group); a sulfonylamino group (preferably one having 1 to 30, more preferably 1 to 20 and particularly preferably 1 to 12 carbon atoms, such as methane-sulfonylamino, or benzene-sulfonylamino group); a sulfamoyl group (preferably one having 0 to 30, more preferably 0 to 20 and particularly preferably 0 to 12 carbon atoms, such as sulfamoyl, methyl-sulfamoyl, dimethyl-sulfamoyl, or phenyl-sulfamoyl group); a carbamoyl group (preferably one having 1 to 30, more preferably 1 to 20 and particularly preferably 1 to 12 carbon atoms, such as carbamoyl, methyl-carbamoyl, diethyl-carbamoyl, or phenyl-carbamoyl group); an alkylthio group (preferably one having 1 to 30, more preferably 1 to 20 and particularly preferably 1 to 12 carbon atoms, such as methylthio or ethylthio group); an arylthio group (preferably one having 6 to 30, more preferably 6 to 20 and particularly preferably 6 to 12 carbon atoms, such as phenylthio group); a hetero-arylthio group (preferably one having 1 to 30, more preferably 1 to 20 and particularly preferably 1 to 12 carbon atoms, such as pyridylthio, 2-benzimidazolyl-thio, 2-benzoxazolylthio or 2-benzothiazolylthio group); a sulfonyl group (preferably one having 1 to 30, more preferably 1 to 20 and particularly preferably 1 to 12 carbon atoms, such as mesyl or tosyl group); a sulfinyl group (preferably one having 1 to 30, more preferably 1 to 20 and particularly preferably 1 to 12 carbon atoms, such as methane-sulfinyl, or benzene-sulfinyl group); an ureido group (preferably one having 1 to 30, more preferably 1 to 20 and particularly preferably 1 to 12 carbon atoms, such as ureido, methyl-ureido, or phenyl-ureido group); a phosphoric acid amide group (preferably one having 1 to 30, more preferably 1 to 20 and particularly preferably 1 to 12 carbon atoms, such as diethyl-phosphoric acid amide or phenyl-phosphoric acid amide group); a hydroxyl group, a mercapto group, a halogen atom (such as a fluorine, chlorine, bromine or iodine atom); a cyano group, a sulfo group, a carboxyl group, a nitro group, a hydroxamic acid residue, a sulfino group, a hydrazino group, an imino group, a heterocyclic group (preferably one having 1 to 30, more preferably 1 to 12 carbon atoms containing a hetero atom selected from, for instance, nitrogen, oxygen, sulfur atoms and mixture thereof, such as imidazolyl, pyridyl, quinolyl, furyl, thienyl, piperidyl, morpholino, benzoxazolyl, benzimidazolyl, or benzothiazolyl group); or a silyl group (preferably one having 3 to 40, more preferably 3 to 30 and particularly preferably 3 to 24 carbon atoms, such as trimethyl-silyl, or triphenyl-silyl group). These substituents may further have a substituent.

Each of the substituents $R_1$, $R_2$ and $R_3$ appearing in the general formula (2c) is preferably selected from the group consisting of alkyl groups and aryl groups.

Specific examples of the amine derivatives represented by the general formula (2c) which can be used in the organic EL element according to the present invention include a variety of known ones such as those disclosed in J.P. KOKAI 2002-324678 (see, the passages included in Sections [0079] to [0083]). Typical examples thereof will be listed below:

2c-1

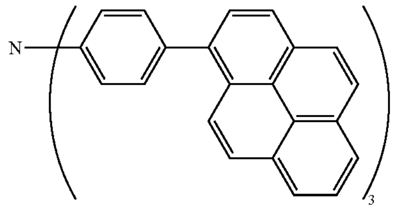

2c-2

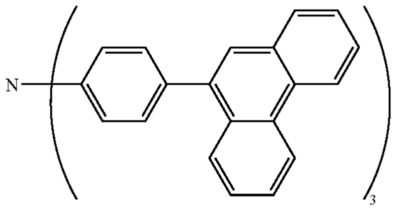

2c-3

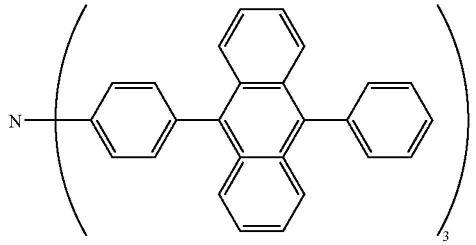

2c-4

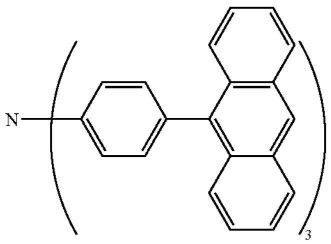

2c-5

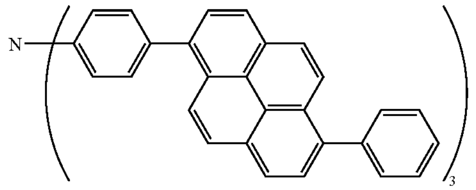

2c-6

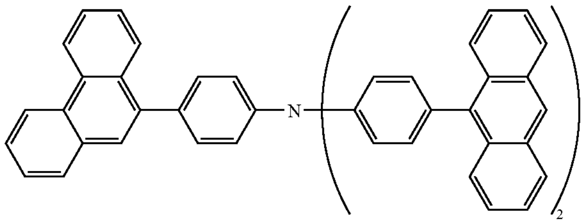

-continued
2c-7
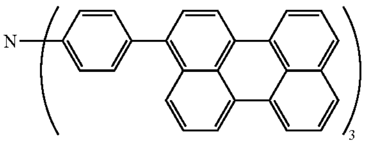
2c-8
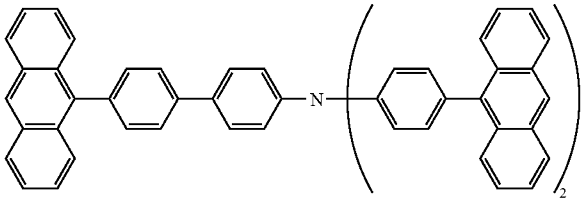
2c-9
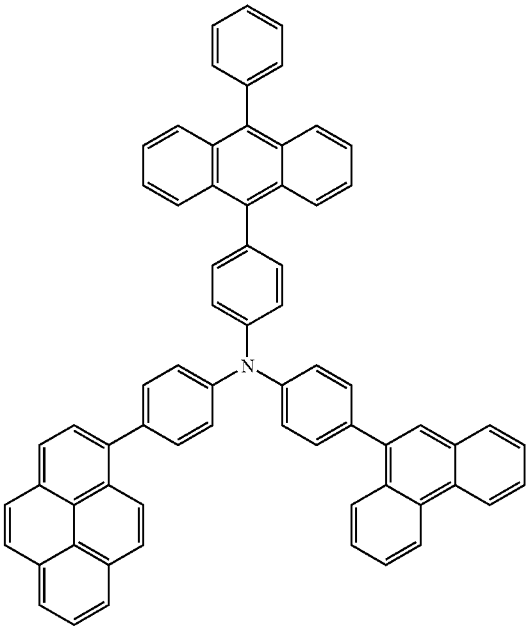
2c-10
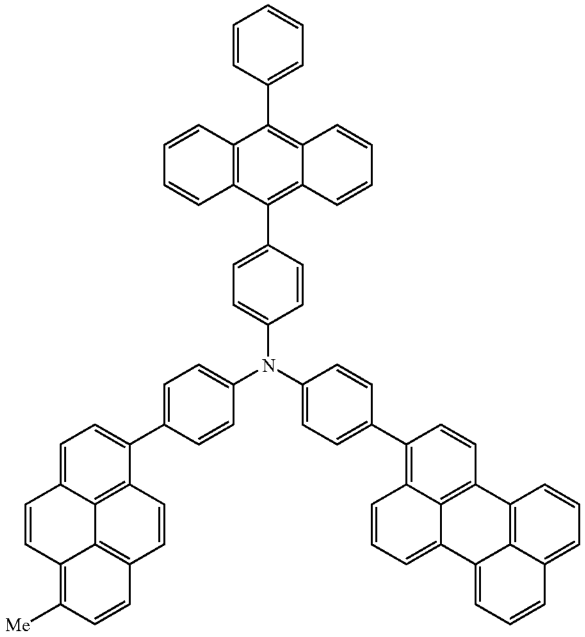
2c-11
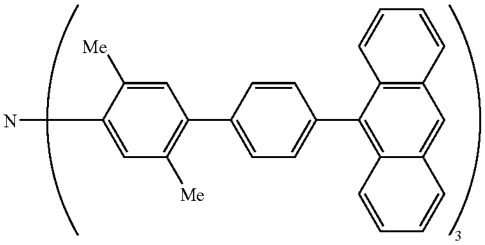
2c-12
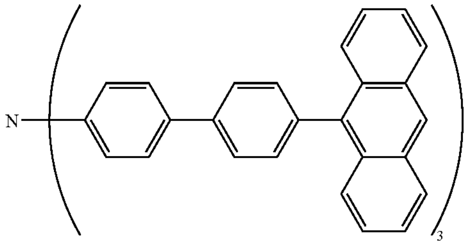
2c-13
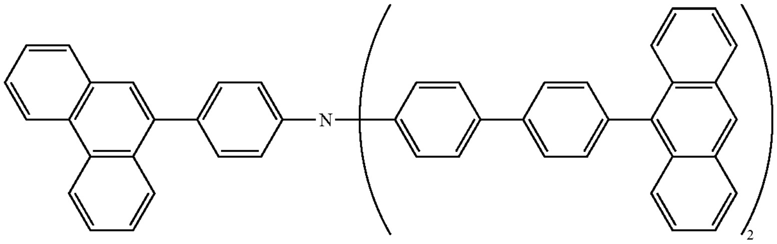

In addition, the fluoranthene compound of the present invention represented by the foregoing general formula (1) is preferably used in combination with a compound represented by the following general formula (2d), when the former is used as a light-emitting material:

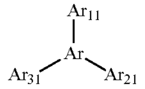

(2d)

In the general formula (2d), $Ar_{11}$, $Ar_{21}$ and $Ar_{31}$ each independently represent an aryl group whose nucleic carbon atom number ranges from 6 to 50. The aryl group may have at least one substituent.

At least one of the groups $Ar_{11}$, $Ar_{21}$, $Ar_{31}$ and the substituents present on the foregoing aryl groups represented by these groups $Ar_{11}$, $Ar_{21}$ and $Ar_{31}$ has a fused aryl ring structure having a nucleic carbon atom number ranging from 10 to 20 or a fused heteroaryl ring structure having a nucleic carbon atom number ranging from 6 to 20.

The group Ar represents a trivalent group derived from an aromatic or heteroaromatic ring.

The aryl group, whose nucleic carbon atom number ranges from 6 to 50, represented by the foregoing groups $Ar_{11}$, $Ar_{21}$ and $Ar_{31}$ appearing in Formula (2d) is preferably one having a nucleic carbon atom number ranging from 6 to 30, more preferably 6 to 20 and further preferably 6 to 16. Examples of such aryl groups are phenyl, naphthyl, anthryl, phenanthrenyl, pyrenyl, perylenyl, fluorenyl, biphenylyl, terphenylyl, rubrenyl, chrysenyl, triphenylenyl, benzanthryl, benzphenanthrenyl, and diphenyl-anthryl groups and these aryl groups may further have substituents.

Examples of the substituents present on the aryl rings are alkyl groups (preferably those each having 1 to 30, more preferably 1 to 20 and particularly preferably 1 to 10 carbon atoms, such as methyl, ethyl, isopropyl, t-butyl, n-octyl, n-decyl, n-hexadecyl, cyclopropyl, cyclopentyl and cyclohexyl groups); alkenyl groups (preferably those each having 2 to 30, more preferably 2 to 20 and particularly preferably 2 to 10 carbon atoms, such as vinyl, allyl, 2-butenyl and 3-pentenyl groups); alkynyl groups (preferably those each having 2 to 30, more preferably 2 to 20 and particularly preferably 2 to 10 carbon atoms, such as propargyl, and 3-pentynyl groups); aryl groups (preferably those each having 6 to 30, more preferably 6 to 20 and particularly preferably 6 to 12 carbon atoms, such as phenyl, p-methylphenyl, naphthyl and anthranyl groups); amino groups (preferably those each having 0 to 30, more preferably 0 to 20 and particularly preferably 0 to 10 carbon atoms, such as amino, methylamino, dimethylamino, diethylamino, dibenzylamino, diphenylamino and ditolyl-amino groups); alkoxy groups (preferably those each having 1 to 30, more preferably 1 to 20 and particularly preferably 1 to 10 carbon atoms, such as methoxy, ethoxy, butoxy and 2-ethylhexyloxy groups); aryloxy groups (preferably those each having 6 to 30, more preferably 6 to 20 and particularly preferably 6 to 12 carbon atoms, such as phenyloxy, 1-naphthyloxy, and 2-naphthyloxy groups); hetero-aryloxy groups (preferably one having 1 to 30, more preferably 1 to 20 and particularly preferably 1 to 12 carbon atoms, such as pyridyloxy, pyrazyloxy, pyrimidyloxy, and quinolyloxy groups); acyl groups (preferably those each having 1 to 30, more preferably 1 to 20 and particularly preferably 1 to 12 carbon atoms, such as acetyl, benzoyl, formyl and pivaloyl groups); alkoxycarbonyl groups (preferably those each having 2 to 30, more preferably 2 to 20 and particularly preferably 2 to 12 carbon atoms, such as methoxy-carbonyl and ethoxy-carbonyl groups); aryloxycarbonyl groups (preferably those each having 7 to 30, more preferably 7 to 20 and particularly preferably 7 to 12 carbon atoms, such as phenyloxy-carbonyl group); acyloxy groups (preferably those each having 2 to 30, more preferably 2 to 20 and particularly preferably 2 to 10 carbon atoms, such as acetoxy and benzoyloxy groups); acylamino groups (preferably those each having 2 to 30, more preferably 2 to 20 and particularly preferably 2 to 10 carbon atoms, such as acetylamino and benzoylamino groups); alkoxy-carbonylamino groups (preferably those each having 2 to 30, more preferably 2 to 20 and particularly preferably 2 to 12 carbon atoms, such as methoxy-carbonylamino group); aryloxy-carbonylamino groups (preferably those each having 7 to 30, more preferably 7 to 20 and particularly preferably 7 to 12 carbon atoms, such as phenyloxy-carbonylamino group); sulfonylamino groups (preferably those each having 1 to 30, more preferably 1 to 20 and particularly preferably 1 to 12 carbon atoms, such as methane-sulfonylamino and benzene-sulfonylamino groups); sulfamoyl groups (preferably those each having 0 to 30, more preferably 0 to 20 and particularly preferably 0 to 12 carbon atoms, such as sulfamoyl, methyl-sulfamoyl, dimethyl-sulfamoyl and phenyl-sulfamoyl groups); carbamoyl groups (preferably those each having 1 to 30, more preferably 1 to 20 and particularly preferably 1 to 12 carbon atoms, such as carbamoyl, methyl-carbamoyl, diethyl-carbamoyl and phenyl-carbamoyl groups); alkylthio groups (preferably those each having 1 to 30, more preferably 1 to 20 and particularly preferably 1 to 12 carbon atoms, such as methylthio and ethylthio groups); arylthio groups (preferably those each having 6 to 30, more preferably 6 to 20 and particularly preferably 6 to 12 carbon atoms, such as phenylthio group); hetero-arylthio groups (preferably those each having 1 to 30, more preferably 1 to 20 and particularly preferably 1 to 12 carbon atoms, such as pyridylthio, 2-benzimidazolyl-thio, 2-benzoxazolylthio and 2-benzothiazolylthio groups); sulfonyl groups (preferably those each having 1 to 30, more preferably 1 to 20 and particularly preferably 1 to 12 carbon atoms, such as mesyl and tosyl groups); sulfinyl groups (preferably those each having 1 to 30, more preferably 1 to 20 and particularly preferably 1 to 12 carbon atoms, such as methane-sulfinyl and benzene-sulfinyl groups); ureido groups (preferably those each having 1 to 30, more preferably 1 to 20 and particularly preferably 1 to 12 carbon atoms, such as ureido, methyl-ureido and phenyl-ureido groups); phosphoric acid amide groups (preferably those each having 1 to 30, more preferably 1 to 20 and particularly preferably 1 to 12 carbon atoms, such as diethyl-phosphoric acid amide and phenyl-phosphoric acid amide groups); hydroxyl groups, mercapto groups, halogen atoms (such as fluorine, chlorine, bromine and iodine atoms); a cyano group, a sulfo group, a carboxyl group, a nitro group, hydroxamic acid residues, a sulfino group, a hydrazino group, an imino group, heterocyclic groups (preferably those each having 1 to 30, more preferably 1 to 12 carbon atoms containing a hetero atom selected from, for instance, nitrogen, oxygen, sulfur atoms and mixture thereof, such as imidazolyl, pyridyl, quinolyl, furyl, thienyl, piperidyl, morpholino, benzoxazolyl, benzimidazolyl, benzothiazolyl, carbazolyl and azepinyl groups); and silyl groups (preferably those each having 3 to 40, more preferably 3 to 30 and particularly preferably 3 to 24 carbon atoms, such as trimethyl-silyl and triphenyl-silyl groups). These substituents may further have a substituent.

The fused aryl ring structure having a nucleic carbon atom number ranging from 10 to 20, which is included in at least one of the groups $Ar_{11}$, $Ar_{21}$ and $Ar_{31}$ appearing in the general formula (2d) as well as the substituents of the foregoing aryl groups represented by these groups $Ar_{11}$, $Ar_{21}$ and $Ar_{31}$ is, for instance, a naphthalene structure, an anthracene structure, a phenanthrene structure, a pyrene structure and a perylene structure. Among these, preferred are a naphthalene structure, an anthracene structure, a pyrene structure and a phenanthrene structure, more preferably used herein are a phenanthrene structure and aryl structures each comprising not less than 4 rings, with a pyrene structure being particularly preferred.

The fused heteroaryl ring structure having a nucleic carbon atom number ranging from 6 to 20, which is included in at least one of the groups $Ar_{11}$, $Ar_{21}$ and $Ar_{31}$ appearing in the general formula (2d) as well as the substituents of the foregoing aryl groups represented by these groups $Ar_{11}$, $Ar_{21}$ and $Ar_{31}$ is, for instance, a quinoline structure, a quinoxaline structure, a quinazoline structure, an acridine structure, a phenanthridine structure, a phthalazine structure and a phenanthroline structure and preferably used herein include a quinoline structure, a quinoxaline structure, a quinazoline structure, a phthalazine structure and a phenanthroline structure.

The trivalent group derived from an aromatic ring as an example of the group Ar appearing in the general formula (2d) is preferably one having 6 to 30, more preferably 6 to 20 and further preferably 6 to 16 carbon atoms. Specific examples thereof are trivalent groups derived from, for instance, benzene, naphthalene, anthracene, phenanthrene, pyrene and triphenylene.

The trivalent group derived from a heteroaromatic ring as another example of the group Ar appearing in the general formula (2d) preferably contains an atom selected from nitrogen, sulfur and oxygen atoms as the hetero atom, with nitrogen atom being more preferred. Moreover, it is preferably a trivalent group having 2 to 30, more preferably 3 to 20 and further preferably 3 to 16 carbon atoms. Specific examples thereof include trivalent groups derived from, for instance, pyridine, pyrazine, thiopyran, quinoline, quinoxaline and triazine. The trivalent group derived from such an aromatic or heteroaromatic ring may have a substituent. Such substituents may be, for instance, those listed above in connection with the aryl group represented by the foregoing group $Ar_{11}$. The group Ar is preferably a trivalent group derived from a benzene-triyl, naphthalene-triyl, anthracene-triyl, pyrene-triyl and a trivalent group derived from triphenylene. More preferably used herein are benzene-triyl groups and further preferably used include unsubstituted benzene-triyl groups (provided that they have of course $Ar_{11}$, $Ar_{21}$ and $Ar_{31}$) and alkyl-substituted benzene-triyl groups.

Specific examples of the benzene derivatives represented by the general formula (2d) which can be used in the organic EL element according to the present invention include a variety of known ones such as those disclosed in J.P. KOKAI 2002-324678 (see, the passages included in Sections [0079] to [0083]). Typical examples thereof will be listed below:

2d-1

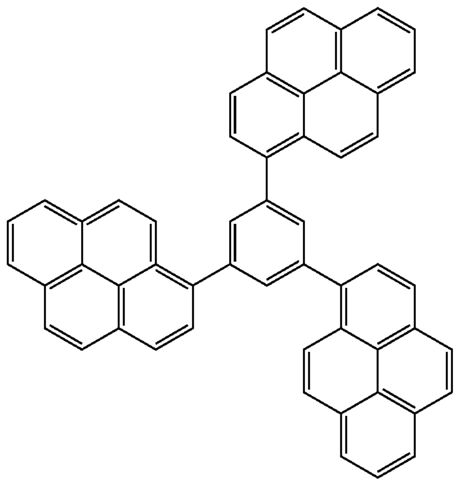

2d-2

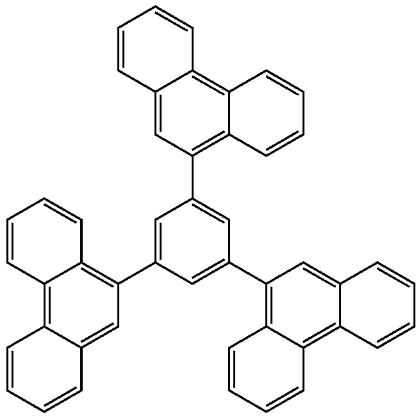

2d-3

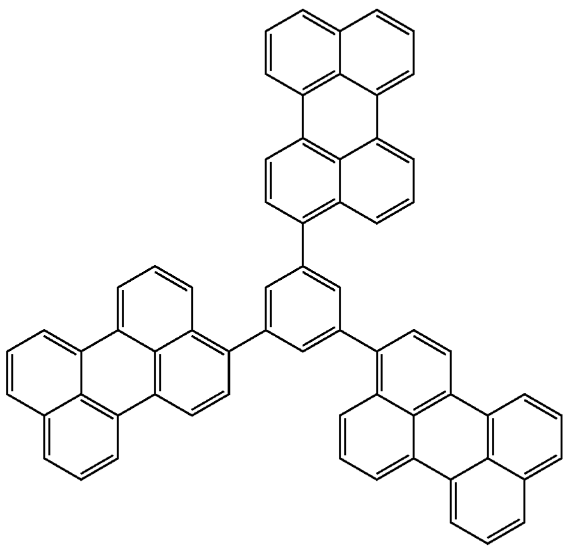

-continued
2d-4
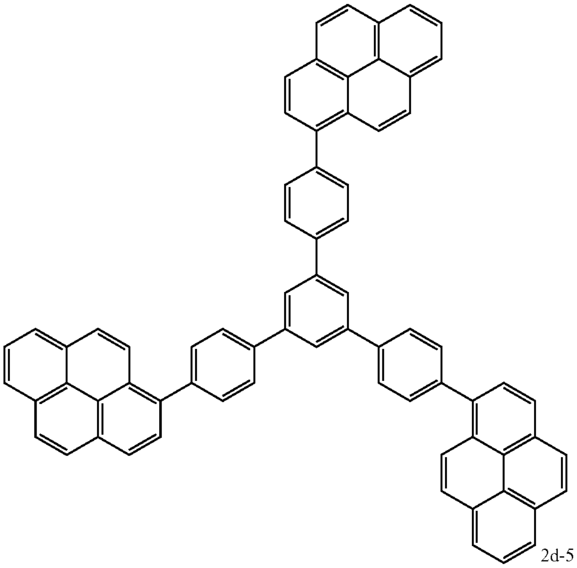
2d-5
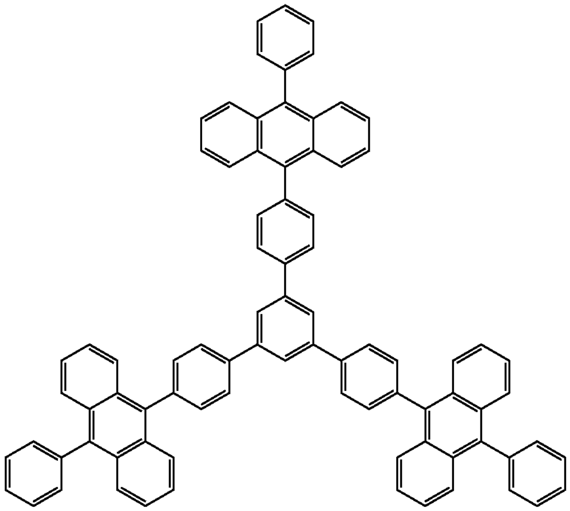
2d-6
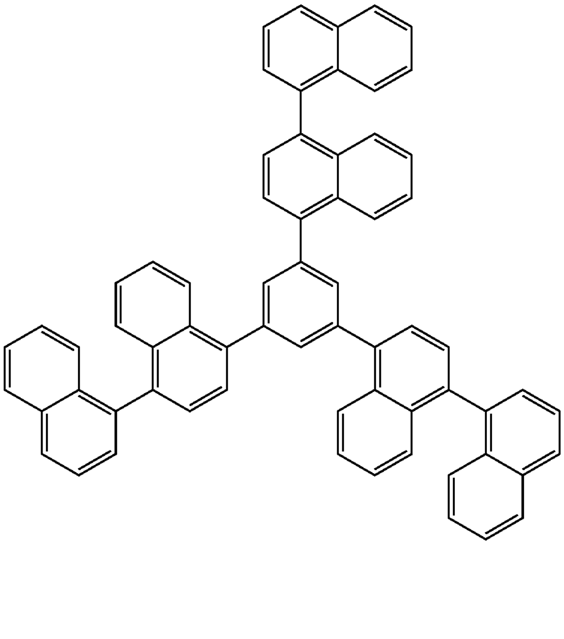
-continued
2d-7
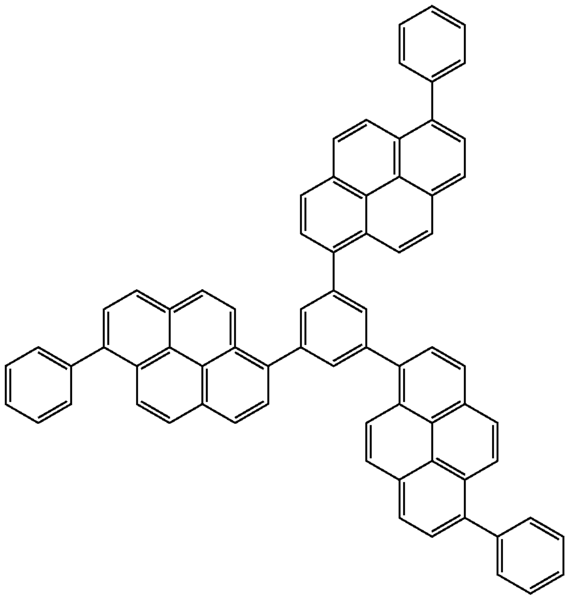
2d-8
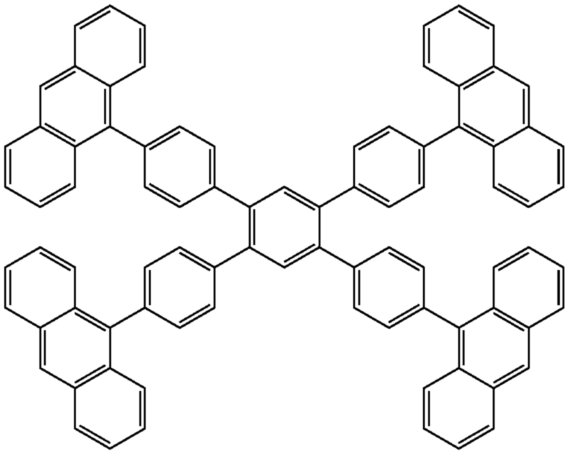
2d-9
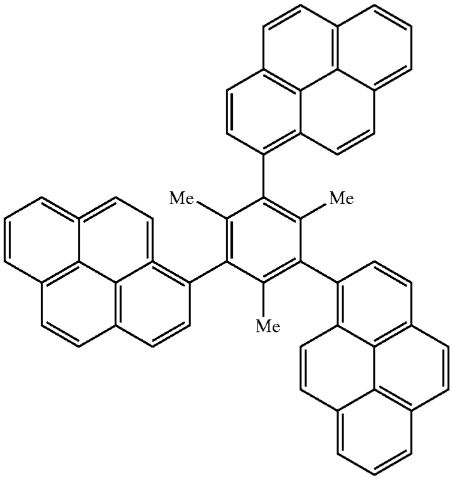

-continued
2d-10
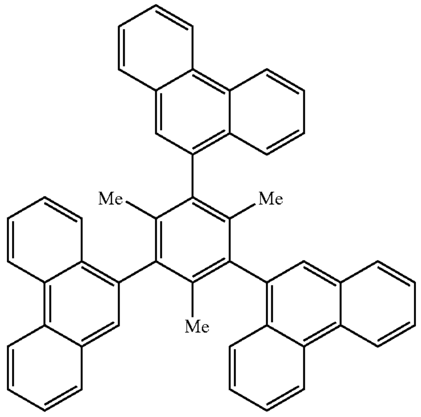
2d-11
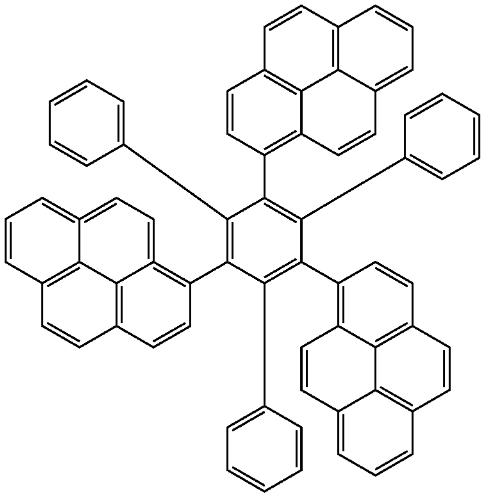
2d-12
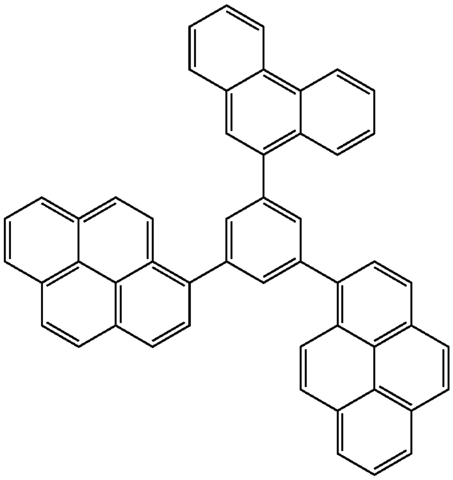
-continued
2d-13
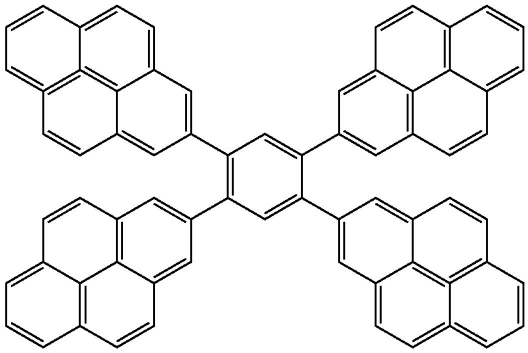
2d-14
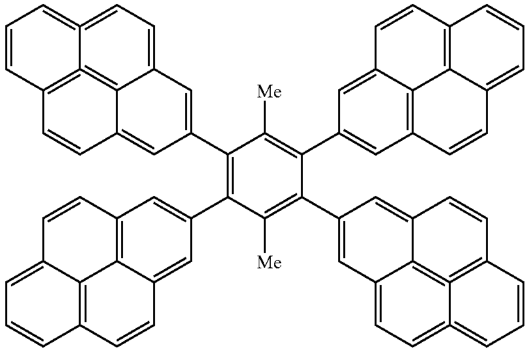
2d-15
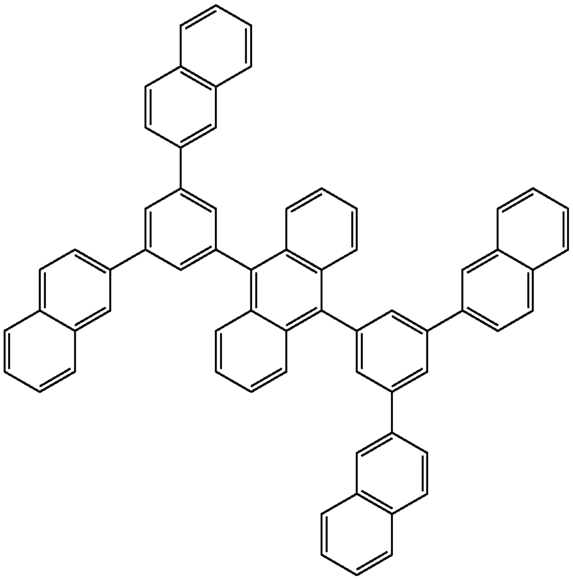

-continued 2d-16

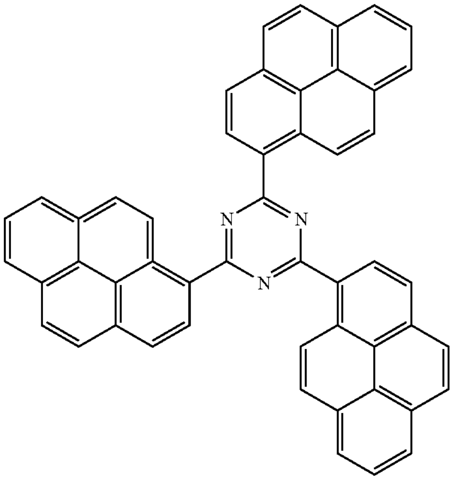

2d-17

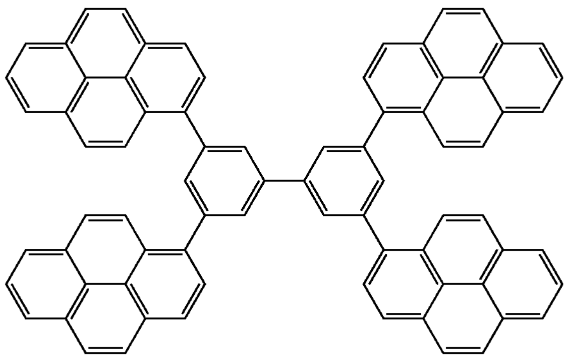

2d-18

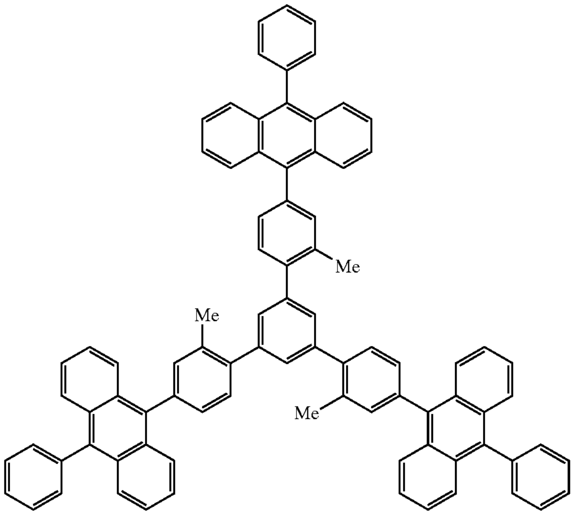

In the organic EL element according to the present invention, the light-emitting layer preferably comprises the fluoranthene compound of the present invention in an amount ranging from 0.01 to 20% by mass and more preferably 0.5 to 20% by mass on the basis of the total mass of the light-emitting layer.

The organic EL element according to the present invention preferably has such a structure that a layer selected from a chalcogenide layer, a metal halide layer and a metal oxide layer arranged on the surface of at least one of the paired electrodes.

(Construction of Organic EL Element)

The construction of the organic EL element according to the present invention will hereunder be described in more detail.

(1) Construction of Organic EL Element

The following are typical or representative construction of the organic EL element according to the present invention:

(a) Anode/light-emitting layer/cathode;

(b) Anode/hole-injection layer/light-emitting layer/cathode;

(c) Anode/light-emitting layer/electron-injection layer/cathode;

(d) Anode/hole-injection layer/light-emitting layer/electron-injection layer/cathode;

(e) Anode/organic semiconductor layer/light-emitting layer/cathode;

(f) Anode/organic semiconductor layer/electron barrier layer/light-emitting layer/cathode;

(g) Anode/organic semiconductor layer/light-emitting layer/adhesion-improving layer/cathode;

(h) Anode/hole-injection layer/hole-transporting layer/light-emitting layer/electron-injection layer/cathode;

(i) Anode/insulating layer/light-emitting layer/insulating layer/cathode;

(j) Anode/inorganic semiconductor layer/insulating layer/light-emitting layer/insulating layer/cathode;

(k) Anode/organic semiconductor layer/insulating layer/light-emitting layer/insulating layer/cathode;

(l) Anode/insulating layer/hole-injection layer/hole-transporting layer/light-emitting layer/insulating layer/cathode;

(m) Anode/insulating layer/hole-injection layer/hole-transporting layer/light-emitting layer/electron-injection layer/cathode.

Currently, preferably used herein are those having the layer structures specified in the foregoing item (h), among the embodiments of the construction of the element.

The compound of the present invention may be used in any one of the foregoing organic layers, but it is preferably used in the light-emitting zone or the hole-transporting zone among the foregoing constituent elements. The amount thereof to be incorporated into the zone ranges from 30 to 100% by mole.

(2) Translucent Substrate

The organic EL element according to the present invention is formed on a translucent substrate. The term "translucent substrate" herein used means a substrate used for supporting the organic EL element and preferably used herein is one having a smooth surface and having a light-transmittance for the visible light rays whose wavelength falls within the range of from 400 to 700 nm, on the order of not less than 50%.

Specific examples of such substrates include a glass plate and a polymer plate. Particularly preferred glass plates include, for instance, those made of, for instance, soda-lime glass, barium/strontium-containing glass, lead glass, aluminosolicate glass, borosilicate glass, barium-borosilicate glass, and quartz. On the other hand, examples of the foregoing polymer plates are those made of, for instance, polycarbonate, acrylic resins, polyethylene terephthalate, polyether sulfate and polysulfone.

(3) Anode

The anode of the organic EL element according to the present invention serves to inject holes into the hole-transporting layer or the light-emitting layer and it would be effective that the anode has a work function on the order of not less than 4.5 eV. Specific examples of materials constituting the electrode used in the present invention include indium-tin-oxide alloy (ITO), tin oxide (NESA), gold, silver, platinum, and copper. Furthermore, the anode would preferably be formed from a material having a small work function in order to efficiently inject electrons into the electron-transporting layer or the light-emitting layer.

The anode may be produced by forming a thin film of the foregoing electrode material according to any known film-forming method such as vacuum evaporation technique or the sputtering technique.

When leading out or picking out light rays emitted from the light-emitting layer through the anode, the anode is preferably so designed that it has a light-transmittance with respect to the emitted light on the order of higher than 10%. In addition, the anode preferably has a sheet resistance on the order of not more than several hundreds of ohms (Ω)/□. The film thickness of the anode may vary depending on the material selected, but the anode is in general so designed that it in general has a thickness ranging from 10 nm to 1 μm and preferably 10 to 200 nm.

(4) Light-Emitting Layer

The light-emitting layer of the organic EL element is one having the following functions in combination. More specifically, such functions are as follows:

(1) Injection Function: This function permits the injection of holes through the anode or the hole-injection layer and the injection of electrons through the cathode or the electron-injection layer upon the application of an electric field to the EL element;

(2) Transporting Function: This function permits the transfer or migration of the injected charges (electrons and holes) by the action of the electric field applied to the element;

(3) Light-Emitting Function: This function permits the provision of a field for ensuring the recombination of electrons with holes to thus induce or initiate the emission of desired light rays.

In this respect, however, the light-emitting layer has such a difference between the susceptibility to hole-injection and the susceptibility to electron-injection or, alternatively, the layer has a difference between the transport capacities represented by the mobility values of holes and electrons respectively. In this respect, it is preferred in the present invention to move either one of the holes and electrons.

This light-emitting layer can be prepared by any known method such as the vacuum evaporation technique, the spin coating technique, the LB technique. The light-emitting layer used in the present invention is particularly preferably a molecular-deposition film.

In this respect, the term "molecular-deposition film" used herein means a thin film formed by the deposition of a raw compound in a gaseous state; or a film formed through the solidification of a raw compound in the form of a solution or a liquid state and the molecular-deposition film can in general be distinguished from the thin film (molecular cumulative or built-up film) prepared according to the LB technique, on the basis of the differences, between them, in the cohesive structure and in the higher-order structure as well as the difference in the mechanical functions due to the foregoing structural differences.

In addition, the light-emitting layer may likewise be prepared by a method comprising the step of preparing a solution of a binder such as a resin and a raw compound by dissolving them in a solvent and then forming a thin film using the resulting solution according to the spin coating technique, as disclosed in J.P. KOKAI Sho 57-51781.

In the present invention, the light-emitting layer may if necessary comprise any known light-emitting material other than the light-emitting material of the present invention which comprises a compound having a fluoranthene structure of the present invention and a fused ring-containing compound, inasmuch as the former never adversely affects the intended purposes of the present invention or an additional light-emitting layer containing a known light-emitting material may be deposited on or laminated with the light-emitting layer consisting of the light-emitting material of the present invention.

The thickness of the light-emitting layer preferably ranges from 5 to 50 nm, more preferably 7 to 50 nm and most preferably 10 to 50 nm. This is because if the thickness thereof is less than 5 nm, it would be difficult to form a desired light-emitting layer and this accordingly makes, quite difficult, the control of the chromaticity of the resulting EL element, while if it exceeds 50 nm, the driving voltage of the El element may unreasonably increase.

(5) Hole-Injecting and Transporting Layer (Hole-Transporting Zone)

The hole-injecting and transporting layer is a layer for helping the injection of holes into the light-emitting layer and for transporting the same to the light-emitting zone and it can ensure a high hole-mobility and in general has a low ionization energy on the order of not more than 5.5 eV. As materials for forming such a hole-injecting and transporting layer, preferably used herein are those which permit the transportation of holes to the light-emitting layer at a lower electric field strength and which can further preferably ensure the mobility of holes of, for instance, at least $10^{-4}$ $cm^2/V$ when applying, to the layer, an electric field ranging from $10^{-4}$ to $10^6$ V/cm.

When using, in the hole-transporting zone, the compound of the present invention having a fluoranthene structure, the hole-injecting and transporting layer may be formed from the compound of the present invention having a fluoranthene structure alone or in combination with another material.

The material used for forming the hole-injecting and transporting layer in combination with the compound of the present invention having a fluoranthene structure is not restricted to any specific one inasmuch as it can satisfy the foregoing requirements for the preferred characteristic properties and accordingly, the material usable in the present invention for forming the hole-injecting and transporting layer can appropriately be selected from the group consisting of the conventional positively charged hole-transfer materials currently used in the photoelectro-conductive materials; and those known in this art and used for forming a hole-injecting and transporting layer of organic EL elements.

Specific examples of such materials for forming the hole-injecting and transporting layer of the present invention are triazole derivatives (see, for instance, U.S. Pat. No. 3,112,197); oxadiazole derivatives (see, for instance, U.S. Pat. No. 3,189,447); imidazole derivatives (Japanese Examined Patent Publication (hereunder referred to as "J.P. KOKOKU") Sho 37-16096); poly(aryl-alkane) derivatives (see, for instance, U.S. Pat. Nos. 3,615,402, 3,820,989 and 3,542,544; J.P. KOKOKU Nos. Sho 45-555 and Sho 51-10983; and J.P. KOKAI Nos. Sho 51-93224, Sho 55-17105, Sho 56-4148, Sho 55-108667, Sho 55-156953 and Sho 56-36656); pyrazoline derivatives and pyrazolone derivatives (see, for instance, U.S. Pat. Nos. 3,180,729 and 4,278,746; and J.P. KOKOKU Nos. Sho 55-88064, Sho 55-88065, Sho 49-105537, Sho 55-51086, Sho 56-80051, Sho 56-88141, Sho 57-45545, Sho 54-112637 and Sho 55-74546); phenylene-diamine derivatives (see, for instance, U.S. Pat. No. 3,615,404; and J.P. KOKOKU Nos. Sho 51-10105, Sho 46-3712, Sho 47-25336 and Sho 54-119925); arylamine derivatives (see, for instance, U.S. Pat. Nos. 3,567,450, 3,240,597, 3,658,520, 4,232,103, 4,175,961 and 4,012,376; J.P. KOKOKU Nos. Sho 49-35702 and Sho 39-27577; J.P. KOKAI Nos. Sho 55-144250, Sho 56-119132 and Sho 56-22437; and German Patent No. 1,110,518); amino-substituted chalcone derivatives (see, for instance, U.S. Pat. No. 3,526,501); oxazole derivatives (such as those disclosed in, for instance, U.S. Pat. No. 3,257,203); styryl anthracene derivatives (see, for instance, J.P. KOKAI No. Sho 56-46234); fluorenone derivatives (see, for instance, J.P. KOKAI No. Sho 54-110837); hydrazine derivatives (see, for instance, U.S. Pat. No. 3,717,462; and J.P. KOKAI Nos. Sho 54-59143, Sho 55-52063, Sho 55-52064, Sho 55-46760, Sho 57-11350, Sho 57-148749, and Hei 2-311591); stilbene derivatives (see, for instance, J.P. KOKAI Nos. Sho 61-210363, Sho 61-228451, Sho 61-14642, Sho 61-72255, Sho 62-47646, Sho 62-36674, Sho 62-10652, Sho 62-30255, Sho 60-93455, Sho 60-94462, Sho 60-174749 and Sho 60-175052); silazane derivatives (see, for instance, U.S. Pat. No. 4,950,950); polysilane type ones (see J.P. KOKAI No. Hei 2-204996); and aniline moiety-containing copolymers (see J.P. KOKAI No. Hei 2-282263).

The materials listed above can be used for forming the hole-injecting and transporting layer, but preferably used herein include, for instance, porphyrin compounds (such as those disclosed in, for instance, J.P. KOKAI No. Sho 63-295695); aromatic tertiary amine compounds and styrylamine compounds (see, for instance, U.S. Pat. No. 4,127,412; and J.P. KOKAI Nos. Sho 53-27033, Sho 54-58445, Sho 55-79450, Sho 55-144250, Sho 56-119232, Sho 61-295558, 61-98353, and Sho 63-295695), among others. In particular, preferably used herein include aromatic tertiary amine compounds.

Also listed herein are, for instance, compounds each having two fused aromatic rings in the molecule as disclosed in U.S. Pat. No. 5,061,569 such as 4,4'-bis(N-(1-naphthyl)-N-phenylamino) biphenyl (hereunder abbreviated as "NPD") and those disclosed in J.P. KOKAI Hei 4-308688 such as 4,4',4"-tris(N-(3-methyl-phenyl)-N-phenylamino) triphenylamine (hereunder abbreviated as "MTDATA") in which three triphenyl-amine units are connected in the form of a star burst-like shape.

In addition to the aromatic di-methylidyne type compounds already described above, inorganic compounds such as p-type Si and p-type SiC can likewise be used as materials for forming the hole-injecting layer in the present invention.

The hole-injecting and transporting layer can be formed by converting the foregoing compound into a thin film according to any known methods such as the vacuum evaporation technique, the spin coating technique, the casting method, and the LB technique. The thickness of the hole-injecting and transporting layer is not restricted to any particular level, but it in general ranges from 5 nm to 5 μm.

(6) Electron-Injecting Layer

The electron-injecting layer is a layer for assisting the injection of electrons into the light-emitting layer, which can ensure a high electron-mobility, while an adhesion-improving layer is an electron-injecting layer which consists of a material excellent in the adhesion to the cathode. As the material used for forming such an electron-injecting layer, suitably used herein are 8-hydroxy quinoline and metal complexes of the derivatives thereof.

Specific examples of such 8-hydroxy quinoline and metal complexes of the derivatives thereof include metal chelates of oxinoid compounds such as chelates of oxine (in general, 8-quinolinol or 8-hydroxy quinoline).

For instance, Alq as described in the section concerning the light-emitting materials can be used as a material for forming the electron-injecting layer.

On the other hand, examples of the oxadiazole derivatives include the following electron-transfer compounds represented by the following general formula:

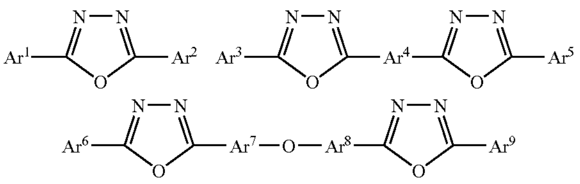

In these formulas, $Ar^1$, $Ar^2$, $Ar^3$, $Ar^5$, $Ar^6$ and $Ar^9$ may be the same or different and each of them represents a substituted or unsubstituted aryl group. In addition, $Ar^4$, $Ar^7$ and $Ar^8$ may likewise be the same or different and each of them represents a substituted or unsubstituted arylene group.

In this connection, examples of such aryl groups are phenyl, biphenyl, anthranyl, perylenyl, and pyrenyl groups. Moreover, examples of the foregoing arylene groups are phenylene, naphthylene, biphenylene, anthranylene, perylenylene, and pyrenylene groups. Moreover, examples of substituents of the foregoing aryl and arylene groups are alkyl groups each having 1 to 10 carbon atoms, and alkoxy and cyano groups each having 1 to 10 carbon atoms. As such electron-transfer compounds, preferably used herein include those having a thin film-forming ability.

Specific examples of the foregoing electron-transfer compounds include those listed below:

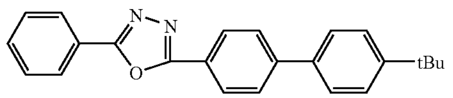

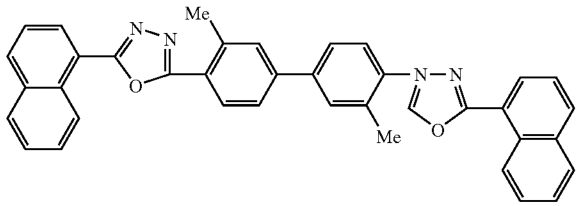

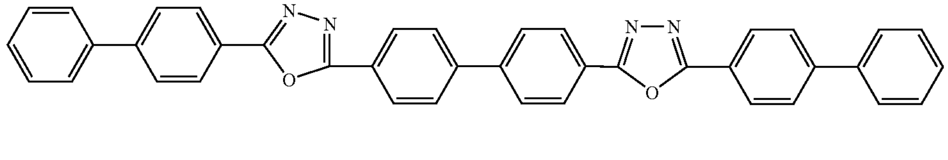

-continued

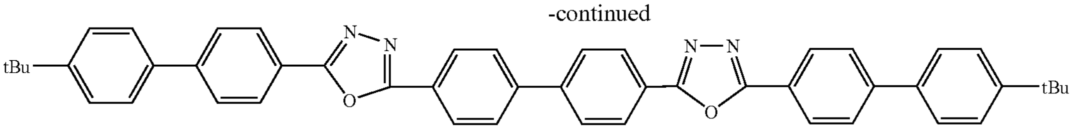

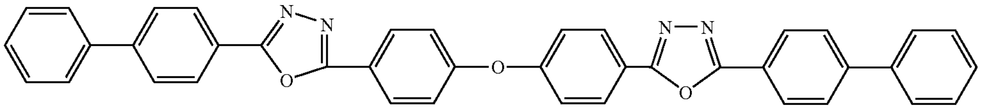

A preferred embodiment of the organic EL element of the present invention is an element containing a reducing dopant in a zone for transporting electrons or the boundary between the cathode and the organic layer. In this respect, the term "reducing dopant" used herein can be defined to be a substance which can reduce an electron-transportable compound. Accordingly, a variety of substances can be used as such a reducing dopant insofar as it can show a desired reducing ability and the substances suitably used herein may be at least one member selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals and organic complexes of rare earth metals.

More specifically, examples of the foregoing reducing dopants preferably used in the invention include at least one alkali metal selected from the group consisting of Li (work function (WF): 2.9 eV), Na (WF: 2.36 eV), K (WF: 2.28 eV), Rb (WF: 2.16 eV) and Cs (WF: 1.95 eV); or at least one alkaline earth metal selected from the group consisting of Ca (WF: 2.9 eV), Sr (WF: 2.0 to 2.5 eV) and Ba (WF: 2.52 eV), with those having a work function of not more than 2.9 eV being particularly preferably used in the present invention. Among them, more preferably used herein include at least one alkali metal selected from the group consisting of K, Rb and Cs, further preferably used herein include Rb and Cs, and most preferably used herein is Cs. These alkali metals show a particularly high reducing ability and they would permit the improvement of the luminance of the emitted light rays and the substantial extension of the lifetime of the resulting organic EL element through the addition thereof to the electron-injection zone even in a relatively small quantity. Furthermore, it is also preferred to use a combination of at least two such alkali metals as the reducing dopant whose work function is not more than 2.9 eV and particularly preferably used in the present invention are combinations including Cs as a constituent thereof such as the combination of Cs with Na; Cs with K; Cs with Rb; or Cs with Na. More specifically, the use of such a combination containing Cs as a constituent thereof can efficiently show its reducing ability and would permit the improvement of the luminance of the emitted light rays and the substantial extension of the lifetime of the resulting organic EL element through the addition thereof to the electron-injection zone.

The organic electroluminescent element of the present invention may further comprise an electron-injecting layer composed of a dielectric material or a semiconductor material, which is arranged between the cathode and the organic layer. This would permit the effective prevention of any leakage of the electric current to thus improve the electron-injecting ability. Such dielectric materials preferably used herein are at least one metal compound selected from the group consisting of alkali metal chalcogenides, alkaline earth metal chalcogenides, halides of alkali metals, and halides of alkaline earth metals. Accordingly, the electron-injecting layer is preferably constituted by, for instance, such an alkali metal chalcogenide and this in turn leads to the further improvement of the electron-injecting ability of the layer. Specific examples of alkali metal chalcogenides preferably used in the present invention include $Li_2O$, $K_2O$, $Na_2S$, $Na_2Se$ and $Na_2O$, preferred examples of alkaline earth metal chalcogenides are CaO, BaO, SrO, BeO, BaS and CaSe. In addition, preferred examples of halides of alkali metals are LiF, NaF, KF, LiCl, KCl and NaCl. Furthermore, preferred examples of halides of alkaline earth metals include fluorides such as $CaF_2$, $BaF_2$, $SrF_2$, $MgF_2$ and $BeF_2$, and halides thereof other than fluorides.

In addition, semiconductor materials used for constructing the electron-transporting layer include, for instance, oxides, nitrides and oxy-nitrides containing at least one element selected from the group consisting of Ba, Ca, Sr, Yb, Al, Ga, In, Li, Na, Cd, Mg, Si, Ta, Sb and Zn, which may be used alone or in any combination of at least two of them. In this connection, the inorganic compound constituting the electron-transporting layer is preferably in the form of a microcrystalline or amorphous dielectric thin film. The use of such a dielectric material for forming such an electron-transporting layer would permit the formation of a more uniform dielectric thin film and therefore, this would result in the substantial reduction of the defects of picture elements such as the formation of dark spots. In this respect, however, such inorganic compounds may be, for instance, those already listed above such as alkali metal chalcogenides, alkaline earth metal chalcogenides, halides of alkali metals and halides of alkaline earth metals.

(7) Cathode

The cathode used herein is one comprising, as an electrode material, a metal, an alloy, an electrically conductive compound or a mixture thereof, which has a low work function (not more than 4 eV) since the cathode should permit the injection of electrons into the electron-injecting and transporting layer or a light-emitting layer. Specific examples of such electrode materials include sodium, sodium/potassium alloy, magnesium, lithium, magnesium/silver alloy, aluminum/aluminum oxide, aluminum/lithium alloy, indium and a rare earth metal.

This cathode can be prepared by converting such an electrode material into a thin film according to any known film-forming method such as the evaporation method or the sputtering method.

In this connection, when leading or picking the light rays emitted from the light-emitting layer out through the cathode, the cathode is preferably so designed that it has a light-transmittance with respect to the emitted light on the order of higher than 10%.

In addition, the cathode preferably has a sheet resistance on the order of not more than several hundreds of ohms (Ω)/□. The cathode is in general so designed that it has a thickness ranging from 10 nm to 1 μm and preferably 50 to 200 nm.

(8) Insulating or Dielectric Layer

In the organic EL element of the invention, an electric field is applied to an ultra-thin film and accordingly, the element is quite susceptible to the formation of pixel defects due to any leakage and/or the formation of short circuits. To prevent the occurrence of any such problem, it is preferred that an insulating thin film or layer is arranged between the paired electrodes.

Examples of materials used for forming such an insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide.

In the present invention, it is also possible to use a mixture of the foregoing materials or a thin film having a multi-layered structure (a laminate) comprising a plurality of the foregoing materials.

(9) Preparation of Organic EL Element

The organic EL element according to the present invention can be prepared by, for instance, forming an anode, a light-emitting layer, a hole-injecting layer, if necessary, and an optional electron-injecting layer; and further forming a cathode, using the materials detailed above and the methods described above. Alternatively, the foregoing components may likewise be formed in the reverse order starting from the cathode to the anode to thus form an organic EL element.

By way of example, an organic EL element is prepared on a translucent substrate, by the formation of, in order, anode/hole-injecting layer/light-emitting layer/electron-injecting layer/cathode.

First of all, a thin film comprising an anode material is formed on an appropriate translucent substrate to a thickness of not more than 1 μm and preferably 10 to 200 nm according the any known film-forming method such as the evaporation technique or the sputtering technique to thus give an anode. Then a hole-injecting layer is formed on the anode thus formed. The hole-injecting layer can be formed according to any known method such as the vacuum evaporation, spin coating, cast coating or LB technique as has been discussed above, but the hole-injecting layer is preferably formed according to the vacuum evaporation method since the latter would permit, for instance, the easy formation of a uniform film and the prevention of the formation of any pinhole. When forming a hole-injecting layer according to the vacuum evaporation method, the conditions for the evaporation may variously vary depending on the kind of compounds used (materials for forming hole-injecting layer) and the crystalline structure and recombined structure of the intended hole-injecting layer, but it is common that the vacuum evaporation method is preferably carried out under the following conditions appropriately selected: the temperature of the evaporation source: 50 to 450° C.; the degree of vacuum: $10^{-7}$ to $10^{-3}$ Torr; the evaporation rate: 0.01 to 50 nm/sec; the substrate temperature: −50 to 300° C.; the film thickness: 5 nm to 5 μm.

Subsequently, a light-emitting layer is applied onto the hole-injecting layer. The light-emitting layer may likewise be formed by converting a desired organic light-emitting material into a thin film according to any known method such as the vacuum evaporation, spin coating, cast coating or LB technique, but the light-emitting layer is preferably formed according to the vacuum evaporation method since the latter would permit, for instance, the easy formation of a uniform film and the prevention of the formation of any pinhole. When forming a light-emitting layer according to the vacuum evaporation method, the conditions for the evaporation may variously vary depending on the kind of compounds used, but it is common that the vacuum evaporation method is preferably carried out under the conditions similar to those described above in connection with the formation of the hole-injecting layer.

Next, an electron-injecting layer is formed on the light-emitting layer. The electron-injecting layer is preferably formed by the vacuum evaporation method since a uniform film should be formed, like the foregoing hole-injecting layer and the light-emitting layer. In this respect, the vacuum evaporation method is preferably carried out under the conditions similar to those described above in connection with the formation of the hole-injecting layer and the light-emitting layer.

The compound of the present invention may be co-evaporated together with other materials when using the vacuum evaporation method, although the applicability of such a co-evaporation technique may be dependent upon whether the compound is incorporated into the light-emitting zone or the hole-transporting zone. Moreover, when using the spin coating technique, other materials can be incorporated into the film by blending the same with the compound of the invention in the coating liquid to be applied.

Finally, a cathode is deposited on the electron-injecting layer to thus form an organic EL element.

The cathode is, in this case, a layer consisting of a metal and accordingly, it can be formed by the evaporation method or the sputtering method. However, preferably used herein is the vacuum evaporation technique for the purpose of protecting the underlying layers of organic substances from any defect possibly formed during the cathode film-forming step.

The production steps of the organic EL element as has been described above should preferably be carried out continuously, from the step for forming the anode to the step for forming the cathode, within a single vacuum evacuation cycle.

The method for forming each layer constituting the organic EL element of the present invention is not restricted to any specific one at all. Any conventionally known one such as the vacuum evaporation method and the spin coating method can be used in the present invention. The organic thin film layer containing the compound represented by the foregoing general formula (1) used in the organic EL element of the present invention can be formed by any known film-forming method such as the vacuum evaporation method, the molecular beam evaporation method (MBE method) or any known coating method such as the dip coating method using a solution of such a compound in a solvent, the spin coating method, the cast coating method, the bar coating method or the roll coating method.

The thickness of each organic layer of the organic EL element according to the present invention is not restricted to any specific level, but if the organic layer is too thin, the resulting layer is quite susceptible to the formation of defects such as pinholes, while if it is too thick, the resulting EL element requires the application of a high electric voltage for the operation thereof and this leads to the reduction of the efficiency thereof. For this reason, it is common that the thickness thereof preferably ranges from several nanometers to 1 μm.

In this connection, when applying a DC voltage to the organic EL element, a voltage ranging from 5 to 40 V is applied while the polarity of the anode is made positive and that of the cathode is made negative so that the emission of light rays can be observed. On the other hand, any electric current never flows through the element even when an electric voltage is applied thereto, in case where it is applied in such a condition that the polarities of the electrodes are reversed and accordingly, there is not observed any emitted light ray. Alternatively, when applying an alternating voltage to the element, there is observed uniform light-emission at an instance only when the anode is positively polarized, while the cathode is negatively polarized. In this respect, the alternating current to be applied to the element may have any wave form.

(Application of Organic EL Element)

The organic EL element of the present invention can be applied to any article which should have a high luminance and a high light-emission efficiency even at a low applied electric voltage. For instance, the organic EL element of the invention can be applied to display devices, displays, lighting apparatuses, light sources for printers, and back-lighting devices for liquid crystal devices and the EL element can likewise used in the fields of markers or signals, signboards or advertising signs, and the interior. The display device may be, for instance, a flat panel display which would permit the energy-saving and/or ensure a high visibility. In addition, the EL element of the present invention can be used as a light source for a printer such as the light source for use in the laser beam printers. Further, the use of the element of the present invention permits the considerable reduction of the volume of the device to which it is applied. In respect of the lighting apparatuses and back-lighting devices, it would be expected to achieve an energy-saving effect through the use of the element of the present invention.

EXAMPLE

The present invention will hereunder be described in more detail with reference to the following Examples, but the present invention is by no means limited to these specific Examples.

The present invention will hereunder be described in more detail with reference to the following Examples, but the present invention is not restricted to these specific Examples, inasmuch as they are never beyond the gist of the present invention.

Illustrative Synthesis 1: Synthesis of Compound A

Compound A

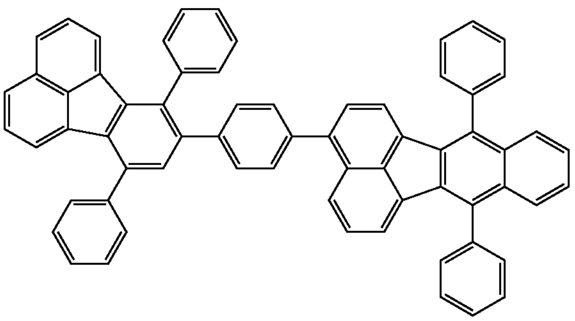

Synthetic Pathway

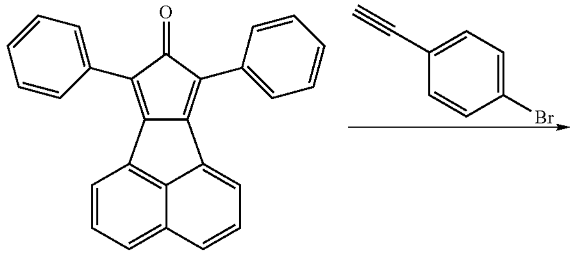

Starting Material 1

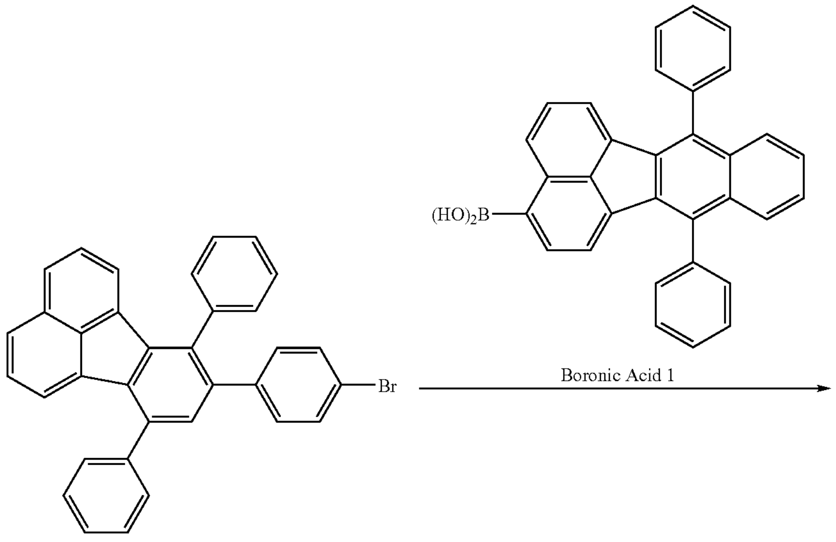

Intermediate 1

-continued

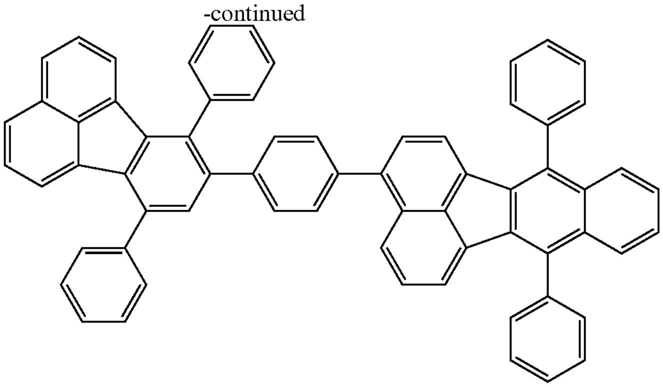

Compound A

Synthesis of Intermediate 1:

To 10 mL of xylene, there were added the starting raw material 1 (5.9 g, 17 mM) and 4-bromophenyl acetylene (3 g, 17 mM) and then the resulting mixture was refluxed with heating over 16 hours. To the reaction solution, there was added methanol to thus make the resulting solids separate, followed by the removal of the solids through filtration and the washing of the solids with methylene chloride to thus give the title intermediate 1 as a yellow solid (5.6 g, yield: 65%).

Synthesis of Compound A:

To 20 mL of toluene, there were added the intermediate 1 (2.3 g, 4.5 mM), boronic acid 1 (2.2 g, 5 mM), and tetrakis (triphenyl-phosphino) palladium (0.16 g, 0.14 mM), in an atmosphere of argon, and a 2M aqueous sodium carbonate solution (7 mL, 14 mM) was then added to the resulting mixture, followed by the stirring with heating at 80° C.

To the reaction solution, there was added methanol to make solids thus formed separate, followed by the removal of the solids through filtration and the washing of the solids with methylene chloride to thus give the intended compound A as a yellow solid (3.0 g, yield: 83%).

Field Desorption Mass Spectrometry (FD-MS): Calculated (for C66H40): 832. Found: 832.

Illustrative Synthesis 2: Synthesis of Compound B

Compound B

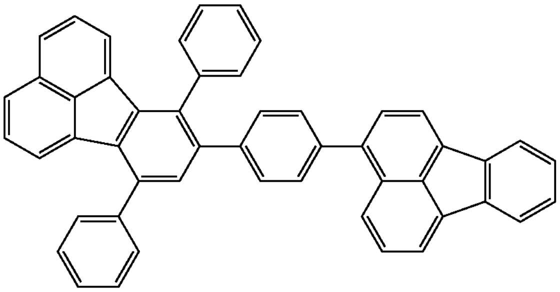

Synthetic Pathway

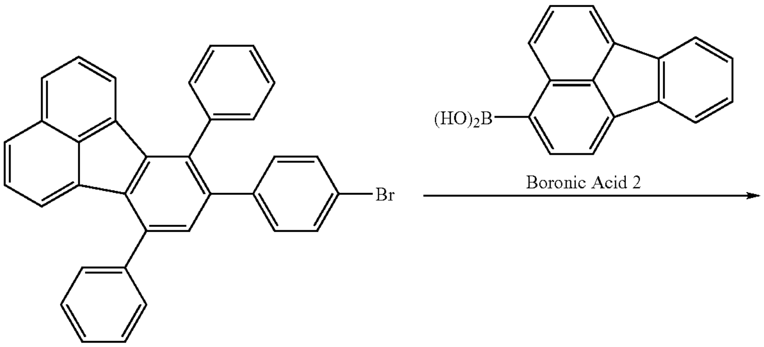

Intermediate 1

-continued

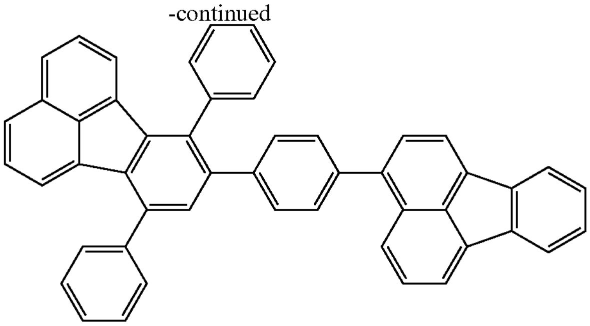

Compound B

To 20 mL of toluene, there were added the intermediate 1 (2.3 g, 4.5 mM), boronic acid 2 (1.2 g, 5 mM), and tetrakis (triphenyl-phosphino) palladium (0.16 g, 0.14 mM), in an atmosphere of argon, and a 2M aqueous sodium carbonate solution (7 mL, 14 mM) was then added to the resulting mixture, followed by the stirring with heating at 80° C.

To the reaction solution, there was added methanol to make solids thus formed separate, followed by the removal of the solids through filtration and the washing of the solids with methylene chloride to thus give the intended compound B as a yellow solid (1.4 g, yield: 49%).

Field Desorption Mass Spectrometry (FD-MS): Calculated (for C50H30): 630. Found: 630.

Illustrative Synthesis 3: Synthesis of Compound C

Compound C

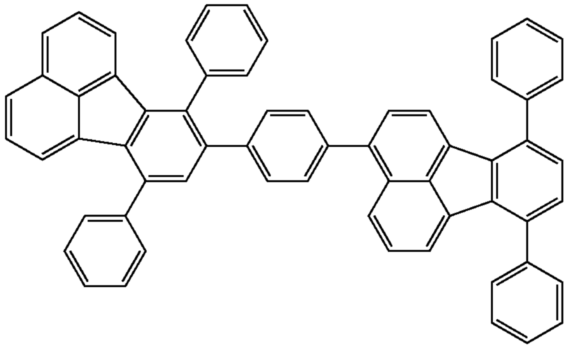

Synthetic Pathway

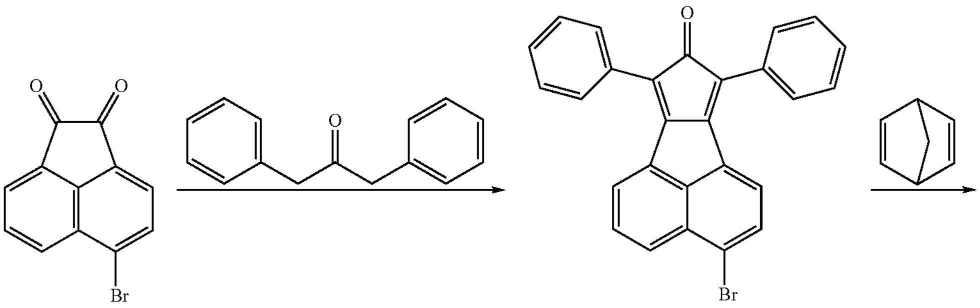

Starting Material 2

Intermediate 2

-continued

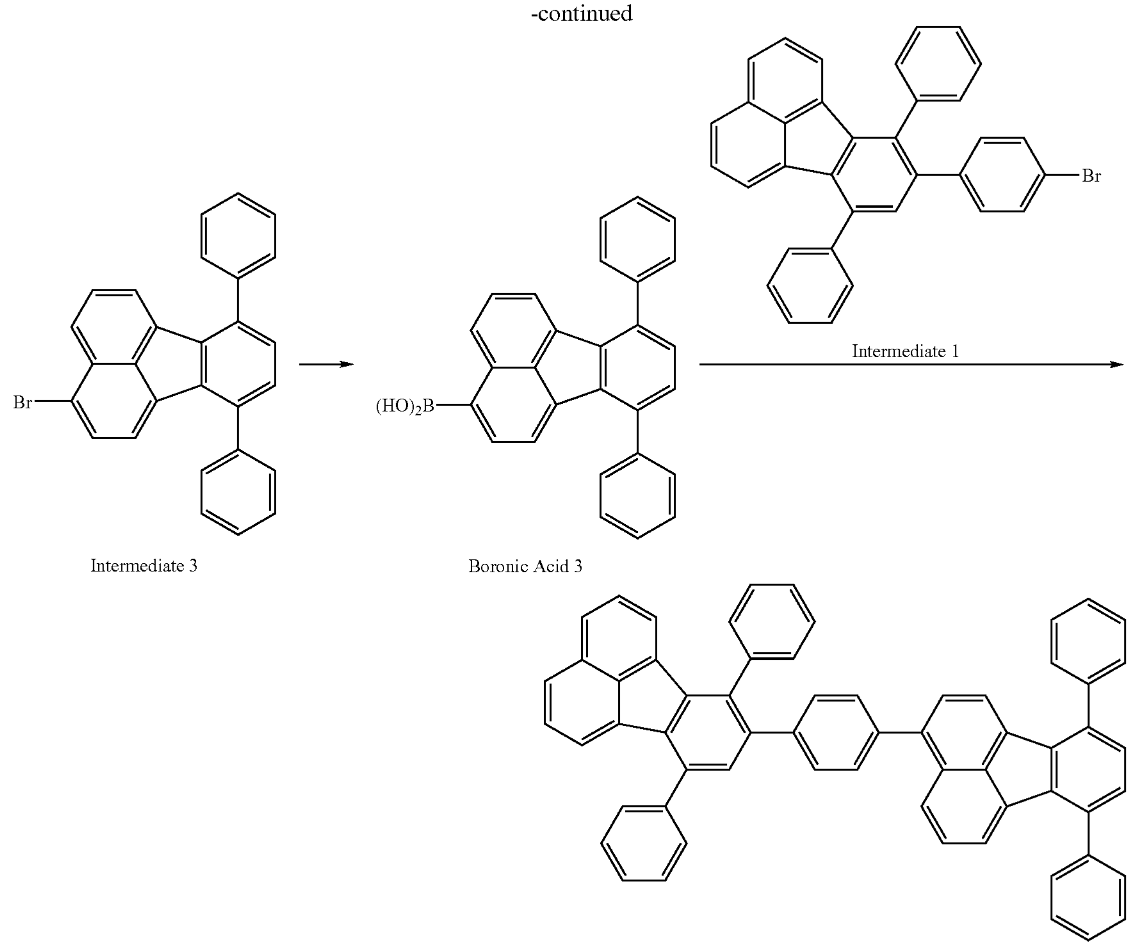

Intermediate 3

Boronic Acid 3

Intermediate 1

Compound C

Synthesis of Intermediate 2:

To 100 mL of methanol, there were added 1,3-dipneyl-2-propanone (10 g, 48 mM) and the starting raw material 2 (12.5 g, 48 mM), followed by the gradual addition of 10 mL of a methanolic potassium hydroxide (1.7 g, 30 mM) solution and the subsequent reflux with heating for 2 hours. The solids precipitated were filtered off and washed with xylene to thus give purple solids (15 g, yield: 72%).

Synthesis of Intermediate 3:

To 10 mL of xylene, there were added the intermediate 2 (7.4 g, 17 mM) and 2,5-norbornadiene (1.6 g, 17 mM) and then the resulting mixture was heated under reflux over 16 hours. To the reaction solution, there was added methanol to make solids thus formed separate, followed by the removal of the solids through filtration and the washing of the solids with methylene chloride to thus give the intended intermediate 3 as a yellow solid (5.1 g, yield: 70%).

Synthesis of Boronic Acid 3:

In an atmosphere of argon, the intermediate 3 (3.9 g, 9 mM) was dissolved in 10 mL of anhydrous tetrahydrofuran and 10 mL of anhydrous toluene, the resulting solution was cooled to a temperature of −20° C., the addition of a 1.6 M dispersion of n-butyl lithium (6.6 mL, 11 mM) was then added to the solution and then it was stirred for one hour. Thereafter, the reaction solution was cooled to −60° C., followed by the addition of 10 mL of a solution of boronic acid tri-isopropyl ester (3.4 g, 18 mM) in tetrahydrofuran and the subsequent stirring of the mixture for one hour. The reaction solution was again warmed up to room temperature and the stirring of the solution was continued over 5 hours.

To the reaction solution, there was added 30 mL of a 1N aqueous hydrochloric acid solution, followed by the stirring of the mixture for 30 minutes and the separation of the organic phase. The resulting organic phase was concentrated under a reduced pressure using an evaporator and the solids precipitated out of the organic phase were washed with hexane to thus give the desired boronic acid 3 in the form of a solid (2.2 g, yield: 65%).

Synthesis of Compound C:

To 10 mL of toluene, there were added the intermediate 1 (1.1 g, 2.2 mM), boronic acid 3 (0.95 g, 2.5 mM), and tetrakis (triphenyl-phosphino) palladium (0.08 g, 0.07 mM), in an atmosphere of argon, and a 2M aqueous sodium carbonate solution (3.5 mL, 7 mM) was then added to the resulting mixture, followed by the stirring thereof with heating at 80° C.

To the reaction solution, there was added methanol to make solids thus formed separate, followed by the removal of the solids through filtration and the washing of the solids with methylene chloride to thus give the intended compound C as a yellow solid (1.2 g, yield: 71%).

Field Desorption Mass Spectrometry (FD-MS): Calculated (for C62H38): 782. Found: 782.

Example 1

(1) Preparation of Organic EL Element

A transparent electrode consisting of indium tin oxide was formed on a glass substrate having a size of 25 mm×75 mm×1.1 mm (thick) in a thickness of 120 nm. This glass substrate was washed with isopropyl alcohol while applying ultrasonic waves and then it was irradiated with ultraviolet rays and exposed to ozone for cleansing.

Then the glass substrate provided thereon with the transparent electrode was fitted to a substrate holder within the evaporation chamber of a vacuum evaporation system and at the same time, the vacuum chamber of the system was evacuated to a vacuum of $1\times10^{-3}$ Pa.

First, a film was formed by the vapor deposition of N',N"-bis[4-(diphenylamino) phenyl]-N',N"-diphenyl-biphenyl-4, 4'-diamine, in a thickness of 60 nm, on the side of the substrate on which the transparent electrode had been formed, in such a manner that the transparent electrode was completely covered with the film, at an evaporation velocity of 2 nm/sec. The resulting film serves as a hole-injecting layer.

Then another film was formed by the vapor deposition of N,N,N',N'-tetra(4-biphenylyl)-benzidine on the surface of the hole-injecting layer to a film thickness of 20 nm, while setting the evaporation velocity at 2 nm/sec. The resulting film serves as a hole-transporting layer.

The compound (2a'-55) and the compound A were simultaneously vapor-deposited, to a thickness of 40 nm, on the hole-transporting layer at evaporation velocities of 2 nm/sec and 0.2 nm/sec respectively in such a manner that the weight ratio of the resulting film could be controlled to a level of 1-1:2-1=40:2. The resulting film serves as a light-emitting layer.

Then tris(8-hydroxyquinolino) aluminum was vapor-deposited, to a thickness of 20 nm, on the light-emitting layer at an evaporation velocity of 2 nm/sec to thus form an electron-transporting layer.

Furthermore, lithium fluoride was vapor-deposited, to a thickness of 1 nm, on the electron-transporting layer at an evaporation velocity of 0.1 nm/sec to thus form an electron-injecting layer.

Finally, aluminum was vapor-deposited, to a thickness of 200 nm, on the electron-injecting layer at an evaporation velocity of 2 nm/sec to thus form a cathode layer.

(2) Evaluation of Organic EL Element

The resulting element was subjected to a test in which an electric current was applied thereto and as a result, it was confirmed that the element could emit light at a luminance of 700 cd/m$^2$ at an electric voltage of 6.5V and that the emitted light was found to be blue. Separately, the element was operated at a constant current while the initial luminance of the emitted light was set at 100 cd/m$^2$, and as a result, it was found that it had a half life of not less than 10,000 hours and that the element could be practically acceptable without any trouble. The results obtained in these tests are listed in the following Table 1.

Examples 2 and 3

The same procedures used in Example 1 were repeated except for using the compound B in Example 2 and the compound C in Example 3 in place of the compound A used in Example 1 to thus form each corresponding organic EL element.

As a result, it was found that all of the elements prepared in these Examples could emit blue light rays as shown in Table 1 and that each element could emit light at a luminance ranging from 670 to 690 cd/m$^2$ and had a half life of not less than 10,00 hours.

Examples 4 to 7

The same procedures used in Example 1 were repeated except for using the compound (2a'-59) in Example 4, the compound (2b-42) in Example 5, the compound (2c-1) in Example 6, and the compound (2d-1) in Example 7 in place of the compound (2a'-55) used in Example 1 to thus form each corresponding organic EL element.

As a result, it was found, as shown in Tables 1 and 2, that all of the elements prepared in these Examples could emit blue light rays and that each element could emit light at a luminance ranging from 650 to 710 cd/m$^2$ and had a half life of not less than 10,00 hours.

TABLE 1

| | Ex. No. | | | | |
|---|---|---|---|---|---|
| | 1 | 2 | 3 | 4 | 5 |
| Light-Emitting Material 1 | 2a'-55 | 2a'-55 | 2a'-55 | 2a'-59 | 2b-42 |
| Light-Emitting Material 2 | A | B | C | A | A |
| Working Voltage (V) | 6.5 | 6.5 | 6.5 | 6.5 | 6.5 |
| Color of Emitted Light | Blue | Blue | Blue | Blue | Blue |
| Luminance of Emitted Light (cd/m$^2$) | 700 | 690 | 670 | 710 | 650 |
| Half Life (hour) | >10,000 | >10,000 | >10,000 | >10,000 | >10,000 |

TABLE 2

| | Ex. No. | | | | |
|---|---|---|---|---|---|
| | 6 | 7 | 1* | 2* | 3* |
| Light-Emitting Material 1 | 2c-1 | 2d-1 | 2a'-59 | 2a'-59 | 2a'-59 |
| Light-Emitting Material 2 | A | A | D | E | F |
| Working Voltage (V) | 6.5 | 6.5 | 7.0 | 6.5 | 7 |
| Color of Emitted Light | Blue | Blue | Blue | Blue | Blue |
| Luminance of Emitted Light (cd/m$^2$) | 660 | 670 | 500 | 300 | 460 |
| Half Life (hour) | >10,000 | >10,000 | 7,000 | 3,000 | 5,000 |

*Comparative Example

Comparative Examples 1 to 3

The same procedures used in Example 4 were repeated except for using the compound D in Comparative Example 1, the compound E in Comparative Example 2, and the compound F in Comparative Example 3 in place of the compound A used in Example 4 to thus form each corresponding organic EL element.

As a result, it was found, as shown in Table 2, that all of the elements prepared in these Comparative Examples could emit blue light rays and that each element could emit light at an luminance ranging from 300 to 500 cd/m$^2$ and had a rather short half life ranging from 3,000 to 7,000 hours.

Compound A

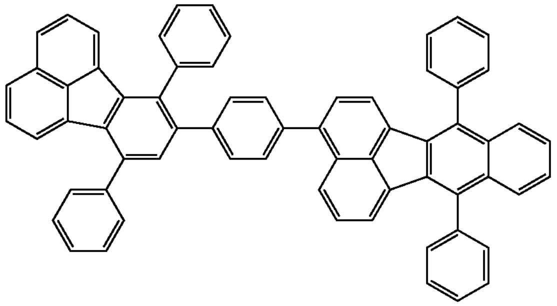

Compound B

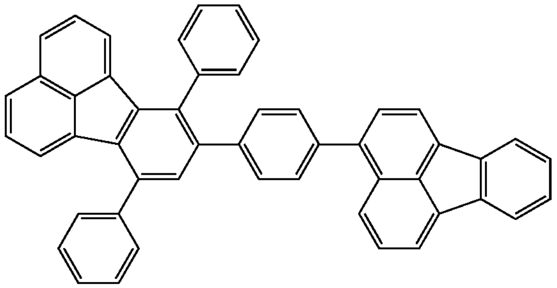

Compound C

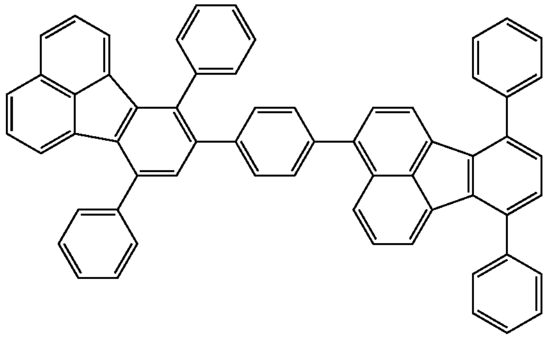

Compound D

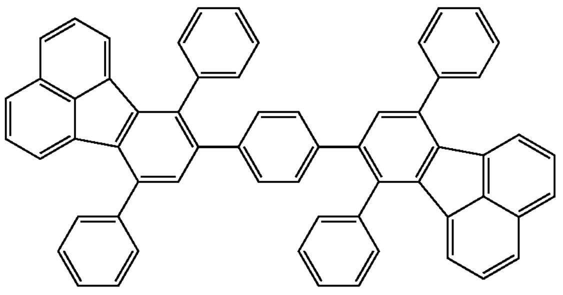

Compound E

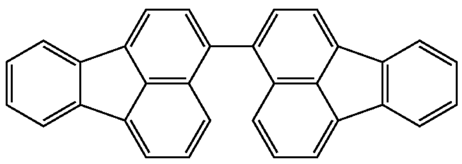

-continued

Compound F

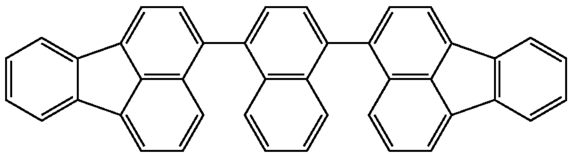

INDUSTRIAL APPLICABILITY

As has been described above in detail, the organic electroluminescent element according to the present invention is provided with a light-emitting layer which comprises at least one member selected from the group consisting of fluoranthene compounds represented by the foregoing general formula (1) and at least one member selected from the group consisting of compounds each having the structure represented by the foregoing general formulas (2a) to (2d). Accordingly, the organic EL element of the invention shows a high luminance and a longer lifetime. For this reason, the organic EL element of the invention is highly practicable and accordingly, it is quite effective as, for instance, a light source for a flat plate-like light-emitting body of a wall type television and a display device. The organic El element can likewise be used as an organic EL element, a hole-injecting and transporting material as well as a charge-transfer component for use in the electrophotographic light-sensitive materials and the semiconductor materials.

What is claimed is:

1. A fluoranthene compound represented by general formula (1):

A-L-B (1)

wherein A and B each represent a monovalent group having a fluoranthene structure represented by general formula (2), wherein A is linked to the group L appearing in the compound of the general formula (1), at a carbon atom selected from the group consisting of carbon atoms specified by numerical values of 7 to 10 appearing in the formula (2); B is linked to the group L present in the compound of the formula (1), at a carbon atom selected from the group consisting of carbon atoms specified by numerical values of 1 to 6 appearing in the formula (2); and at least one of A and B has at least one substituent:

(2)

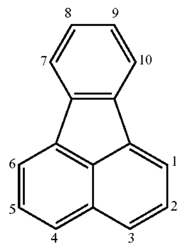

, and wherein L is a member selected from the group consisting of a single bond, substituted or unsubstituted arylene groups each having 6 to 40 carbon atoms, divalent groups derived from arylamines each having 6 to 40 carbon atoms (wherein the aryl group may have a substituent), divalent groups derived from substituted or unsubstituted heterocyclic rings each having 3 to 40 carbon atoms and substituted or unsubstituted ethenylene groups, wherein B can also be the following general formula (5):

(5)

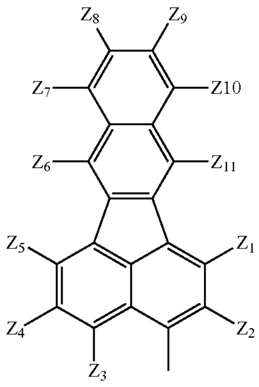

wherein $Z_1$ to $Z_{11}$ each represent a member selected from the group consisting of a hydrogen atom, substituted or unsubstituted aryl or heteroaryl groups whose nucleic atom number ranges from 5 to 50, substituted or unsubstituted alkyl groups each having 1 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 2 to 50 carbon atoms, amino groups each having a substituted or unsubstituted aryl group whose nucleic atom number ranges from 5 to 50, halogen atoms, a cyano group, a nitro group, a hydroxyl group, and a carboxyl group; or in these groups and $Z_1$ to $Z_{11}$, any possible combination of neighboring groups may be bonded together to thus form a saturated or unsaturated ring structure and the resulting ring structure may have a substituent.

2. The fluoranthene compound of claim 1, wherein the group A appearing in the foregoing general formula (1) is a monovalent group represented by the following general formula (3) and the group B appearing in the foregoing general formula (1) is a monovalent group represented by the following general formula (4) or (5):

(3)

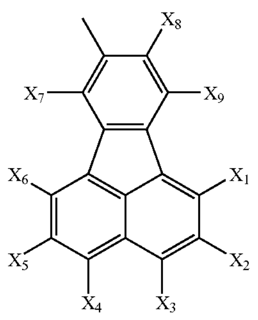

-continued (4)

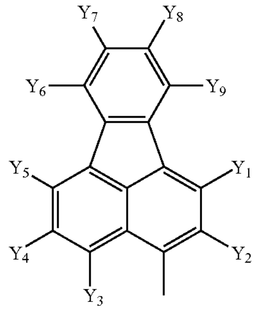

(5)

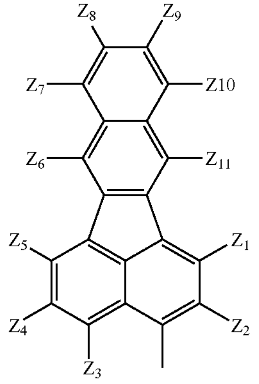

wherein $X_1$ to $X_9$, $Y_1$ to $Y_9$, and $Z_1$ to $Z_{11}$ each represent a member selected from the group consisting of a hydrogen atom, substituted or unsubstituted aryl or heteroaryl groups whose nucleic atom number ranges from 5 to 50, substituted or unsubstituted alkyl groups each having 1 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 2 to 50 carbon atoms, amino groups each having a substituted or unsubstituted aryl group whose nucleic atom number ranges from 5 to 50, halogen atoms, a cyano group, a nitro group, a hydroxyl group, and a carboxyl group; or in these groups $X_1$ to $X_9$, $Y_1$ to $Y_9$, and $Z_1$ to $Z_{11}$, any possible combination of neighboring groups may be bonded together to thus form a saturated or unsaturated ring structure and the resulting ring structure may have a substituent.

3. A material for an organic electroluminescent element comprising a fluoranthene compound of claim 1.

4. A light-emitting material comprising a fluoranthene compound of claim 1.

5. An organic electroluminescent element in which an organic compound layer having a single layer or multiple-layer structure comprising at least a light-emitting layer is sandwiched between a pair of electrodes, the electroluminescent element being characterized in that it comprises at least one fluoranthene compound of claim 1.

6. The organic electroluminescent element as set forth in claim 5, wherein the light-emitting layer comprises said at least one fluoranthene compound.

7. The organic electroluminescent element of claim 6, wherein the light-emitting layer further comprises at least one member selected from the group consisting of compounds represented by the following general formulas (2a) to (2d):

(2a)

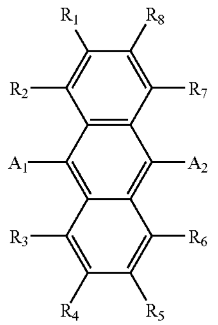

wherein $A_l$ and $A_2$ each independently represent a group derived from a substituted or unsubstituted aromatic ring whose nucleic carbon atom number ranges from 6 to 20; the aromatic ring may have at least one substituent; the foregoing substituent is a member selected from the group consisting of substituted or unsubstituted aryl groups whose nucleic atom number ranges from 6 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group; provided that when the foregoing aromatic ring has at least 2 substituents, these substituents may be the same or different and any possible neighboring substituents may be bonded together to form a saturated or unsaturated ring structure;

$R_1$ to $R_8$ each independently represent a member selected from the group consisting of a hydrogen atom, substituted or unsubstituted aryl groups whose nucleic carbon atom number ranges from 6 to 50, substituted or unsubstituted heteroaryl groups whose nucleic atom number ranges from 5 to 50, substituted or unsubstituted alkyl groups each having 1 to 50 carbon atoms, substituted or unsubstituted cycloalkyl groups each having 3 to 50 carbon atoms, substituted or unsubstituted alkoxy groups each having 1 to 50 carbon atoms, substituted or unsubstituted aralkyl groups each having 6 to 50 carbon atoms, substituted or unsubstituted aryloxy groups whose nucleic atom number ranges from 5 to 50, substituted or unsubstituted arylthio groups whose nucleic atom number ranges from 5 to 50, substituted or unsubstituted alkoxy-carbonyl groups each having 1 to 50 carbon atoms, substituted or unsubstituted silyl groups, a carboxyl group, halogen atoms, a cyano group, a nitro group and a hydroxyl group;

(2b)

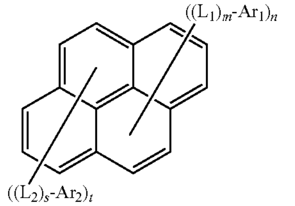

wherein $Ar_1$ and $Ar_2$ each independently represent a substituted or unsubstituted aryl group whose nucleic carbon atom number ranges from 6 to 50;

$L_1$ and $L_2$ each independently represent a member selected from the group consisting of substituted or unsubstituted phenylene groups, substituted or unsubstituted naphthalenylene groups, substituted or unsubstituted fluorenylene groups and substituted or unsubstituted dibenzosilolylene groups;

m is an integer ranging from 0 to 2, n an integer ranging from 1 to 4, s an integer ranging from 0 to 2, and t an integer ranging from 0 to 4;

provided that the group $L_1$ or $Ar_1$ is bonded to any one of the positions 1 to 5 on the pyrene nuclei, while the group $L_2$ or $Ar_2$ is bonded to any one of the positions 6 to 10 on the pyrene nuclei;

(2c)

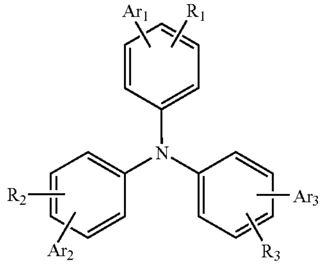

wherein $Ar_1$, $Ar_2$ and $Ar_3$ each independently represent a member selected from the group consisting of anthracene structure-containing groups, phenanthrene structure-containing groups, pyrene structure-containing groups and perylene structure-containing groups;

$R_1$, $R_2$ and $R_3$ each independently represent a hydrogen atom or a substituent;

(2d)

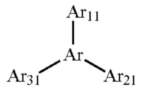

wherein $Ar_{11}$, $Ar_{21}$ and $Ar_{31}$ each independently represent an aryl group whose nucleic carbon atom number ranges from 6 to 50, wherein the aryl group may have at least one substituent;

provided that at least one of the groups $Ar_{11}$, $Ar_{21}$, $Ar_{31}$ and the substituents present in the foregoing aryl groups represented by these groups $Ar_{11}$, $Ar_{21}$ and $Ar_{31}$ has a fused aryl ring structure having a nucleic carbon atom number ranging from 10 to 20 or a fused heteroaryl ring structure having a nucleic carbon atom number ranging from 6 to 20;

Ar represents a trivalent group derived from an aromatic or heteroaromatic ring.

8. The organic electroluminescent element of claim 5, wherein the light-emitting layer comprises the fluoranthene compound in an amount ranging from 0.01 to 20% by mass.

9. The organic electroluminescent element of claim 5, wherein the a layer selected from the groups consisting of chalcogenide layers, metal halide layers and metal oxide layers is arranged on the surface of at least one of the paired electrodes.

10. A device comprising an organic electroluminescent element of claim 5.

* * * * *